(12) United States Patent
Scherman et al.

(10) Patent No.: US 11,530,317 B2
(45) Date of Patent: Dec. 20, 2022

(54) DEEP EUTECTIC SOLVENT COMPOSITIONS

(71) Applicant: SABIC GLOBAL TECHNOLOGIES B.V., Bergen op Zoom (NL)

(72) Inventors: Oren A. Scherman, Cambridgeshire (GB); Jade A. McCune, Cambridgeshire (GB)

(73) Assignee: SHPP GLOBAL TECHNOLOGIES B.V., Bergen op Zoom (NL)

( * ) Notice: Subject to any disclaimer, the term of this patent is extended or adjusted under 35 U.S.C. 154(b) by 19 days.

(21) Appl. No.: 16/494,653

(22) PCT Filed: Mar. 16, 2018

(86) PCT No.: PCT/EP2018/056764
§ 371 (c)(1),
(2) Date: Sep. 16, 2019

(87) PCT Pub. No.: WO2018/167315
PCT Pub. Date: Sep. 20, 2018

(65) Prior Publication Data
US 2020/0095400 A1    Mar. 26, 2020

(30) Foreign Application Priority Data
Mar. 16, 2017   (GB) ..................... 1704222

(51) Int. Cl.
*C08L 5/16*       (2006.01)
*C08B 37/16*      (2006.01)
(Continued)

(52) U.S. Cl.
CPC .............. *C08L 5/16* (2013.01); *C07D 213/22* (2013.01); *C07D 487/04* (2013.01);
(Continued)

(58) Field of Classification Search
CPC ........ C08L 5/16; C08B 37/0015; C08J 3/096; C08J 3/11; C07D 487/04; C07D 213/22;
(Continued)

(56) References Cited

U.S. PATENT DOCUMENTS

2009/0008262 A1   1/2009   Al Nashef et al.
2009/0012346 A1   1/2009   Al Nashef et al.

FOREIGN PATENT DOCUMENTS

CN    107383115 A    11/2017
CN    107383930 A    11/2017
(Continued)

OTHER PUBLICATIONS

Jin Cao, Yuhan Shang, Bin Qi, Xuzhuo Sun, Lei Zhang, Huiwen Liu, Haibo Zhang and Xiaohai Zhoua, Synthesis of pillar[n]arenes (n = 5 and 6) with deep eutectic solvent choline chloride 2FeCl3, RSC Adv., 2015, 5, 9993-9996 (Year: 2015).*

(Continued)

*Primary Examiner* — Bijan Ahvazi
(74) *Attorney, Agent, or Firm* — Cantor Colburn LLP

(57) ABSTRACT

Disclosed herein are compositions of a deep eutectic solvent with a host, such as a supramolecular host, and the use of the composition to form a composition comprising the host in complex with one or more guests. The deep eutectic solvent provides an alternative medium to the aqueous-based media that have been used in the art to date. Also disclosed are compositions of a deep eutectic solvent with a redox-active compound, such as a viologen compound, and the use of the composition, for example, in a smart window or for agricultural use, such as in an agricultural product.

11 Claims, 26 Drawing Sheets

(51) Int. Cl.
| | |
|---|---|
| C08J 3/09 | (2006.01) |
| C08J 3/11 | (2006.01) |
| C07D 213/22 | (2006.01) |
| E06B 9/24 | (2006.01) |
| G02F 1/1503 | (2019.01) |
| C07D 487/04 | (2006.01) |

(52) U.S. Cl.
CPC .......... *C08B 37/0015* (2013.01); *C08J 3/096* (2013.01); *C08J 3/11* (2013.01); *E06B 9/24* (2013.01); *G02F 1/1503* (2019.01); *E06B 2009/2464* (2013.01)

(58) Field of Classification Search
CPC ... G02F 1/1503; E06B 9/24; E06B 2009/2464
See application file for complete search history.

(56) References Cited

FOREIGN PATENT DOCUMENTS

| WO | 2006033545 A1 | 3/2006 |
|---|---|---|
| WO | 2018091379 A1 | 5/2018 |

OTHER PUBLICATIONS

Shengyi Dong, Bo Zheng, Feng Wang, and Feihe Huang, Supramolecular Polymers Constructed from Macrocycle-Based Host-Guest Molecular Recognition Motifs, Acc. Chem. Res. 2014, 47, 1982-1994 (Year: 2014).*

Xiaoxia Li, Kyung Ho Row, Development of deep eutectic solvents applied in extraction and separation, J. Sep. Sci. 2016, 39, 3505-3520 (Year: 2016).*

Hai Qian, Dong-Sheng Guo, and Yu Liu, Cucurbituril-Modulated Supramolecular Assemblies: From Cyclic Oligomers to Linear Polymers ,Chem. Eur. J. 2012, 18, 5087-5095 (Year: 2012).*

Emma L. Smith, Andrew P. Abbott, and Karl S. Ryde, Deep Eutectic Solvents (DESs) and Their Applications, Chem. Rev. 2014, 114, 11060-1108 (Year: 2014).*

Hugo Cruz et al, "Deep eutectic solvents (DESs) as low-cost and green electrolytes for electrochromic devices", Green Chemistry,vol. 19, No. 7, Jan. 1, 2017 (Jan. 1, 2017), p. 1653-1658.

International Search Report for International Application No. PCT/EP2018/056764; International Filing Date Mar. 16, 2018; dated Oct. 8, 2018, 6 pages.

Jade A. Mccune et al, "DESolution of CD and CB Macrocycles", Chemistry—A European Journal, vol. 23, No. 36, Jun. 9, 2017 (Jun. 9, 2017), p. 8601-8604.

Jin Cao et al, "Synthesis of pillar[n]arenes (n = 5 and 6) with deep eutectic solvent choline chloride 2FeCl 3", RSC Advances,vol. 5, No. 13, Jan. 1, 2015 (Jan. 1, 2015), pp. 9993-9996.

Lloyd David et al, "The development of an all copper hybrid redox flow battery using deep eutectic solvents", Electrochimica Acta, Elsevier Science Publishers, Barking, GB.vol. 100, Mar. 31, 2013 (Mar. 31, 2013), p. 18-23.

Shengyi Dong et al, "Supramolecular Polymers Constructed from Macrocycle-Based Host-Guest Molecular Recognition Motifs", Accounts of Chemical Research.,vol. 47, No. 7, Mar. 31, 2014 (Mar. 31, 2014), p. 1982-1994.

V.S. Dilimon et al, "Electrochemical preparation of few layer-graphene nanosheets via reduction of oriented exfoliated graphene oxide thin films in acetamide-urea-ammonium nitrate melt under ambient conditions", Thin Solid Films, vol. 519, No. 7, Jan. 1, 2011 (Jan. 1, 2011), p. 2323-2327.

Written Opinion for International Application No. PCT/EP2018/056764; International Filing Date Mar. 16, 2018; dated Oct. 8, 2018, 10 pages.

Xiaoxia Li et al, "Development of deep eutectic solvents applied in extraction and separation : Liquid Chromatography", Journal of Separation Science.,vol. 39, No. 18, Aug. 22, 2016 (Aug. 22, 2016), p. 3505-3520.

* cited by examiner

DEEP EUTECTIC SOLVENT COMPOSITIONS

CROSS REFERENCE TO RELATED APPLICATIONS

This application is a National Stage application of PCT/EP2018/056764, filed Mar. 16, 2018, which claims the benefit of Great Britain Application No. 1704222.7, filed Mar. 16, 2017, both of which are incorporated by reference in their entirety herein.

FIELD OF THE INVENTION

The present invention provides a composition of a deep eutectic solvent with a host, such as a supramolecular host, and the use of the composition to form a composition comprising the host in complex with one or more guests. The present invention also provides a composition of a deep eutectic solvent with a redox-active compound, such as a viologen compound, and the use of the composition, for example, in a smart window or for agricultural use, such as in an agricultural product.

BACKGROUND

Macrocyclic chemistry is an area of significant academic and industrial interest. This is attributed to the unique host-guest chemistry provided by many macrocyclic host molecules, the most notable examples of which include cucurbit[n]urils (CB[n]), cyclodextrins (CDs), calixarenes and crown ethers.

On account of the outstanding molecular recognition and high-affinity binding properties of macrocyclic hosts, it is widely recognised that there is great potential for their use in a variety of applications. Some notable examples include their use as chemical sensors,[1] drug delivery vehicles,[2] and gas capture agents.[3] Furthermore, the distinct cavity size of a macrocycle can enable its use as a nanoreactor to control and catalyse chemical reactions,[4] or conversely to inhibit reaction and therefore act as a supramolecular shield.[5]

However, a significant limitation is the poor solubility of the macrocycle host molecules in water, and their almost negligible solubility in organic solvents; thereby severely limiting their scope with respect to industrial application.[6] In particular, the aqueous solubility of cucurbiturils is seen to be highly dependent on their cavity size: CB[5] and CB[7] show modest solubility, whereas CB[6] and CB[8] are sparingly soluble. Similarly, the solubility of cyclodextrin compounds is also related to the size of the cavity.

Efforts to improve macrocycle solubility have so far included the use of strongly acidic media, with cucurbiturils for example,[7] the use of basic media, with cyclodextrins for example, the encapsulation of a stoichiometric quantity of a guest molecule,[7] and functionalisation of the macrocycle.[8,9]

Typically the solubility of cucurbituril in aqueous solution is improved by the addition of a stoichiometric quantity of an inorganic or organic salt, in which the positively charged cation selectively binds with high affinity within the cavity of the cucurbituril, or to the portals of the cucurbituril, thereby altering its solubility in water. Ionic liquids have also been used as guests to alter the solubility of cucurbituril through formation of a host-guest complex of the cucurbituril with the ionic liquid.

Some of the present inventors have recently described the use of imidazolium-based salts as selective guest molecules to adjust the solubility of cucurbiturils in aqueous solution.[10] In which, the ability to tune the properties of the imidazolium-based salts through exchanging the counter-ion provides an elegant method to isolate and purify CB[n] homologues (where n=5-8).

A further example by Macartney et al. describes the molecular recognition of cholines and phosphonium-cholines by CB [7] in aqueous solution.[11] Generally, the CB-[7] host forms very stable complexes with a variety of choline cations and their phosphonium analogues. It was shown that the stability of the host-guest complexes depends on the type of the cationic head group, alongside the size and charge of the substituent on the opposite end of the guest, and on the length of the alkyl spacer unit.

Due to the significantly poor solubility of cucurbiturils in non-aqueous solvents, there are notably fewer examples that describe organic systems which provide high solvation of CB[n]homologues. To date these examples have been mainly limited to the CB[7] homologue and require the addition of a stoichiometric quantity of guest molecule. The first reported example by Kaifer et al. described a CB[7] host and p-xylylene dipyridinium guest functionalised with large hydrophobic "stoppers", which had improved solubility in acetonitrile (MeCN) and dimethylsulfoxide (DMSO).[12] Further to this Kaifer et al. also described several examples of millimolar solubilities of CB[7] inclusion complexes with (ferrocenylmethyl) trimethylammonium and methylviologen cations in acetonitrile, dimethylformamide (DMF) and DMSO.[13] A maximum solubility of 60 mM in DMSO has also been reported by Masson et al, for CB[7]-bound p-xylylene diammonium (with a trifluoromethanesulfonate anion).[6] Reports of organic solvents capable of dissolving CB[8] via inclusion complexes are even more scarce. To date only one example has been provided. Monhaphol et al. describe a CB[8] interlocked assembly with viologen unit linked to two tris(2,2'-bipyridine)ruthenium substituents which is only partially soluble in acetonitrile.[14]

Enhanced solubility of CB[n] in organic solvents has also been shown to be achieved via equatorial functionalisation of CB[n]. Kim et al. have reported cyclohexanecucurbit[n]urils ($CycH_5CB_5$ and $CycH_6CB_6$) that are soluble in organic solvents.[8,9]

Despite the many efforts to improve the solubility of CB[n] homologues in aqueous systems successful transfer of these methods to non-aqueous solvents has remained elusive. Furthermore, currently existing methodologies typically require the formation of host-guest inclusion complexes which may impact and/or hinder the chemical application of the free CB[n] host. Furthermore, functionalisation of the CB[n] host necessitates additional steps which add to the complexity of the synthesis.

Redox-active molecules such as viologen (V) can undergo one-electron reductions to form radical species. The use of a stimulus to alter the structure and properties of redox-active molecules has been exploited across a wide range of chemistries.[17] Redox-responsive systems are readily switched using electrochemical, chemical or, in some cases, photochemical stimuli. Redox systems are desirable as, unlike other responsive systems, a change in both the charge and spin state of the molecule occurs. These systems have been utilised for many applications including drug delivery,[18] displays,[19] electronic memory,[20] batteries[21] and tuneable materials.[17]

Typical redox-active molecules include metallocenes such as ferrocene and organic radicals, for example, aromatic derivatives such as tetrathiafulvalene, naphthalene diimides and viologen derivatives.

Organic radicals are highly reactive, often short-lived species formed through either the addition of a reducing agent or photochemical means. On account of their open-shell electronic structure they are have attracted much attention based upon their magnetic proper ties, highly reactive nature and desirable spectroscopic behaviour.

These organic radicals hold significant potential in many applications but are limited as they are rapidly quenched by oxygen leading to short lifetimes in air. For example, isolation and characterisation of organic radicals, such as viologens, are often impeded by their instability and transient nature.

Of particular interest are dicationic viologen derivatives, which can undergo a one-electron reduction to form intensely coloured radical cations with chemical and electrochemical applications as electron mediators. These species are stable in the absence of any oxidising agent as the unpaired electron is delocalised across the π-system.[29] However, in the presence of molecular $O_2$ their quenching is extremely rapid.[30]

The electrochromic behaviour of viologen derivatives, in particular the high optical contrast between redox states, has led to their application in electrochromic devices and displays. Companies have produced electrochromic devices based on viologen.

A number of strategies have been developed to address the problem of stability when using viologens.[22-28]

The use of receptors to stabilise MV radical cations has been reported. Kim and co-workers demonstrated enhanced stability upon encapsulation inside a macrocyclic host, cucurbit[n]uril.[31-32]

This concept was shown to be extended to the formation of 2D supramolecular organic frameworks.[33] The formation a crystalline supramolecular complex between $MV^{2+}$ and a bambusuril macrocycle was shown by Sindelar and co-workers.[34] The crystals could undergo photoinduced electron transfer to form $MV^{+\cdot}$ radicals within the crystals, which were found to have a half-life of several hours in air.

Recently, the encapsulation of $MV^{2+}$ in a zeolite resulted in a photochromic material through electron transfer between the $MV^{2+}$ and the anionic zeolite framework. The dense packing of $MV^{2+}$ within the zeolite pores resulted in a short electron transfer pathway and thus photochromic behaviour in addition to stability of the radical state as the framework prevented contact with oxygen.[35]

Stoddart and co-workers have put significant research effort into constructing mechanically interlocked molecules based on $MV^{2+}$. The most exploited example is the formation of cyclobis(paraquat-p-phenylene) (CBPQT4+), "blue box", where two methyl viologen moieties are joined through a spacing bridge to form a box-like structure.[36] Although not air stable, it allows access to a more stable $MV^{+\cdot}$ radical species which can undergo molecular recognition to form charge transfer complexes, and extended structures such as rotaxanes[37] and catenanes.[38-39]

Nevertheless, the poor dication solubility and short radical lifetime of MV in air has limited its applications within current commercial devices. As discussed above many current methods of utilising the desirable properties of viologens actually use substituted or immobilised viologen derivatives requiring additional costly manufacturing steps.

SUMMARY OF THE INVENTION

The present invention provides the use of a deep eutectic solvent as a medium for forming supramolecular complexes with host molecules, such as macrocyclic hosts. The deep eutectic solvent provides an alternative medium to the aqueous-based media that have been used in the art to date.

The present inventors have found that hosts, including macrocyclic hosts such as cucurbituril, may have improved solubility in a deep eutectic solvent compared with the solubility of that host in water, for example. Thus, the present case provides for improved solubility, which in turns allows for a greater range of possible chemistries.

The hosts may also have similar solubility in a deep eutectic solvent compared with the solubility of that host in media under strongly forced conditions, such as highly acidic, basic or concentrated salt conditions. In the present case, host-guest chemistry can be accessed in a deep eutectic solvent without the need for strongly forced conditions.

The prior art has attempted to solubilise hosts, such as cucurbituril and cyclodextrins, through the formation of host-guest complexes having increased solubility in a particular solvent, and typically water. However, the host is inevitably limited or inhibited from participating in the formation of other complexes, as the guest binding site is occupied with the agent (a guest) required to dissolve the host.

The inventors have found that a wide range of different eutectic solvents may be used together with the hosts. This provides for the possibility of altering the solvent in order to improve solubility, or to optimise the chemistries that are performed using the composition, for example to optimise yields, to reduce side reactions and so on. Thus, deep eutectic solvents have wide and general applicability as solvents for supramolecular chemistry.

As expected, different hosts have different solubilities in a particular deep eutectic solvent. The differences may be used to an advantage, for example to separate hosts based on differences in solubility. In this way, a deep eutectic solvent may be used in methods for purifying a host, particularly in methods for purifying a first host from a mixture with a second host, where the first and second hosts have different solubilities in a deep eutectic solvent. Such methods are known for use with aqueous media, and these methods may be developed further using deep eutectic solvents.

Accordingly in a general aspect there is provided the use of a deep eutectic solvent as a solvent for a host, including macrocyclic hosts such as cucurbituril or cyclodextrin. The deep eutectic solvent may also be used to dissolve a host.

In a first aspect of the invention there is provided a composition comprising a deep eutectic solvent and a host. The host may be dissolved in the deep eutectic solvent.

The deep eutectic solvent may be a Type III deep eutectic solvent.

A Type III deep eutectic solvent comprises an ionic species and a hydrogen bond donor species, such as urea. Any suitable hydrogen bond donor may be used, or example, urea, p-toluenesulfonic acid. Any suitable ionic species may be used, for example, choline chloride.

The deep eutectic solvent may be a mixture of choline chloride and urea, or a mixture of p-toluenesulfonic acid and urea, such as a mixture of choline chloride and urea.

The host may be a macrocyclic host, such as cucurbituril, cyclodextrin, calix[n]arene, or a crown ether, such as a cucurbituril.

The composition may be a liquid.

The composition may be provided at a temperature in the range 0 to 90° C., such as 10 to 90° C., such as 12 to 90° C. The composition may be a liquid at these temperatures. As explained in this case, the composition may be a solid at ambient temperature, such as at a temperature in the range 0 to 25° C. In use the composition may be provided at a temperature where the composition is in liquid form, and therefore it may be heated above ambient temperature. Generally the physical state of the composition is dictated by the deep eutectic solvent, which may be a liquid, and may be provided at the temperatures specified.

The host may be provided in the deep eutectic solvent at an amount in the range 0.1 mg cm$^{-3}$ to 2 g cm$^{-3}$, such as 0.1 to 100 mg cm$^{-3}$, such as 0.1 to 15 mg cm$^{-3}$.

In a second aspect of the invention there is provided a method for preparing a composition, such as the composition according to the first aspect, the method comprising the step of mixing a deep eutectic solvent with a host.

In a third aspect of the invention there is provided a method for preparing a composition, such as the composition according to the first aspect, the method comprising the step of mixing a component of a deep eutectic solvent with a host, and then subsequently mixing a further component of a deep eutectic solvent together with the component and the host.

In a fourth aspect of the invention there is provided a composition comprising a deep eutectic solvent and a host in complex with one or more guests, for example in the form of a non-covalent binary complex or a non-covalent ternary complex.

In a fifth aspect of the invention there is provided a method of preparing a composition, such as the composition according to the fourth aspect of the invention, the method comprising the steps of providing a composition comprising a deep eutectic solvent, a host and one or more guests, and permitting the host and the one or more guests to form a complex.

The composition may be prepared by mixing a deep eutectic solvent together with the host and the one or more guests. The components may be mixed in any order. Where the deep eutectic solvent comprises first and second components, these may be mixed in any order together with the host and the one or more guests.

In a sixth aspect there is provided a method of preparing a composition, such as the composition according to the fourth aspect, the method comprising the step of mixing a deep eutectic solvent with a host in complex with one or more guests.

In a seventh aspect of the invention there is provided a method of synthesis, the method comprising the steps of providing a composition comprising a deep eutectic solvent and a host in complex with one or more guests, and reacting the complex, for example in a reduction or oxidation reaction.

Accordingly in an additional general aspect there is provided the use of a deep eutectic solvent as a solvent for a redox-active compounds, including organic redox-active compound such as viologens.

In another aspect of the invention there is provided a composition comprising a deep eutectic solvent and a redox-active compound.

The deep eutectic solvent may be a Type III deep eutectic solvent.

A Type III deep eutectic solvent comprises an ionic species and a hydrogen bond donor species, such as urea. Any suitable hydrogen bond donor may be used, for example, urea, p-toluenesulfonic acid. Any suitable ionic species may be used, for example, choline chloride.

The deep eutectic solvent may be a mixture of choline chloride and urea, a mixture of choline chloride and ethylene glycol, or a mixture of choline chloride and glycerol.

These and other aspects and embodiments of the invention are described in further detail below.

DETAILED DESCRIPTION OF THE INVENTION

Figure 1:
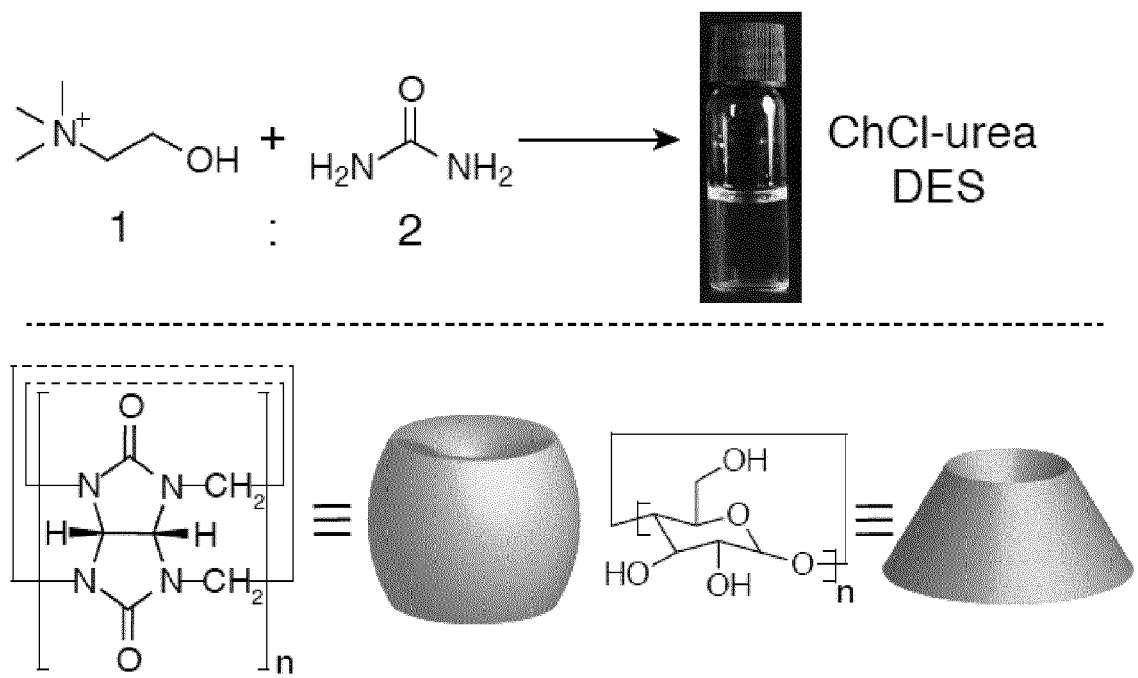
FIG. 1 shows schematic for the synthesis of ChCl-urea (1:2) DES (top), and schematic for the structure of CB[n]s (left) and CDs (right).
Figure 2:
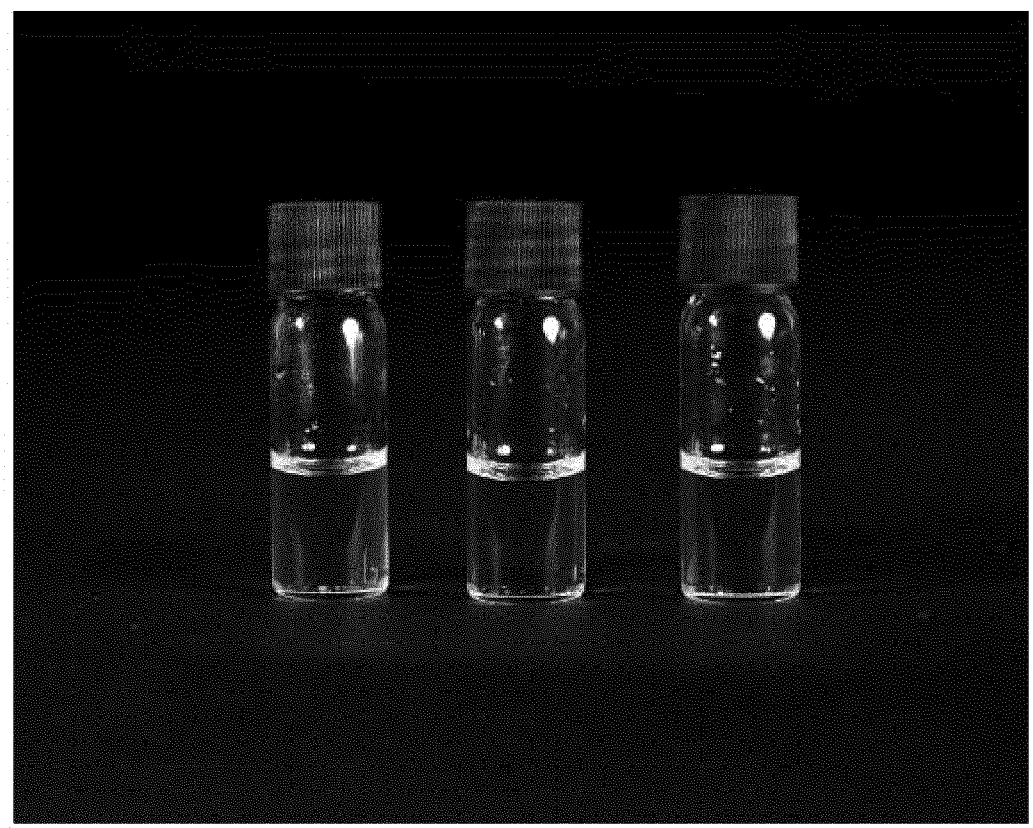
FIG. 2 shows vials containing, from left to right, 0.1 mg, 0.5 mg, and 1 mg of CB[6] dissolved in 1 ml of ChCl-urea DES (1:2).
Figure 3:
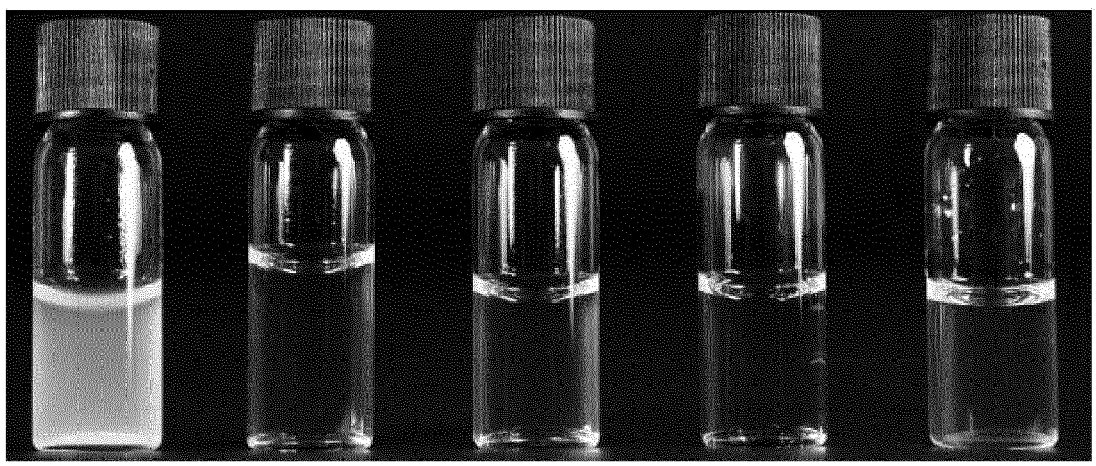
FIG. 3 shows images of vials with CB[7][(15 mg) dissolved in (from left to right) H$_2$O, NaCl, (0.1 M), phosphate buffer (pH=7), HCl (3 M) and ChCh-urea DES (1:2).

The present invention provides the use of a deep eutectic solvent together with host compounds, such as those for use in supramolecular chemistry. The deep eutectic solvent is capable of dissolving hosts and guests for the host, and allowing the hosts and guest to form non-covalent host-guest complexes.

The present invention also provides the use of a deep eutectic solvent together with a redox-active compound, such as an organic redox-active compound, for example a viologen. The deep eutectic solvent is capable of stabilising the redox-active compound and provides a stable solution of the radical form of the redox-active compound.

The compositions and the components of the composition are described in further detail below.

Host Compositions

The present invention provides a composition comprising a deep eutectic solvent and a host. The composition may be used to prepare compositions comprising the host in complex with one or more guests. Thus, host-guest chemistry is possible within the deep eutectic solvent. The host-guest complex may be formed by simple addition of the guests into the composition comprising the deep eutectic solvent and the host. Thus, the composition may comprise a deep eutectic solvent and a complex of a host with one or more guests.

The host may be present in the composition at relatively high levels, and the host may be present at levels that are not achievable under purely aqueous conditions. The inventors have found that a deep eutectic solvent may be capable of solubilising a host at a relatively high level, for example at a level greater that seen in water, or under forcing conditions, such as using strong acid, strong base or concentrated salt conditions. The composition may contain one or more hosts.

The deep eutectic solvent is typically the majority component of the composition. The remainder portion of the composition may include the host and the guests, where present, optionally together with other components.

The inventors have found that a deep eutectic solvent may hold a host, such as cucurbituril, at high concentration, such as up to 10 wt %. Hosts may also be present at very high concentrations, such as cyclodextrin, which may be provided at up to 50 wt %.

A host may be present in the composition at an amount that is at most 1 wt %, at most 2 wt %, at most 5 wt %, at most 10 wt %, at most 20 wt %, at most 30 wt %, at most 40 wt %, at most 50 wt % or at most 60 wt %.

A host may be present in the composition at an amount that is at least 0.01 wt %, at least 0.05 wt %, at least 0.10 wt %, at least 0.15 wt %, or at least 0.5 wt %.

A host may be present in the composition at an amount that is within a range with the minimum and maximum amounts selected from the limits given above. For example, the host, such as cucurbituril, may be present in the composition in the range 0.05 to 2 wt %. For example, the host, such as cyclodextrin, may be present in the composition in the range 0.5 to 50 wt %.

A host may be provided in the deep eutectic solvent at an amount that is at most 2,000, at most 1,000, at most 500, at most 100, at most 50, at most 20, at most 15, at most 10, at most 5, at most 1, or at most 0.01 mg cm$^{-3}$.

A host may be provided in the deep eutectic solvent at an amount that is at least 0.1, at least 0.5, at least 1.0 or at least 5.0 µg cm$^{-3}$.

The host may be provided in the deep eutectic solvent at an amount that is within a range with the minimum and maximum amounts selected from the limits given above. For example, the host, such as cucurbituril, may be provided in the deep eutectic solvent at an amount in the range 0.1 to 15 mg cm$^{-3}$. For example, the host, such as cyclodextrin, may be present in the composition in the range 0.1 to 1,000 mg cm$^{-3}$.

A host may have a maximum solubility in the deep eutectic solvent that is at least 1, at least 2, at least 5, at least 10, at least 15, at least 20, at least 50, at least 100, at least 500, at least 1,000 at least 2,000 or at least 2,500 mg cm$^{-3}$.

A host may have a maximum solubility in the deep eutectic solvent that is at most 50, at most 75, at most 100 or at most 200 mg cm$^{-3}$. The host may have a maximum solubility that is within a range with the minimum and maximum amounts selected from the limits given above. For example, the host may have a maximum solubility in the range 1 to 2,500 mg cm$^{-3}$, such as 1 to 100 mg cm$^{-3}$. For example, the cucurbituril CB[7] has a maximum solubility in ChCl-urea (1:2) of 15.0 mg cm$^{-3}$ at room temperature. In contrast, CB[7] has a maximum solubility in water of 4.4 mg cm$^{-3}$. Cyclodextrin compounds typically have greater solubilities in deep eutectic solvents.

Here a reference to room temperature is a reference to a temperature in the range such as 15 to 25° C., such as 15, 20 or 25° C.

The solubility of the host may be determined by simple visual inspection of varying concentrations of the host in the deep eutectic solvent, checking for the appearance of particulates in the composition.

A host may also have a low solubility in a deep eutectic solvent. For example, a host may have a maximum solubility of at most 1.0, such as at most 0.5, such as at most 0.1, such as at most 0.05, such as at most 0.01 mg cm$^{-3}$.

A host may be substantially insoluble in the deep eutectic solvent.

For example, the cucurbituril CB[6] has a maximum solubility in ChCl-urea (1:2) of <0.1 mg cm$^{-3}$ at room temperature, and is typically around 1 mg cm$^{-3}$.

As explained in the present case, a difference is insolubility between a host and other components, such as other hosts, may be used advantageously to separate that host from the other component in methods of purification.

The composition comprising the deep eutectic solvent is substantially free of water. Thus, the amount of water present in a composition may be at most 5 wt %, at most 2 wt %, at most 1 wt %, such as at most 0.5 wt %.

Small amounts of water may be present where the components of the deep eutectic solvent are provided as hydrate forms. For example, p-toluenesulfonic acid is commercially available as the monohydrate form, and may be used as such in a deep eutectic solvent.

The interaction of the deep eutectic solvent and the host is not well understood, and references to the host being solubilised in the deep eutectic solvent may not accurately reflect the interactions between the host and the deep eutectic solvent. Without being bound to a theory, the deep eutectic solvent is nevertheless capable of holding a host, and allowing that host to participate in host-guest chemistries. Thus, the host is permitted to bind to guests and form complexes within the deep eutectic solvent. In this way, the deep eutectic solvent is an alternative to the use of aqueous mixtures in host-guest chemistries.

The composition may be provided in liquid form. The composition may be used at a temperature that allows the deep eutectic solvent to have a liquid form.

A composition may be provided in the solid form also, and the sold form may be obtained by cooling of the liquid form of the composition. Where a host-guest complex is present within the composition, that complex remains as such.

The composition may be provided at an elevated temperature, for example to ensure that that deep eutectic solvent is in liquid form.

The composition is typically in liquid form at a temperature of 80° C. or less, such as 70° C. or less, such as 60° C. or less, such as 50° C. or less, such as 40° C. or less, such as 30° C. or less.

The composition may be provided at ambient (room) temperature, such as 15 to 25° C., such as 15, 20 or 25° C. The composition may be a liquid at this temperature.

It is preferred that the composition is provided at a relatively mild temperature. For example, the composition is at a temperature of 80° C. at most, such as 70° C. at most, such as 60° C. at most.

A reference to a liquid form may be a reference to the form of the composition at ambient pressure, for example at 101.3 kPa.

Complex

A composition of the invention may comprise a complex of a host with one or more guests. The complex is based on a host, such as cucurbituril or cyclodextrin, hosting one guest (binary complex) or two guests (ternary complex), or more guests. Each guest is encapsulated and held non-covalently in complex by the host, thus the complex may be referred to as a supramolecular complex. The formation of the complex is tolerant of many functionalities within the guest. Each functionality may be the same or different. The host does not form a covalent bond to the guest. The composition may contain one or more hosts.

Suitable hosts and guests for use in the invention are discussed below.

Where the complex comprises two guests, such as within a cavity of a macrocycle, the association constant, $K_a$, for that complex is at least $10^3$ M$^{-2}$, at least $10^4$ M$^{-2}$, at least $10^5$ M$^{-2}$, at least $10^6$ M$^{-2}$, at least $10^7$ M$^{-2}$, at least $10^8$ M$^{-2}$, at least $10^9$ M$^{-2}$, at least $10^{10}$ M$^{-2}$, at least $10^{11}$ M$^{-2}$, or at least $10^{12}$ M$^{-2}$.

Where a host is in complex with two guest molecules, the guest molecules may be the same or they may be different. A host that is capable of complexing two guest molecules may also be capable of forming a stable binary complex with a single guest. The formation of a ternary host-guest complex is believed to proceed via an intermediate binary complex. Within a composition of the invention, there may be present a binary complex formed between a guest molecule and a cucurbituril or cyclodextrin. The binary complex may be regarded as a partially formed ternary complex that has not yet formed a non-covalent bond to another guest molecule.

Where the complex has one guest, such as within the cavity of a macrocycle, the association constant, $K_a$, for that complex is at least $10^1$ M$^{-1}$, at least $10^2$ M$^{-1}$, at least $10^3$ M$^{-1}$, of at least $10^4$ M$^{-1}$, of at least $10^5$ M$^{-1}$, of at least $10^6$ M$^{-1}$, of at least $10^7$ M$^{-1}$, of at least $10^8$ M$^{-1}$, of at least $10^9$ M$^{-1}$, of at least $10^{10}$ M$^{-1}$, of at least $10^{11}$ M$^{-1}$, of at least $10^{12}$ M$^{-1}$, of at least $10^{13}$ M$^{-1}$, of at least $10^{14}$ M$^{-1}$, of at least $10^{15}$ M$^{-1}$, or of at least $10^{16}$ M$^{-1}$. The guest is may be a compound capable of forming a complex which has an association constant in the range $10^1$ to $10^{14}$ M$^{-1}$, such as $10^4$ to $10^7$ M$^{-1}$.

A complex may be formed by simple admixture of a host with one or more guests. Thus, a host and guests may be together provided in a deep eutectic solvent, and the host and the guest may be permitted to form a supramolecular host-guest complex.

The formation of the complex may be reversible. The separation of a guest from the host may be referred to as decomplexation.

The decomplexation of a complex to separate the guest or guests may occur in response to an external stimulus, including, for example, a competitor guest compound which is added to the composition, light, an oxidising or reducing agent, electrochemical potential, and temperature changes amongst others. Where a competitor guest is used, the competitive guest has a higher association constant than a guest of the complex.

Hosts and Guests

The present case provides for the use of a host in a deep eutectic solvent. A host here refers to a molecule, such as a macromolecule, that is capable of forming a non-covalent complex with a guest. A host typically refers to a compound that is capable of holding one or more guests, for example within a cavity of the host. The composition may contain one or more hosts.

The hosts for use in the present case are typically macrocyclic compounds, including cucurbituril and cyclodextrin compounds. Thus, the host has a macrocyclic ring. The host is therefore a macromolecule that is cyclic or has a macromolecular cyclic portion.

A macrocyclic ring may refer to a ring that has at least 20 atoms forming a ring, such as at least 24 atoms, such as at least 28 atoms, such as at least 50 atoms.

The macrocycle comprises a plurality of repeating molecular subunits. The macrocycle may contain four or more, such as five or more, repeat units. These units may be the same or different, and typically they are the same.

The macrocycle defines a cavity which is suitable for holding a guest. The cavity is accessible to a guest, which is capable of entering the cavity and forming non-covalent bonds with the host. An example macrocycle includes cucurbituril which has five or more repeat glycoluril units, which units may be the same or different. Similarly, cyclodextrin has six or more repeat sugar units, which units may be the same or different.

The cavity may have a size that is at least 100, at least 200, at least 300, or at least 400 Å$^3$. The cavity may have a size that is at most 600, at most 700, at most 800, at most 900, at most 1,000, at most 2,000 or at most 5,000 Å$^3$.

The cavity may have a size that is that is in a range with the lower and upper limits selected from those given above. For example, the cavity may have a size that is in the range 300 to 1,000 cubic angstrom (Å$^3$).

As an example, CB[8], a host for use in the present invention, has an internal cavity size of 479 Å$^3$.

The cavity is suitable for holding a guest that is a small molecule or a substituent group of a larger molecule, where that molecule or substituent group has at least 2 atoms, such as having at least 4 atoms, such as at least 10 atoms.

The host may also possess portals at the outer edge of the cavity. These portals may also form non-covalent bonds with a compound. Where a compound is bound to the portal only, and that compound is not contained within a cavity, the relationship between the compound and the host is not referred to as a host-guest relationship or a complex of a guest with a host, as the compound is not contained within the host, for example is not contained in the cavity of the host. Where a compound is bound to the portal only, and is not encapsulated by the host, the complex may sometimes be referred to as an exclusion complex.

A reference to a host includes a reference to the salts forms thereof.

A host may have a molecular weight that is at least 500 Dalton (Da), at least 750 Da, or at least 1,000 Da.

A host may have a molecular weight that is at most 1,500 Da, at most 2,000 Da, at most 2,500 Da, at most 5,000 Da, at most 10,000 Da or at most 25,000 Da.

The host may have a molecular weight that is in a range with the lower and upper limits selected from those given above. For example, a host may have a molecular weight that is in the range 750 Da to 2,500 Da.

The host may be soluble in the deep eutectic solvent. Preferred solubilities for the host are discussed above in the discussion on Compositions.

A host may be covalently connected to another host.

A host for use in the compositions of the present case includes a host selected from the group consisting of cucurbituril, cyclodextrin and calixarene. It is preferred that the host is a cucurbituril or a cyclodextrin, and most preferably a cucurbituril.

A reference to a guest herein is typically not a reference to the components of the DES solvent. Although it is recognised that a component of the DES, such as choline, is capable of forming a guest-host complex in aqueous environments, the DES components are typically weakly binding. A guest for use in the invention is typically not a component of a DES solvent, and the guest is typically capable of displacing any DES component held in complex with a host.

Cucurbituril

The present invention provides for the use of cucurbituril as a host for guest molecules. The cucurbituril may be used to form ternary complexes with first and second guest molecules (which molecules may be the same or different), or binary complexes with a first guest molecules.

A cucurbituril for use may be capable of forming a ternary complex. For example, CB[8] is capable of forming a ternary complex. As too are CB[10], CB [13], CB [14] and CB[15]. The cucurbiturils CB[9], CB[11] and CB[12] are also expected to form ternary complexes.

A cucurbituril for use may be capable of forming a binary complex. For example, CB[5], CB[6] and CB[7] are capable of forming a ternary complex. As too is CB[8] with the appropriate guest molecule.

In one embodiment, the cucurbituril is a CB[5], CB[6], CB[7], CB[8], CB[9], CB[10], CB[11], CB[12], CB[13], CB[14] or CB[15] compound.

In one embodiment, the cucurbituril is a CB[5], CB[6], CB[7], CB[8], CB[9], CB[10], CB[11] or CB[12] compound.

In one embodiment, the cucurbituril is a CB[7] compound, such as CB[7] or a CB[8] compound, such as CB[8].

References to a cucurbituril compound are references to variants and derivatives thereof.

Cucurbit[8]uril (CB[8]; CAS 259886-51-6) is a barrel shaped container molecule which has eight repeat glycoluril units and an internal cavity size of 479A³ (see structure below). CB[8] is readily synthesised using standard techniques and is available commercially (e.g. Sigma-Aldrich, MO USA). The cucurbituril CB[7] is also available commercially.

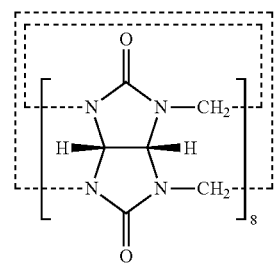

Methods for the preparation and isolation of alternative cucurbituril compounds are well known in the art.

Where a complex of a cucurbituril is provided, the guest in the complex is held within the cavity of the cucurbituril. The reference to host-guest complexes does not refer to a non-covalent binding pair formed between the portals of the cucurbituril and another component.

Cucurbituril variants are provided for use in the invention. A variant of a cucurbituril, such as a variant of CB[8], may include a structure having one or more repeat units that are structurally analogous to glycoluril. The repeat unit may include an ethylurea unit. Where all the units are ethylurea units, the variant is a hemicucurbituril. The variant may be a hemicucurbit[12]uril (shown below, see also Lagona et al. *Angew. Chem. Int. Ed.* 2005, 44, 4844).

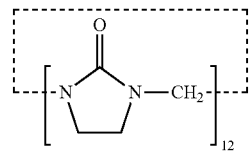

Cucurbituril derivatives find use in the compositions and methods described herein. A derivative of a cucurbituril is a structure having one, two, three, four or more substituted glycoluril units. A substituted cucurbituril compound may be represented by the structure below:

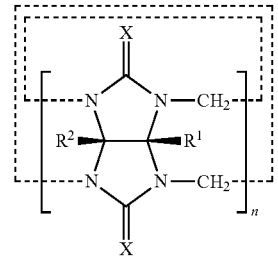

wherein:
n is an integer of at least 5;
and for each glycoluril unit
each X is O, S or NR³, and
—R¹ and —R² are each independently selected from
—H and the following optionally substituted groups:
—R³, —OH, —OR³, —COOH, —COOR³, —NH₂, —NHR³ and —N(R³)₂ where —R³ is independently selected from $C_{1-20}$alkyl, $C_{6-20}$carboaryl, and $C_{5-20}$heteroaryl, or where —R¹ and/or —R² is —N(R³)₂, both —R³ together form a $C_{5-7}$ heterocyclic ring; or together —R¹ and —R² are $C_{4-6}$alkylene forming a $C_{6-8}$carbocyclic ring together with the uracil frame.

Alternatively, one of —$R^1$ and —$R^2$, for example in one of the glycoluril units, is a group containing a polymer, such as a polypeptide including a protein or a carbohydrate, or a detectable label, such as a dye.

Alternatively, one or more of the methylene bridges linking the gycoluril units, such as one methylene bridge, in a cucurbituril is optionally substituted, for example substituted with alkyl, aralkyl or aralkenyl.

The alkyl may be $C_{1-6}$ alkyl, such as $C_{1-4}$ alkyl.

The aralkyl may be a phenyl group linked via a $C_{1-6}$ alkylene linker, such as a $C_{1-4}$ alkylene linker.

The aralkenyl may be a phenyl group linked via a $C_{2-6}$ alkenylene linker, such as a $C_{2-6}$ alkylene linker.

For example, Gilberg et al. have described CB[6] compounds where one methylene bridge is substituted with alkyl, aralkyl or aralkenyl.

In one embodiment, only one of the glycoluril units within the cucurbituril is a substituted glycoluril unit. Here, —$R^1$ and —$R^2$ are each independently —H for n−1 of the glycoluril units.

The number of repeat units, n, within the cucurbit[n]uril may be 5, 6, 7, 8, 9, 10, 11, 12, 13, 14 and 15, such as 5, 6, 7, 8, 10 or 12. Preferably, n is 7 or 8.

Preferably each X is O. Each X may be S.

Each —$R^1$ and —$R^2$ may independently be H.

In one embodiment, for each unit one of —$R^1$ and —$R^2$ is H and the other is independently selected from —H and the following optionally substituted groups: —$R^3$, —OH, —$OR^3$, —COOH, —$COOR^3$, —$NH_2$, —$NHR^3$ and —$N(R^3)_2$. In one embodiment, for one unit one of $R^1$ and $R^2$ is H and the other is independently selected from —H and the following optionally substituted groups: —$R^3$, —OH, —$OR^3$, —COOH, —$COOR^3$, —$NH_2$, —$NHR^3$ and —$N(R^3)_2$. In this embodiment, the remaining glycoluril units are such that $R^1$ and $R^2$ are each independently H.

Preferably —$R^3$ is $C_{1-20}$alkyl, most preferably $C_{1-6}$ alkyl. The $C_{1-20}$alkyl group may be linear and/or saturated. Each group —$R^3$ may be independently unsubstituted or substituted. Preferred substituents are selected from: —$R^4$, —OH, —$OR^4$, —SH, —$SR^4$, —COOH, —$COOR^4$, —$NH_2$, —$NHR^4$ and —$N(R^4)_2$, wherein —$R^4$ is selected from $C_{1-20}$ alkyl, $C_{6-20}$ carboaryl, and $C_{5-20}$ heteroaryl. The substituents may be independently selected from —COOH and —$COOR^4$. In some embodiments, —$R^4$ is not the same as —$R^3$. In some embodiments, —$R^4$ is preferably unsubstituted.

Where —$R^1$ and/or —$R^2$ is —$OR^3$, —$NHR^3$ or —$N(R^3)_2$, then —$R^3$ is preferably $C_{1-6}$alkyl. In some embodiments, —$R^3$ is substituted with a substituent —$OR^4$, —$NHR^4$ or —$N(R^4)_2$. Each —$R^4$ is $C_{1-6}$ alkyl and is itself preferably substituted Cucurbituril Guests A cucurbituril may be used to form a complex together with one of more guests. The cucurbituril may form a binary complex with one guest, or a ternary complex with two guests, which guest may the same or different.

The formation of complexes between cucurbituril and one or more, such as one or two guests, is well known in the art.

The guest may be a part of a large molecule, such as a polymer, including a polypeptide such as a protein. Complexes formed from the complexation of cucurbituril with guests covalently linked to polymer molecules are known in the art, including earlier work of the one of the present inventors.

In principal any compound having suitable binding affinity may be used in the methods of the present invention. The compound used may be selected based on the size of the moieties that are thought to interact with the cavity of the cucurbituril. The size of these moieties may be sufficiently large to permit complexation only with larger cucurbituril forms.

Cucurbituril guest molecules are well known in the art. Examples of suitable guest compounds for use include those described in Barrow et al. (Barrow et al., Chem. Rev., 2015, 115, 12320), Masson et al. (Masson et al., RSC Adv., 2012, 2, 1213) and their redox derivatives, Jiao et al. (Jiao et al. Org. Lett. 2011, 13, 3044), Jiao et al. (Jiao et al. J. Am. Chem. Soc. 2010, 132, 15734), Rauwald et al. (Rauwald et al. J. Phys. Chem. 2010, 5 114, 8606) and WO 2011/077099.

The present inventors have investigated complexation of guest molecules with a host within a deep eutectic solvent. The use of cyclic voltammetry and UV-vis spectroscopy have indicated that a binding event occurs between the host and guest within a DES. Thus, the host maintains its host-guest properties with minimal hindrance from the DES.

The guest is preferably a compound which is redox active and/or UV-vis active.

In one embodiment, the guest molecule is, or contains, an alkylviologen, such as methyl viologen.

In one embodiment, the guest molecule is, or contains, adamantane.

Alternative Hosts and Guests

The compositions described herein may contain a host other than cucurbituril. Examples hosts include cyclodextrin, calix[n]arene, and crown ether.

For example, a host may be cyclodextrin. Cyclodextrin compounds are readily available from commercial sources. Many guest compounds for use with cyclodextrin are also known. Cyclodextrin is a non-symmetric barrel shaped cyclic oligomers of D-glucopyranose. Typically, the cyclodextrin is capable of hosting hydrophobic uncharged guests. For example, guests include those molecules having hydrocarbon and aromatic functionalities such as viologen, adamantane, azobenzene, and stilbene derivatives. Other guest molecules for cyclodextrin include biomolecules such as xylose, tryptophan, estriol, estrone and estradiol. A guest for the cyclodextrin may also be a guest for a cucurbituril. Thus, the cyclodextrin guest may be selected from the guests described above for cucurbituril.

The cyclodextrin may be an α-, β- or γ-cyclodextrin, or a mixture thereof. The cyclodextrin may be a β- or γ-cyclodextrin. Typically larger guests are used together with a γ-cyclodextrin.

The cyclodextrin has a toroid geometry, with the secondary hydroxyl groups of the D-glucopyranose located at the larger opening, and the primary hydroxyl groups at the smaller opening. One or more of the hydroxy groups, which may be the secondary or the primary hydroxy groups, may be functionalised. Typically, the primary hydroxyl groups are functionalised. In one embodiment, references to a cyclodextrin compound are references to derivatives thereof. For example, one or two primary hydroxyl groups of the cyclodextrin is functionalised with an alkylamine-containing subsistent. In another example one, two or three of the hydroxyl groups within each D-glucopyranose unit is replaced with an alkyl ether group, for example a methoxy group. A plurality of covalently linked cyclodextrins may be connected via the hydroxyl groups.

Examples of unfunctionalised and functionalised cyclodextrins are set out in Chart 1 of Rekharsky et al. (Chem. Rev. 1998, 98, 1875), and examples of compounds for use as guests are set out over Tables 1 to 3 and Chart 2. Rekharsky et al. is incorporated by reference herein.

In one embodiment, the host is calix[n]arene. Calix[n]arenes compounds are readily available from commercial sources, or may be prepared by condensation of phenol, resorcinol or pyrogallol with aldehydes, for example formaldehyde, acetaldehyde, or iso-valeraldehyde.

Many guest compounds for use with calix[n]arenes are known. Typically, the calix[n]arene is capable of hosting amino-containing molecules. Piperidine-based compounds and amino-functionalised cyclohexyl compounds may find use as guests. Further examples of guests include atropine, crytand, phenol blue, and anthrol blue amongst others.

Examples of unfunctionalised and functionalised calix[n]arenes are set out in Chart 1 of Danil de Namor et al. (*Chem. Rev.* 1998, 98, 2495-2525), which is incorporated by reference herein. Examples of compounds for use as guests are set out over Tables 2, 3, 5 and 10 of Danil de Namor et al.

In one embodiment, the calix[n]arene is a calix[4]arene, calix[5]arene or calix[6]arene. In one embodiment, the calix[n]arene is a calix[4]arene.

Suitably functionalised calix[n]arenes may be prepared through use of appropriately functionalised hydroxy aryl aldehydes. For example, the hydroxyl group may be replaced with an alkyl ether-containing group or an ethylene glycol-containing group. A plurality of covalently linked calix[n]arenes may be connected via the hydroxyl groups.

In one embodiment, the host is a crown ether. Crown ether compounds are readily available from commercial sources or may be readily prepared.

Many guest compounds for use with crown ether are also known. For example, cationic guests such as amino- and pyridinium-functionalized molecules may be suitable guest molecules.

Examples of unfunctionalised and functionalised crown ethers are set out throughout Gokel et al. (*Chem. Rev.* 2004, 104, 2723-2750), which is incorporated by reference herein. Examples of compounds for use as guests are described throughout the text.

In one embodiment, the crown ether is selected from the groups consisting of 18-crown-6, dibenzo-18-crown-6, diaza-18-crown-6 and 21-crown-7. Smaller crown ethers may be capable of binding small metal ions only. Larger crown ethers are capable of binding functional groups and molecules.

In some embodiments, the host is a guest having crown ether and calix[n]arene functionality. Such hosts are referred to as calix[n]crowns.

Other host-guest relationships may be used as will be apparent to a person of skill in the art. Other host-guest complexes for use in the present invention include those highlighted by Dsouza et al. (*Chem. Rev.* 2011, 111, 7941-7980) which is incorporated by reference herein, and in particular those hosts set out in Schemes 6 and 7, which includes cucurbituril, cyclodextrin, and calixarene as well as cyclophane AVCyc, calixpyridine C4P and squarimide SQAM.

The use of cyclodextrin is preferred over crown ether and calix[n]arene hosts.

Redox-Active Compositions

The present case provides for the use of a redox-active compound in a deep eutectic solvent.

The present case provides a composition comprising a deep eutectic solvent and a redox-active compound.

In this way, the present case provides a stable solution of redox-active compounds which can be utilised commercially. The use of a deep eutectic solvent provides a non-toxic, facile and inexpensive method to stabilise redox-active compounds.

It is proposed that the nanostructure of the deep eutectic solvent provides a novel supramolecular confined environment which stabilises the redox-active compound, in particular when the redox-active compound is in the radical form.

A redox-active compound here refers to a compound, such as an organic molecule, that is capable of undergoing a reversible one-electron reduction or oxidation to form a radical species.

Included in the term 'redox-active compounds are compounds that are capable of undergoing multiple one-electron oxidations or reductions. That is, the term is not limited to species which can only undergo a single one-electron reduction or oxidation. Further oxidation or reduction processes may result in the pairing of the radical electron and formal charge on the redox-active species, i.e. the radical nature may be removed.

Preferably, the redox-active compound is capable of undergoing a reversible one-electron reduction to form a radical species. It is to be understood that the term "redox-active compound" is inclusive of all forms of the compound, including the corresponding radical species.

The redox-active compounds for use in the present case are typically organic redox-active compounds, including aromatic derivatives such as tetrathiafulvalene, terylenediimide, naphthalene diimides and viologen. Preferably, the redox-active compound is a viologen.

Viologen compounds are organic compounds with the formula $(C_5H_5NR)_2^{n+}$. For example, the viologen may be a 2,4'-bipyridine, a 2,2'-bipyridine or a 4,4'-bipyridine. R may be a $C_{1-12}$ alkyl, such as a $C_{1-8}$ alkyl, a $C_{7-18}$ aralkyl such as benzyl or a $C_{7-18}$ alkaryl such as 4-(n-octyl phenylene).

Viologens, in their dicationic form (i.e. when n is 2), can undergo two one-electron reductions. Viologens in their dicationic form change colour reversibly when they undergo a one-electron transfer redox process.

The viologen may be N,N'-diethyl-4,4'-bipyridinium dichloride or N,N'-dioctyl-4,4'-bipyridinium dibromide, or 1,1'-dibenzyl-4,4'-bipyridinium dichloride. Preferably, the viologen is N,N'-dimethyl-4,4'-bipyridinium dichloride (MV) i.e. where R is methyl. N,N'-dimethyl-4,4'-bipyridinium dichloride is often referred to as methyl viologen (MV) or paraquat.

Typically, viologen compounds have a counterion. Any suitable counterions may be used in the present invention, for example, a chloride, bromide or $PF_6^-$ counterion may be used.

Modified viologen compounds may also be used, for example extended viologens wherein one or more carboaryl, heteroaryl, or alkenylene or alkynylene units are inserted between the pyridine units to provide conjugated molecules. For example, the units may be ethylene, ethynylene, phenylene, or divalent thiophene groups. An example of such viologen compounds includes di-octyl bis(4-pyridyl)biphenyl dibromide. The extended viologens may be based on other aromatic nitrogen-containing aromatic groups, for example di-octyl bis(2-quinolinyl)biphenyl dibromide.

The present invention also provides the use of a composition comprising a deep eutectic solvent and a redox-active compound. The use may include a reversible one-electron reduction or oxidation of the redox-active compound. Preferably, the use includes a one-electron reduction of the redox-active compound.

The reversible one-electron reduction or oxidation can be referred to as a "switching process". It may be carried out using any suitable stimulus. For example, the stimulus may be electrochemical, chemical, photochemical and in some cases thermal stimulus.

Electrochemical stimulus may be provided by applying a voltage to the composition in an electrochemical cell.

Chemical stimulus may be provided by the addition of a reducing agent, for example magnesium, sodium persulfate or monoethanolamine in the case of a one-electron reduction. Chemical stimulus may be provided by the addition of an oxidizing agent in the case of a one-electron oxidation.

Photochemical stimulus may be provided by light, for example UV light or natural light. Preferably, the photochemical stimulus is provided by natural light.

$MV^{2+}$ has shown photochromic behaviour in solution,[53] within films[54] and in the crystalline state leading to applications in photonic devices, erasable data storage systems and liquid crystals. It is proposed that photochromic behaviour of $MV^{2+}$ occurs through photoinduced electron transfer between the counter anion and $MV^{2+}$ cation.[54]

Thermal stimulus may be provided using heat. Any suitable deep eutectic solvent may be used when a thermal stimulus is required. Preferably, when a thermal stimulus is used the composition contains urea. The urea may be provided by the deep eutectic solvent (i.e. the deep eutectic solvent may be urea based), for example, the deep eutectic solvent may be choline chloride and urea based or urea may be added to the composition as an additional component, for example, the deep eutectic solvent may be provided by a mixture of choline chloride and glycerol with urea added as an additional component, preferably the urea is added in a sub-stoichiometric amount.

When the redox-active compound is a viologen, the switching process is accompanied by a colour change. This colour change may be used to monitor the switching process.

The composition comprising a deep eutectic solvent and a redox-active compound may be used in many different applications.

For example, it may be used in smart windows, smart screens, sensors, as an antioxidant, as a flame retardant additive, as a catalyst, as an oxygen vs time sensor or in agriculture.

Smart Windows

Smart window refers to windows wherein the light transmission properties of at least some of the transparent portion of the window, for example the glass or glazing, are altered when voltage, light or heat are applied.

In the present invention, the compositions comprising a deep eutectic solvent and a redox-active compound may be used in a smart window. The colour of at least some of the transparent portion of the window may be changed by stimulating a reversible one-electron reduction or oxidation of the redox-active compound. Methods of stimulating the reversible one-electron reduction or oxidation of the redox-active compound are as discussed above.

In some cases, the transparent portion of the smart window contains an electrochemical cell. The composition comprising a deep eutectic solvent and a redox-active compound is contained within the electrochemical cell. In this case, the method of stimulating the reversible one-electron reduction or oxidation is electrochemical.

The redox behaviour of MV has been exploited in the development of electrochromic devices such as displays, mirrors and smart windows because of the high optical contrast between the $MV^{2+}$ and $MV^{+\cdot}$ states. Typically, this requires chemical modification, immobilisation, encapsulation or incorporation into a nanomaterial to prevent bleaching of the MV+state.

In some cases, the composition for use in a smart window has a viologen as the redox-active compound. In particular, methyl viologen (MV) may be used.

Figure 4:
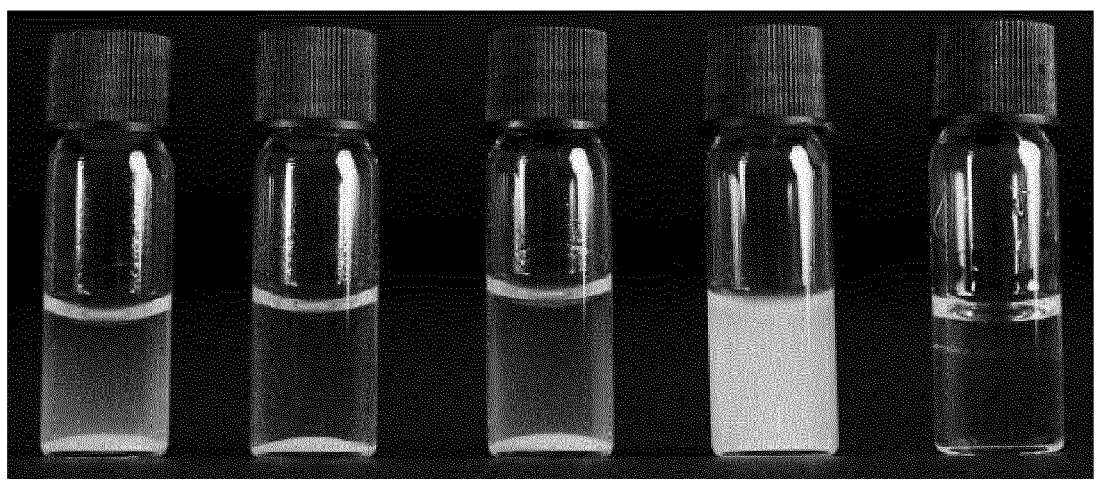
FIG. 4 shows images of vials with CB[8] (2 mg) dissolved in (from left to right) H$_2$O, NaCl, (0.1 M), phosphate buffer (pH=7), HCl (3M) and ChCl-urea DES (1:2).
Figure 5:
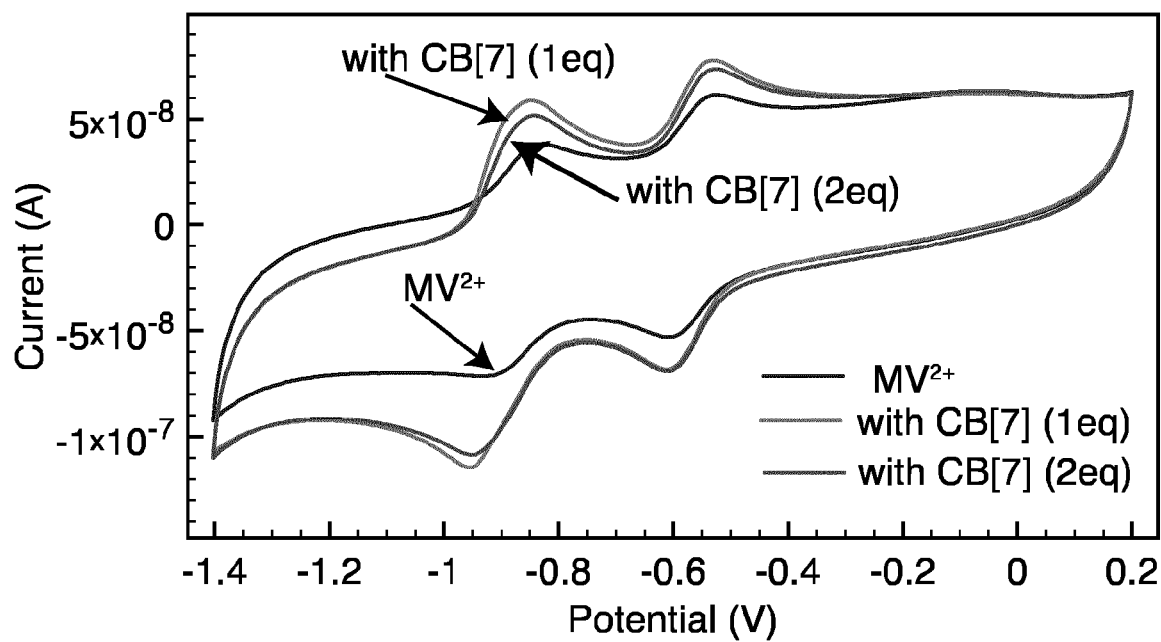
FIG. 5 shows the cyclic voltammogram of MV$^{2+}$ in ChCl-urea DES in the presence of CB[7] with various equivalents of CB[7] (scan rate 50 mV s$^{-1}$). Each sample was run in a 2 mg/mL MV solution in DES. Scans were run from −200 mV to −1400 mV.
Figure 6:
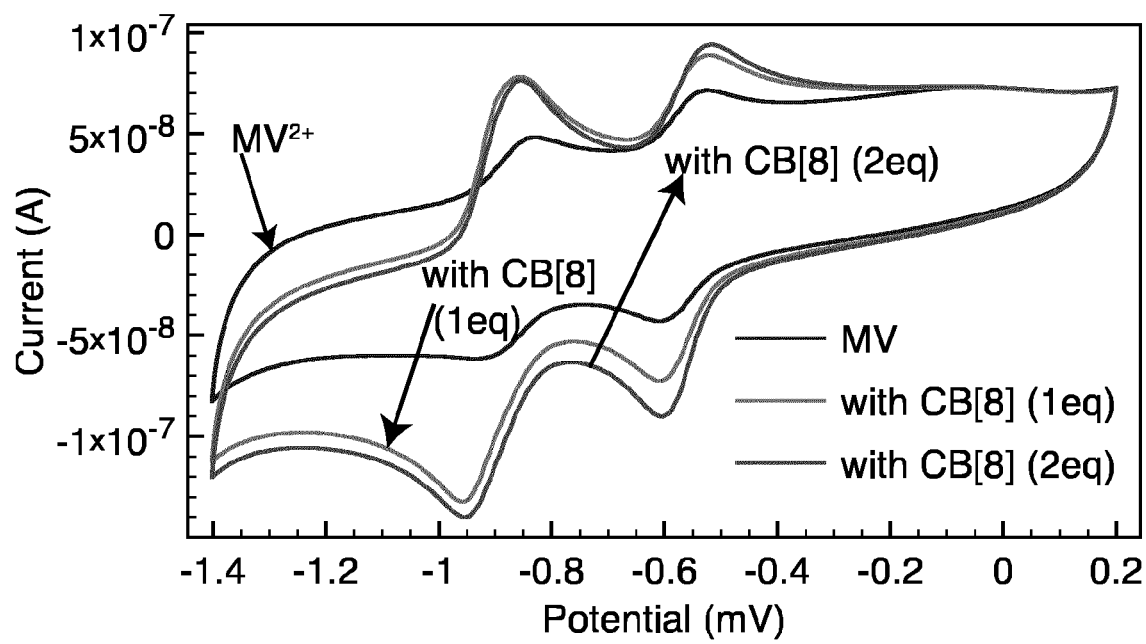
FIG. 6 shows the cyclic voltammogram of MV$^{2+}$ in ChCl-urea DES in the presence of CB[8] with various equivalents of CB[8] (scan rate 50 mV s$^{-1}$). Each sample was run in a 2 mg/mL MV solution in DES. Scans were run from −200 mV to −1400 mV.

It has been found by the present inventors that the $MV^{+\cdot}$ radical is ultrastable in DES without any costly modifications and the electrochemistry of unmodified $MV^{2+}$ was found to be completely reversible and stable over 100 cycles in air. Moreover, the DES can act as an electrolyte itself and all components are cheap, non-toxic and biodegradable thus making this system ideal for the fabrication of an electrochromic device (FIG. 4). Unique to this system, there are four different stimuli that can be used to modulate the colour unlike current chromic devices which typically use only one.

Smart Screens

Smart screens refers to screens wherein at least some of the transparent portion of the screen, for example the glass or glazing, becomes opaque when voltage, light or heat is applied.

In the present invention, the compositions comprising a deep eutectic solvent and a redox-active compound may be used in a smart screen.

At least some of the transparent portion of the screen may become opaque by stimulating a reversible one-electron reduction or oxidation of the redox-active compound. Methods of stimulating the reversible one-electron reduction or oxidation of the redox-active compound are as discussed above.

It may be that additional components are required in order to provide opacity, for example, polymers, coloids or nanoparticles may be added to the composition. Suitable additional component to provide opacity are discussed in Appel et. al. (*J. Am. Chem. Soc.,* 2010, 132 (40), pp 14251-14260; and *J. Am. Chem. Soc.,* 2012, 134 (28), pp 11767-11773), Rauwald et. al. (Angewandte Chemie Int. Ed., Volume 47, Issue 21, May 13, 2008, Pages 3950-3953), and Wu et. al. (PNAS Aug. 1, 2017. 114 (31) 8163-8168).

Sensors

A sensor is a device that can be used to detect a change in an environment, for example the presence of a particular substance, a change in temperature, or exposure to light. Since the reversible one-electron reduction or oxidation of the redox-active compound can be in response to a stimulus (electrochemical, chemical, photochemical, or thermal), the compositions comprising a deep eutectic solvent and a redox-active compound may be used as indicators for a change in such conditions, such exposure to air or oxygen over time.

The composition comprising a deep eutectic solvent and a redox-active compound may be used in a sensor.

In some embodiments, the redox-active compound changes colour upon reduction or oxidation. A redox-active compound which changes colour allows a user to visually inspect whether the change has occurred, for example whether any of the target substance (such as oxygen or other reducing agent) is present by inspecting the colour change of the redox-active compound.

In some embodiments, the compositions comprising a deep eutectic solvent and a redox-active compound may be associated with a carrier and/or encapsulated as further described below. This allows the compositions to be incorporated into tags, labels, or films.

The integration of sensory tags and labels on films, labels or molded parts in and on paper, food packaging, in windows (sensor for thickness of insulating glazing), electronic devices of all kinds allows avoiding damage and loss of quality and indicating the active status of the product. The sensor with colour-changeable sensory surface according to the invention may be part of packaging, films and labels but can also be produced as molded part. Sensors for some products, e.g., food products, pharmaceuticals, medical equipment, electronic devices, or apparel may be time/temperature or time/oxygen indicators and integrators or threshold indicators, which give a visual (optical) signal.

In some embodiments the sensory configuration may be used to display text or symbols by applying the composition in a way that upon a change in environment parts of the sensor change their colour e.g. a test becomes visible or a symbol vanishes. This variant of the sensor may be used for the temporary or permanent display of text and other information.

Alternatively, the sensor may be incorporated into a sensor system such as is described in US 2017/0343471A1, U.S. Pat. No. 8,741,658, and US 2017/0038295A1.

In some embodiments, different compositions of deep eutectic solvent and a redox-active compound are used in the same sensor array. The different compositions may respond to different environmental conditions allow monitoring of more than one condition, for example exposure to oxygen and light. Use of different compositions in the same sensor array that respond differently to environmental conditions over time provides monitoring over time.

Antioxidants and Indicators

The composition comprising a deep eutectic solvent and a redox-active compound may be used as antioxidant.

In the case of a redox-active compound that is capable of undergoing a one-electron reduction to form a radical species the composition is used with the redox-active compound in the radical form. The radical form can react with any oxygen and prevents oxidation.

In the case of a redox-active compound that is capable of undergoing a one-electron oxidation to form a radical species the composition is used with the redox-active compound in the non-radical form. The non-radical form can react with any oxygen and prevents oxidation.

In some embodiments, the redox-active compound changes colour during the reversible one-electron reduction or oxidation process.

When the radical form reacts with oxygen and is oxidised the colour change is observed. This allows a user to visually inspect whether any oxidation has occurred. In this way, the antioxidant properties of the composition comprising a deep eutectic solvent and a redox-active compound may be used as indicator.

The antioxidant properties of the compositions comprising a deep eutectic solvent and a redox-active compound may be adjusted to provide a colour change at a selected time, for example, to indicate freshness or exposure to air after packaging has been opened. In these embodiments, a redox-active compound which changes colour allows a user to visually inspect whether any unwanted oxidation of stored food or other oxygen sensitive product has occurred by inspecting the colour change of the redox-active compound. These embodiments may be useful for indicating the present of oxygen in environments where oxygen is undesired, for example in a glove box or unit for growing bacteria in an anaerobic environment.

In some embodiments, the antioxidant properties of the composition comprising a deep eutectic solvent and a redox-active compound may be used to prevent deterioration of stored food products or other air- or oxygen-sensitive products. For example, the composition reacts with oxygen and prevents oxygen for contacting the stored food products or other air- or oxygen-sensitive products.

In any of these embodiments, the composition comprising a deep eutectic solvent and a redox-active may be adsorbed onto a carrier or into a carrier.

The carrier may be in any suitable form, such as a porous layer, a woven or nonwoven fabric or beads, for example, the carrier may be cellulose, perlite, vermiculite, a polyurethane foam, a polystyrene foam, or other inert matrix.

The composition or composition and carrier may be provided in a gas permeable enclosure, i.e., encapsulated, in a gas permeable material to prevent contact with the food or other oxygen-sensitive product.

When the composition is not associated with a carrier, the gas (oxygen) permeable material is preferably liquid impermeable. Suitable materials are known, for example, certain silicones, polypropylenes, fluorinated ethylene-propylenes, low density polyethylenes, polytetrafluoroethylene, polymethylpentene, amorphous copolymers of perfluoro-2,2-dimethyl-1,3-dioxole (PDD) available as TEFLON AF from Dow DuPont, and copolymers of 2,2,4-trifluoro-5-trifluoromethoxy-1,3-dioxole (TTD) available as HYFLON AD from Solvay Solexis are known materials that are gas permeable and liquid impermeable.

When the composition is associated with a carrier, any suitable material may be used, for example woven or nonwoven fabrics, perforated plastic sheets, and the like.

The composition may be attached to packaging, for example, it may be attached to a lid, or form part of the packaging itself, particularly when encapsulated. Alternatively, the composition may be present in the packaging itself, for example, in a pre-formed holding section in the packaging. In this way, the composition may be useful with a wide variety of oxygen-sensitive products such as food, paints, varnishes, adhesives, polymers, waxes, inks, cleaners, fuels, and others. The composition may act as an antioxidant, an indicator or both.

Since the reversible one-electron reduction or oxidation of the redox-active compound can be in response to other stimuli (electrochemical, photochemical, or thermal), the compositions comprising a deep eutectic solvent and a redox-active compound may be used as indicators for other conditions, as well as exposure to air or oxygen. For example, the compositions alone, associated with a carrier, or encapsulated as described above can be used to indicate exposure to light or heat. In some embodiments the composition may be used as an indicator to indicate exposure to more than one stimulus, for example oxygen and heat or oxygen and light.

Flame Retardant Additive

The compositions comprising a deep eutectic solvent and a redox-active compound may be used as a flame retardant additive.

In the case of a redox-active compound that is capable of undergoing a one-electron reduction to form a radical species the composition is used with the redox-active compound in the radical form. The radical form can react with any oxygen and prevents combustion.

In the case of a redox-active compound that is capable of undergoing a one-electron oxidation to form a radical species the composition is used with the redox-active compound in the non-radical form. The non-radical can react with any oxygen and prevents combustion.

Catalyst

The compositions comprising a deep eutectic solvent and a redox-active compound may be used as a catalyst. When used as a catalyst, the compositions can be absorbed into or onto a carrier as described above.

Agriculture

The present invention provides the use of a composition comprising a deep eutectic solvent and a redox-active compound in agriculture for example as a herbicide or nutritional composition. The use may include spraying of the composition onto an area to be treated.

In the case of use as a herbicide, preferably, the redox active compound in this case is a viologen such as paraquat.

Viologens such as MV are known to be effective herbicides. MV when used as a herbicide is referred to by the name paraquat. Paraquat, when ingested, is highly toxic to mammals, including humans, potentially leading to acute respiratory distress syndrome (ARDS). This limits the potential use of paraquat as a herbicide and paraquat use is restricted or banned in many countries.

It is proposed that the deep eutectic solvent limits or prevents contact between the user (i.e. a human) and the redox-active compound. It is proposed that the deep eutectic solvent provides a form of encapsulation and allows slow release of the redox-active compound. In this way, any toxic effects of the redox-active compound will be limited.

Deep Eutectic Solvents

The present invention makes use of a deep eutectic solvent in a composition together with a host or a redox-active compound.

The deep eutectic solvent may be provided to dissolve the host, for example to allow the host to participate in host-guest chemistries. The deep eutectic solvent may be provided to dissolve or precipitate a host, for example to allow for the purification of the host from other components, such as those components having a different solubility to the host in the deep eutectic solvent.

The deep eutectic solvent may be provided to solubilise the redox-active compound, for example to stabilise the redox-active compound in its radical form.

A deep eutectic solvent is a mixture of components, such as a two component mixture, where the melting point of the solvent is less than the melting point of each of the components. The deep eutectic solvents for use in the present case are typically those that are liquid at a temperature in the range 10 to 90° C., such as 20 to 90° C.

Deep eutectic solvents are well known and have been widely studied.[40-51] A review of deep eutectic solvents is provided by Smith et al. (*Chem. Rev.* 2014, 114, 11060) and Zhang et al. (*Chem. Soc. Rev.* 2012, 41, 7108), which both reference the originating work of Abbott et al. (*J. Am. Chem. Soc.* 2004, 126, 9142), the contents of all of which are hereby incorporated by reference.

A deep eutectic solvent is not an ionic liquid, for example because an ionic liquid has only a discrete anion and cation.

Deep eutectic solvents are seen as providing advantages over other solvent forms, such as ionic liquids for example, for the reason that the deep eutectic solvents are typically environmentally benign, simple to prepare and use, often from readily available and cheap starting materials. The inventors have found that these solvents may be used to together with hosts, including macrocycles such as cucurbituril and cyclodextrins.

A deep eutectic solvent typically comprises an ionic species, which may be referred to as the first component, and a metal salt or hydrogen bond donor species, which may be referred to as the second component. The ionic species may also be referred to as the hydrogen bond acceptor to a hydrogen bond donor species.

The molar ratio of components in the deep eutectic solvent may be selected to provide a mixture that has the lowest melting point, or close to the lowest melting point.

The molar ratio of components in the deep eutectic solvent may be selected to provide a mixture that has the lowest viscosity, or close to the lowest viscosity.

The first component may be present in the deep eutectic solvent together with the second component in a molar ratio of 1:X, where X is the relative mole amount of the second component with respect to 1 mole of the first component, and X is from 0.5 to 5, such as from 1 to 4, such as from 1 to 3, such as from 1 to 4, such as from 1 to 2. The molar ratio of the first component to the second component is typically 1:0.5, 1:1 or 1:2.

It is preferred that the deep eutectic solvent has a freezing point, $T_f$, that is at or close to ambient temperature. However, it is acknowledged that many of the known deep eutectic solvents have a freezing temperature that lies above ambient temperature, such as above 20° C. Thus, the deep eutectic solvent may be provided and/or used at a temperature that is above the freezing point of the solvent.

The deep eutectic solvent may have a freezing temperature that is less than 90° C., such as less than 80° C., such as less than 70° C., such as less than 60° C.

The deep eutectic solvent may have a freezing temperature that is 10° C. or more, such as 20° C. or more, such as 30° C. or more, such as 40° C. or more.

The deep eutectic solvent has a freezing temperature that is less than the melting temperature of a component of the deep eutectic solvent, such as the second component of the deep eutectic solvent. The freezing temperature of the deep eutectic solvent may be at least 10° C., at least 20° C., at least 30° C., at least 40° C., at least 50° C., or at least 60° C. less than the melting temperature of the component.

A deep eutectic solvent may be provided as a liquid. The deep eutectic solvent may be provided or used at a temperature that is above the freezing temperature of the deep eutectic solvent, such as a temperature of 1° C. or more, 5° C. or more, 10° C. or more, 20° C. or more, 50° C. or more above the freezing temperature of the deep eutectic solvent.

Where a deep eutectic solvent is provided as a liquid it may be frozen, if required, by appropriate cooling of the deep eutectic solvent. Similarly, where a deep eutectic solvent is provided as a solid it may be melted, if required, by appropriate heating of the deep eutectic solvent.

The deep eutectic solvent may have a density in the range 1 to 1.7 g cm$^{-3}$, as measured at 25° C., such as a density in the range 1 to 1.5 g cm$^{-3}$, such as 1 to 1.4 g cm$^{-3}$, such as 1 to 1.3 g cm$^{-3}$, such as 1 to 1.2 g cm$^{-3}$.

The deep eutectic solvent may have a viscosity in the range 10 to 100,000 cP, for example as measured at a temperature of 20° C., 25° C., 30° C. or 40° C., such as a viscosity in the range 10 to 50,000 cP, such as 100 to 10,000 cP.

The deep eutectic solvent may have ionic conductivity. The ionic conductivity may be in the range 0.01 to 25 mS cm$^{-1}$, example as measured at a temperature of 20° C. or 40° C., such as an ionic conductivity in the range 0.05 to 10 mS cm$^{-1}$, such as 0.01 to 10 mS cm$^{-1}$.

The ionic species may comprise a cation, such as an ammonium, phosphonium or sulfonium cation, and an anion, which is a Lewis base, such as a halide anion.

The deep eutectic solvent contains, as the second component, a Lewis or Brønsted acid, which may be a metal salt or hydrogen bond donor species.

The second component is preferably a hydrogen bond donor species.

Deep eutectic solvents are categorised into Types I to IV (see, for example, Smith et al.).

A Type I deep eutectic solvent comprises an ionic species, such as those described above, and a non-hydrated metal salt, such as a non-hydrated metal halide, such as a non-hydrated metal chloride. The non-hydrated metal salt metal salt may be a Zn, Sn, Fe, Al, Ga or In salt, such as a halide, such as a chloride. The non-hydrated metal salt metal salt may be a Zn salt, such as $ZnCl_2$.

A Type II deep eutectic solvent comprises an ionic species, such as those described above, and a hydrated metal salt, such as a hydrated metal halide, such as a hydrated metal chloride. The hydrated metal salt may be a Cr, Co, Cu, Ni or Fe salt, such as a halide, such as a chloride.

A Type III deep eutectic solvent comprises an ionic species, such as those described above, and a hydrogen bond donor species, such as urea. A further description of hydrogen bond donor species is given below.

A Type IV deep eutectic solvent comprises a metal salt, such as a metal halide, such as a metal chloride, and a hydrogen bond donor species. The metal salt may be an Al or Zn salt, such as a halide, such as a chloride.

Any type of deep eutectic solvent may be used in the present case, although Type III is preferred.

The first component may be a suitable ionic species. It is preferred that the first component is a quaternary ammonium salt, such as a quaternary ammonium chloride.

The first component may be selected from the group consisting of choline chloride (ChCl), ethylammonium chloride ($EtNH_3Cl$), N-ethyl-2-hydroxy-N,N-dimethylethanaminium chloride, 2-(chlorocarbonyloxy)-N,N,N-trimethylethanaminium chloride, N-benxyl-2-hydroxy-N,N-dimethylethanaminium chloride, tetramethylaminium chloride (TMACl), tetrabutylaminium chloride (TBACl), methyltriphenylphosphonium bromide ($MeP(Ph)_3Br$), methyltriphenylphosphonium chloride ($MeP(Ph)_3Cl$), benzyltriphenylphosphonium bromide, tetraethylaminium bromide (TEABr), tetrabutylaminium bromide (TBABr), 2-hydroxy-N,N,-diethylethanaminium chloride ($Et_2(EtOH)ACl$), 2-chloro-N,N,N-trimethylethanaminium chloride (ClChCl) and acetyl choline chloride (AcChCl).

2-chloro-N,N,N-trimethylethanaminium chloride can be abbreviated to ClChCl or ClACl. The abbreviation ClChCl is used herein.

A first component may be $ZnCl_2$.

The first component is preferably choline chloride. This component is particularly preferred for the reason is unreactive to water, and it is biodegradable and biocompatible (see Zhang et al.). For example, choline chloride is used as a feedstock for chicken food, and it is produced on an industrial scale of this purpose, and others.

The second component may be any suitable hydrogen bond donor. For example, the second component may be selected from the group consisting of urea, p-toluenesulfonic acid (TsOH), acetamide, 1-methyl-urea, 1,3-dimethylurea, 1,1-dimethylurea, imidazole, 2,2,2-trifluoroacetamide, thiourea, benzamide, glycerol, ethylene glycol, malonic acid, benzoic acid, adipic acid, oxalic acid, succinic acid, citric acid, phenylacetic acid, phenylpropionic acid, tricarballylic acid, levulinic acid, itaconic acid, xylitol, sorbitol, tartaric acid, isosorbide, 4-hydroxybenzoic acid, caffeic acid, coumaric acid, cinnamic acid, suberic acid, gallic acid and resorcinol.

The second component is preferably urea, thiourea or p-toluenesulfonic acid, such as urea or p-toluenesulfonic acid, such as urea.

The deep eutectic solvent may be a mixture of choline chloride and urea, or a mixture of p-toluenesulfonic acid and urea.

In one embodiment, a component, such as a functional group, of the deep eutectic solvent may be connected, such as covalently connected, to a polymer. For example, where the deep eutectic solvent contains a quaternary ammonium salt, the quaternary ammonium group may be connected to a polymer.

The present inventions have shown that the resin Amberlite IRA-900 may be used as an alternative to choline chloride in a deep eutectic solvent. The resin possesses N,N,N-trimethyl ethylaminium functionality, with a chloride counter ion.

Each of the first and second components may have a molecular weight that is at least 50, at least 75, at least 100, at least 150, or at least 200.

Each of the first and second components may have a molecular weight that is at most 300, at most 500, at most 1,000, at most 2,000 or at most 5,000.

Each of the first and second components may have a molecular weight that is in a range with the lower and upper limits selected from those given above. For example, each of the first and second components may have a molecular weight that is in the range 50 to 1,000.

The present inventors have found that one of the components of the deep eutectic solvent may be a polymer having suitable functionality for forming a eutectic mixture with a further component. For this reason, the molecular weight of one of the components may be relatively high, such as greater than 1,000, and the advantages of the invention are still accessible with such components.

Methods of Preparation

The compositions of the invention, including those having a host in a complex, may be formed by simple admixture of the various components.

A deep eutectic solvent may be prepared by mixing together the components that make up the solvent, such as the first component and the second component. The components may be heated during the mixing process, for example to a temperature of 80° C. at most, such as 70° C. at most.

The deep eutectic solvent may be prepared prior to the addition of a host or guests, or any other component. Alternatively, one of the components of the deep eutectic solvent may be mixed with a host or guest prior to the addition of the other component.

The deep eutectic solvent may be used in liquid form. The liquid form may exist at temperatures above ambient temperature, therefore heating the components may be required. A composition may be prepared in solid or substantially solid form, and the composition may be heated subsequently to provide the liquid form of the composition.

The relative molar amounts of the first and second components are typically selected to provide a deep eutectic solvent having the most convenient and beneficial properties for use. For example, the mole ratio of components may be selected such as to provide the deep eutectic solvent with the most desirable viscosity.

A composition comprising a deep eutectic solvent and a host may be prepared by mixing the deep eutectic solvent together with the host. The host may be added portionwise or in one batch, as necessary. As noted above, the host may alternatively be mixed with one component of the deep eutectic solvent before the other component is then added.

In some embodiments, the composition of the invention is provided at a temperature above room temperature, such as a temperature up to 80° C. Such a composition may be prepared by pre-heating the deep eutectic solvent to the required temperature, followed by the addition of the host and guest, where present.

Alternatively, the composition may be formed at ambient temperature, by admixture of the components and the composition may then be subsequently heated to the desired temperature.

Where the composition comprises a complex, the composition may be formed from the complexation of the host with one of more guests. The host and the guests may be provided in the composition and they may be permitted to form a complex.

Alternatively, the host-guest complex may be pre-formed, and the complex may be mixed with the deep eutectic solvent. The addition of the complex into the deep eutectic solvent does not disrupt the non-covalent binding of the host with the one or more guests, which therefore allows the complex to remain as such.

The presence of a complex in the composition may be determined analytically, for example by electrochemical analysis and/or UV-vis spectroscopy of the composition. In the worked examples of the present case the presence of a methyl viologen guest in a cucurbituril or cyclodextrin complex was seen from the shift in the redox potential and/or UV/vis absorbance of the guest.

Uses and Methods

In one aspect of the invention there is provided the use of a deep eutectic solvent as a solvent for a host or a solvent for a complex of the host with one or more guests.

Also provided is the use of a deep eutectic solvent to dissolve a host or to dissolve a complex of the host with one or more guests.

The deep eutectic solvent is capable of holding a host within, such as dissolved within it, and allows the host to participate in host-guest chemistries.

A supramolecular complex of a host, such as cucurbituril or cyclodextrin, may be provided or formed in a deep eutectic solvent. The supramolecular complex may be at least partially separated from the deep eutectic solvent by standard purification techniques. For example, a further solvent, such as an organic polar solvent, may be added to the deep eutectic solvent to cause precipitation of the complex. Alternatively, a solvent that is immiscible with the deep eutectic solvent may be used to extract the complex from the deep eutectic solvent. In a further alternative, the deep eutectic solvent may be disrupted, thereby causing the complex to form a precipitate which may be separated from the disrupted deep eutectic solvent. Here, for example, water may be added to the deep eutectic solvent to disrupt the liquid structure of the deep eutectic solvent.

Also provided by the present invention is a method of purifying a host from a component, such as another host. Here, the host has a different solubility in a deep eutectic solvent compared with the other component. For example, one of the host and the other component, such as another host, may be substantially insoluble or sparingly soluble in the deep eutectic solvent.

The method comprises the steps of mixing a composition comprising a host and a component with a deep eutectic solvent, thereby to dissolve one of the host and the component in the deep eutectic solvent, then subsequently separating the other of the host and the component from the deep eutectic solvent, such as by filtration.

The method of the invention may be used to separate one host from another host, such as another form of the host.

The present inventors have found that there are differences in the solubility of cucurbituril compounds in deep eutectic solvents. For example CB[7] has good solubility in a choline chloride-based solvent, whilst CB[6] does not. The solubility of a cucurbituril, such as CB[7], may be used to separate that cucurbituril from insoluble impurities, such as CB[6]. Conversely, the insolubility of a cucurbituril, such as CB[6], may be used to separate that cucurbituril from soluble impurities, such as CB[7].

Similarly, the present inventions understand that there are differences in the solubility of cyclodextrin compounds in deep eutectic solvents. Thus, the deep eutectic solvent may be used to separate cyclodextrin compounds based on the relative solubilities or insolubilities of those cyclodextrin compounds.

The methods of the invention may also be used to separate a host and a component, such as another host, having similar solubilities based on the differences in the solubility of a host whilst in a supramolecular complex. One of the present inventors have previously described the formation of cucurbituril complexes in aqueous mixtures as a way of separating different cucurbituril forms. The methods may be adapted for use in the present case using a deep eutectic solvent as an alternative to water.

The method may comprise the steps of providing a host and a component in a deep eutectic solvent, adding a one or more guests to the deep eutectic solvent, thereby to form a complex of the host with the one or more guests, and subsequently separating the complex from the component.

The complex may be soluble in the deep eutectic solvent. Thus, the formation of complex solubilises the host in the deep eutectic solvent. This allows the separation of the complex, comprising the host, from the component, in situations where the (uncomplexed) host and the component are both insoluble in the deep eutectic solvent.

Conversely, the complex may be insoluble in the deep eutectic solvent. Thus, the formation of complex precipitates the host from the deep eutectic solvent. This allows the separation of the complex, comprising the host, from the component, in situations where the (uncomplexed) host and the component are both soluble in the deep eutectic solvent.

The present invention also provides a method of synthesis. The method comprises the steps of providing a composition comprising a deep eutectic solvent and a host in complex with one or more guests, and reacting the complex. In this reaction the complex may be chemically altered, for example the guest held within the complex may be chemically altered.

An example of a chemical alteration is the reduction or oxidation of a component of the complex, such as the guest. In the worked examples of the present case, a cucurbituril cationic guest participates in an electrochemical redox reaction, yielding a radical neutral of the guest.

A synthesis reaction may be accompanied by a decomplexation of the guest from the host.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

Experimental and Results

Materials and General Methods

All chemicals used were reagent grade or higher and used without further purification unless otherwise stated. CB[n] was synthesised from glycoluril with formaldehyde by a basic procedures published by Day et al. (Day et al., *J. Org. Chem.*, 2001, 66, 8094) and Kim et al. (Kim et al., *J. Am. Chem. Soc.*, 2000, 122, 540). CDs were purchased from Wacker Chemie AG and used without further purification. UV-Vis measurements were carried out using a Cary 400 spectrophotometer.

Choline chloride (ChCl, bioreagent 98%), urea (99%), $d_4$-urea ($CO(ND_2)_2$, 98 atom % D) glycerol (99.5%), ethylene glycol (99%), monoethanolamine (MEA, 99%), trimethylamine (99%), potassium hydroxide (semiconductor grade, 99.99%), $d_3$-iodomethane ($CD_3$-I, 99.5%) and methyl viologen dichloride (98%) were purchased from Sigma Aldrich and used without further purification.

Ferrocene methanol (97%) was purchased from Acros Organics, ammonia (35% aqueous solution) was purchased from Fisher Scientific. $d_9$-choline chloride ($HOCH_2CH_2N(CD_3)_3Cl$) was purchased from QMX laboratories and used without further purification. All aqueous samples were prepared with ultrapure water (Milli-Q®, 18.2 MΩcm). 1H-NMR (400 MHz) were recorded using a Bruker Advance III HD Spectrometer.

CV measurements were recorded on Autolab potentiostat.

UV/Vis spectra were recorded using a Varian Cary 50 UV/vis spectrophotometer with 3 mL, 1 cm path length quartz cuvettes (Hellma) used for all measurements.

EPR Measurements

Electron paramagnetic resonance (EPR) measurements were performed on a Bruker E500 X-band spectrometer with an ER 4122SHQE cavity at a microwave frequency of 9.385 GHz. The external magnetic field was modulated at 100 kHz with an amplitude between 0.05-0.3 mT, depending on the smallest feature in the spectrum, and the spectra were recorded as first harmonics.

The microwave power was chosen between 0.2-2.0 mW, sufficiently small to prevent any saturation of the resonance and concurrent line width broadening. To improve the signal to noise ratio the spectra were averaged over up to 4 scans.

Sample Preparation for EPR Spectroscopy

Preparation of stock solution: $MV^{2+}$ $2Cl^-$ (2.6 mg, 0.01 mmol) was dissolved in ChCl-urea DES (10 mL) to give a 1 mM solution. This was then diluted (1 mL to 9 mL DES) to yield a 0.01 mM solution. Temperature variance: The stock solution was heated to 80° C. then 100° C. and finally 130° C. and held at each temperature for 1 h. Following 1 h at each temperature a sample (~2 mL) was removed and transferred to a Wilmad quartz (CFQ) EPR tube ready for analysis.

Infrared (IR) Spectroscopy

IR spectra were recorded on a Thermo Scientific Nicolet iS50 FT-IR spectrometer. For liquid measurements, a drop of the liquid was placed on the ATR crystal and the spectra recorded using the ATR mode. For gas phase IR measurements, an evacuated IR gas cell (SpecAc, 10 cm path length, equipped with KBr windows) was filled with a sample and a high-resolution transmission spectrum was collected.

Sample Preparation for IR Spectroscopy

A solution of $MV^{2+}$ $2Cl^-$ in ChCl-urea DES (3 mL, 0.39 mM) was added to a glass tube (Chromacol SV-10). The solution was degassed in vacuum, sealed and connected to an evacuated IR gas cell using a Swagelok valve. The solution was heated to the desired temperature for 2 h (80° C., 100° C. or 130° C.) and the valve was opened to transfer the headspace gas to the IR gas cell. The cell was then sealed and transferred to the IR spectrometer for analysis. Reference spectra were obtained in an analogous manner, by adding aqueous $NH_3$ and $NMe_3$ to a sample tube, evacuating the frozen solution in liquid $N_2$ followed by warming to room temperature and transfer of the headspace gas to the IR cell.

Mass Spectrometry (MS)

MS was carried out on a HPR-20 benchtop gas analysis system (Hiden Analytical) with custom-designed microflow capillary inlet to a HAL 101 RC electron impact quadrupole mass spectrometer equipped with a Faraday detector. A sample of the solid mixture (~1.3 g, see below) was placed in a glass tube (Chromacol SV-10) with a stir bar and sealed with a Swagelok valve. The solid was evacuated and connected to the MS sample inlet.

The composition of gases with mass/charge ratios between 2 and 100 amu was analysed while the tube was placed in an oil bath and heated to the desired temperature (80° C., 100° C. or 130° C.).

The following samples were produced from analysis:

HH-DES=ChCl (0.055 mol, 7.750 g) and urea (0.110 mol, 6.664 g)

HD-DES=ChCl (0.055 mol, 7.750 g) and d4-urea (0.110 mol, 7.110 g)

DH-DES=d9-ChCl (0.055 mol, 8.252 g) and urea (0.110 mol, 6.664 g)

DD-DES=d9-ChCl (0.055 mol, 8.252 g) and d4-urea (0.110 mol, 7.110 g)

Synthesis of ChCl-Urea DES

Choline chloride (35.00 g, 0.25 mol, 1 eq.) and urea (30.11 g, 0.5 mol, 2 eq.) were stirred at 80° C. for 30 minutes to 1 hour to form a colourless liquid.

The same synthetic procedure was applied to prepare ChCl-TsOH (using a 2:1 mole stoichiometry).

Synthesis of ChCl-Glycerol DES

Choline chloride (35.00 g, 0.25 mol, 1 eq.) and glycerol (46.05 g, 0.5 mol, 2 eq.) were combined in a vial, sealed and then stirred and heated at 80° C. for 30 min to 1 h to form a colourless liquid.

Synthesis of ChCl-Ethylene Glycol DES

Choline chloride (35.00 g, 0.25 mol, 1 eq.) and ethylene glycol (31.04 g, 0.5 mol, 2 eq.) were combined in a vial, sealed and then stirred and heated at 80° C. for 30 min to 1 h to form a colourless liquid.

Synthesis of Deuterated Methyl Viologen (d6-MV$^{2+}$ 2I$^{-}$)

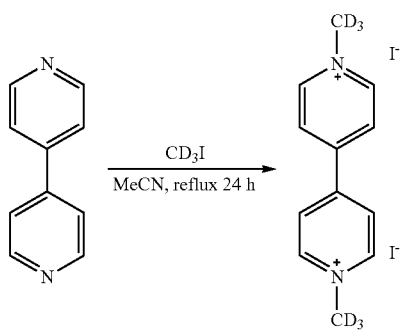

4,4-Bipyridine (250 mg, 1.6 mmol 1 eq) was dissolved in MeCN (5 mL). To this CD$_3$I was added (0.3 mL, 4.8 mmol, 3 eq) and refluxed overnight. Following this a deep red precipitate had formed. The solution was filtered, washed with dichloromethane and dried under high vacuum.

Quantification of Solubility

In general, CDs have much higher aqueous solubility compared to CB[n]. Additionally, the aqueous solubility of each homologue differs in both families, see Table 1.

TABLE 1

Summary of aqueous solubility values of CD and CB[n] macrocycles.

| Macrocycle | Solubility in water (mg/mL) |
|---|---|
| α-CD | 129.5 |
| β-CD | 18.4 |
| γ-CD | 249.2 |
| CB[6] | <0.1 |
| CB[7] | 4.4 |
| CB[8] | <0.2 |

The values for α-, β-, γ-CDs are taken from Sabadini et al. (*Carbohydr. Res*, 2006, 341, 270). The values for CB[n] (where n=6-8) were obtained in this work.

The solubility of α-, β-, and γ-CDs was investigated in ChCl-urea DES. In all cases it was found that CDs were soluble in ChCl-urea DES with enhanced solubilities in comparison to their corresponding aqueous solutions, see Table 2. For α-CD the solubility was >500 mg/mL in ChCl-urea. However, in the case of β-, and γ-CD, the solubility was found to be >1 g/mL, which is approximately a 50 wt % CD solution in ChCl-urea. The solubility enhancement factor in ChCl-urea is greatest for β-CD at >55. It is proposed that the significant enhancement in solubility for CDs arises from the interaction of hydroxyl groups on the CD exterior with the hydrogen-bond network of the DES.

TABLE 2

Table detailing the maximum solubility (mg/mL) of α-, β-, and γ-CD and CB[n] (n = 6-8) in ChCl-urea DES and the enhancement factor relative to aqueous solution.

| Macrocycle | DES solubility mg/mL | Enhancement factor |
|---|---|---|
| α-CD | >500 | >3.5 |
| β-CD | >1000 | >55 |
| γ-CD | >1000 | >4 |
| CB[6] | 1.0 | 10 |
| CB[7] | 17 | 3.9 |
| CB[8] | 2.0 | 10 |

Unlike CDs, values related to the solubility of CB[n]s in different solvation environments is not well documented in the literature. Therefore, the solubility of each CB[n] (n=6-8) homologue in a variety of commonly used media, as well as ChCl-urea DES, has been studied herein, see Table 3.

TABLE 3

Table detailing the maximum solubility (mg mL$^{-1}$) of CB[n] (n = 6-8) in various aqueous media and in two DES.

| | CB[6] | CB[7] | CB[8] |
|---|---|---|---|
| H$_2$O | <0.1 | 4.4 | <0.2 |
| HCl (3M) | 15.0 | 100 | 1.8 |
| NaCl (0.1M) | 4.6 | 14.8 | 0.1 |
| Phosphate buffer (pH = 7.0) | 17.4 | 19.8 | 0.3 |
| ChCl-urea DES | 1.0 | 17.0 | 2.0 |
| ChCl-TsOH DES | 1.0 | 18.0 | 3.1 |

All CB[n] homologues showed a significant solubility enhancement at room temperature in the ChCl-urea DES than in water: CB[7] by almost a factor of 4 (4.4 vs 15 mg/mL) and CB[6] and CB[8] by a factor of 10 (<0.1 vs 1.0 mg/mL and <0.2 vs 2 mg/mL, respectively) in ChCl-urea. It should be noted that the ChCl-urea DES is slightly basic (pH 10 at 20° C.; see [15]) and CB[n] have not been reported previously to exhibit any solubility in basic environments (here CB[5] is soluble at approx. 25 mg/mL).

Additionally, in consideration of the enhanced solubility of CB[n] in acidic media, solubility studies were also conducted on the acidic DES, ChCl-TsOH. Further enhancements in solubility were observed for this solvation media.

Solubility was determined through adding an amount of CB[n] n=6, 7 or 8 or x-CD (where x=α, β or γ) to 1 mL of solvent followed by vortexing and heating the mixture to 80° C. The mixture was inspected visually to determine the presence of undissolved material. The mixture was then cooled to room temperature and the mixture re-examined to determine the presence of any undissolved material.

Probing the Binding Properties of Macrocycles in DES

Investigating the binding properties of macrocycles in DES is not as straightforward as in aqueous environments. For example, the highly ionic nature of the DES prevents the use of $^1$H NMR as an analytical technique. Furthermore, the highly viscous nature of the DES prevents the use isothermal titration calorimetry at room temperature. Consequently, in this work cyclic voltammetry (CV) and UV/vis spectroscopy have been applied to investigate host-guest binding events.

Methylviologen (MV) was chosen as an appropriate guest molecule for these studies for the reasons that it is known to bind to both CD and CB and also has a characteristic profile by UV-visible spectroscopy.

The dicationic form of methylviologen, MV$^{2+}$, is reported to bind 1:1 to both CB[7] (Kim et al., *Proc. Natl. Acad. Sci. U.S.A.*, 2002, 99, 5007 and Ong et al., *Org. Lett.*, 2002, 4, 1791) and CB[8] (Kim et al., *Angew, Chem. Int. Ed.*, 2001, 40, 1526 and Jeon et al., *Chem. Commun.*, 2002, 1828) but does not show any interaction with either β- and γ-CD (Kim et al., *Angew. Chem. Int. Ed.*, 2001, 40, 1526). However, it can reversibly undergo two consecutive one electron reductions to form a monocationic radical species, $MV^{\cdot+}$ or a fully reduced $MV^0$ species.

In aqueous environments the monocationic radical species $MV^{\cdot+}$ is reported to bind 1:1 with CB[7] (Kim et al., *Proc. Natl. Acad. Sci. U.S.A.*, 2002, 99, 5007 and Ong et al., *Org. Lett.*, 2002, 4, 1791) and β-CD (Yasuda et al., *J. Electroanal. Chem.*, 1986, 210, 265) and 2:1 with CB[8] (Jeon et al., *Chem. Commun.*, 2002, 1828) and γ-CD (Yasuda et al., *J. Appl. Electrochem.*, 1987, 17, 567). Therefore, UV spectroscopy was used to probe the behaviour of $MV^{\cdot+}$ in the presence of CDs (β- and γ) and CB[n] (n=7 and 8).

Preparation of MV Solutions for CV Measurements

Methyl viologen dichloride (50 mg, 0.19 mmol) was dissolved in ChCl-urea DES (25 ml) to form a MV stock solution. 1 ml of this MV stock solution was added to a vial containing either CB[7] (9.0 mg, 1.0 eq. or 18 mg, 2 eq.) or CB[8] (10 mg, 1.0 eq. or 20 mg, 2 eq.) in a separate vial. 0.3 ml of this macrocycle-MV solution was diluted with 5 ml of ChCl-urea DES, the solutions were mixed and then measured.

CV Measurements and Results

Cyclic voltammetry was used to investigate a typical redox active guest moiety, namely methylviologen (MV), in solutions of CB[7] and CB[8] in ChCl-urea.

Methylviologen dichloride ($MV^{2+}$ $2Cl^-$) was found to be soluble in ChCl-urea and used throughout. However, it should be noted that other anions, such as $[PF_6]^-$ and $I^-$ were also found to be soluble and may also be used.

As mentioned previously, the dicationic form of methylviologen ($MV^{2+}$) has been widely reported to bind to CB[7]/[8] and form 1:1 inclusion complexes in each instance. It is also known that $MV^{2+}$ in the presence of a reducing agent reduces to $MV^{+\cdot}$, which in aqueous conditions forms a strong 1:1 complex with CB[7] and a strong 2:1 homoternary complex with CB[8]. Additionally, $MV^{+\cdot}$ forms a 1:1 complex with β-CD and a 2:1 complex with γ-CD.

Preparation of MV ChCl-Urea DES Solutions for UV Measurements

CB[7]

Methylviologen dichloride (2.0 mg, 7.8 mmol, 1 eq.) was dissolved in ChCl:urea (1 mL) by vortexing and heating to 60° C. The methylviologen radical was formed by addition of a significant excess of reducing agent, sodium hydrosulfite, approx. 20 molar equivalents. To this solution CB[7] (9.0 mg, 7.8 mmol, 1 eq.) was added and dissolved through stirring at 60° C. A sample of this solution (0.1 mL) was added to ChCl-urea (1 mL) and measured by UV/vis.

CB[8]

Methylviologen dichloride (2.0 mg, 7.8 mmol, 1 eq.) was dissolved in ChCl:urea (1 mL) by vortexing and heating to 60° C. The methylviologen radical was formed by addition of a significant excess of reducing agent, sodium hydrosulfite, approx. 20 molar equivalents. To this solution CB[8] (10.1 mg, 7.8 mmol, 1 eq. or 20.2 mg, 15.6 mmol, 2 eq.) was added and dissolved through stirring at 60° C. 0.1 ml of this solution were added to 1 ml of ChCl-urea and measured by UV/vis.

γ-CD

To probe the binding of γ-CD to $MV^{\cdot+}$ a high concentration of $MV^{\cdot+}$ was required on account of the lower binding constants of CDs compared to CB[n]. A solution of $MV^{\cdot+}$ (15 mg/mL) was prepared (as described for CB[7] above) and to this γ-CD (170 mg, 2 equivalents) was added.

UV-Vis Measurements and Results

As previously mentioned, $MV^{\cdot+}$ forms 1:1 complexes CB[7] and β-CD and 2:1 complexes with CB[8] and γ-CD.

Figure 7:
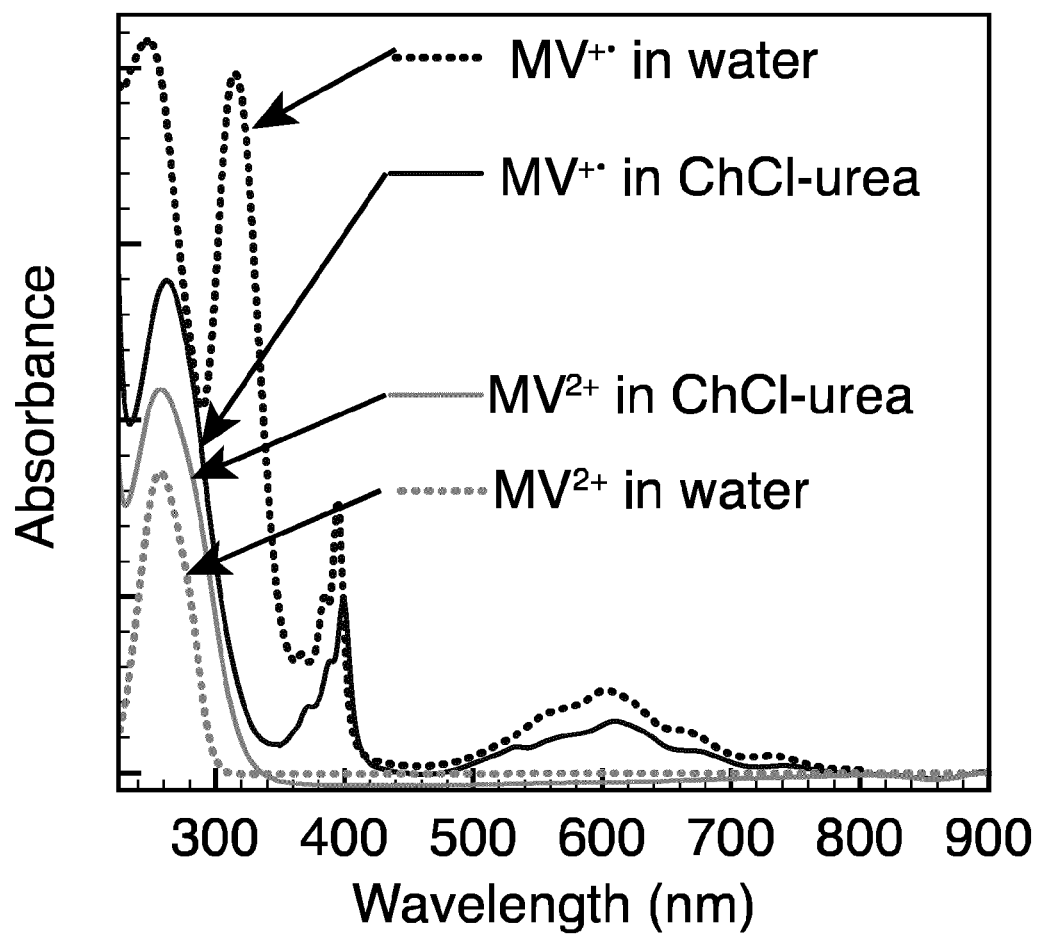
FIG. 7 shows the UV-visible spectra of MV$^{2+}$ and MV$^{+\cdot}$ in water and ChCl-urea DES.
Figure 8:
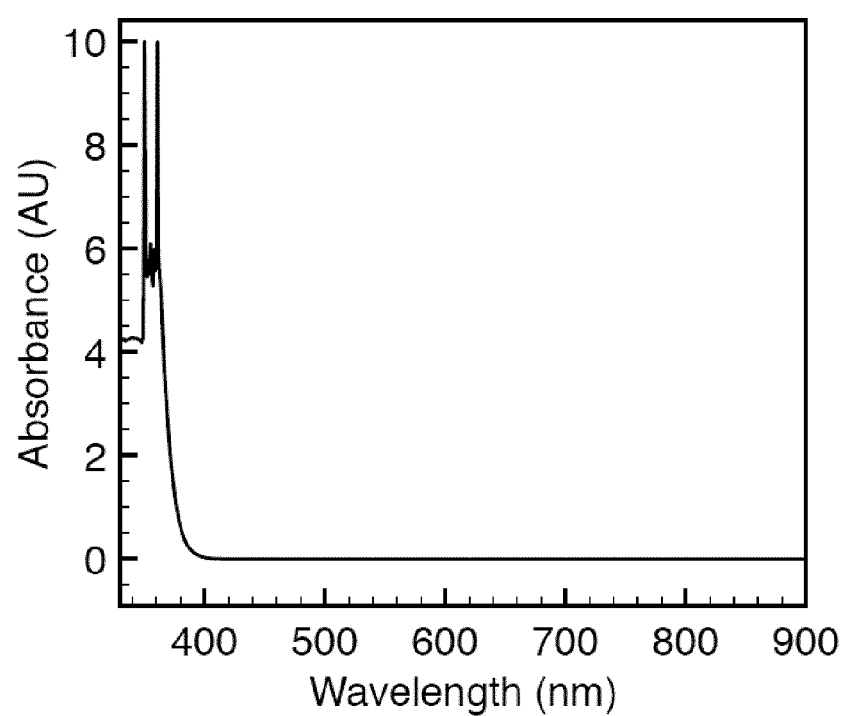
FIG. 8 shows the UV-visible spectrum of sodium dithionate in water showing a significant absorbance at 300-400 nm range.

FIG. 7 shows that the UV-visible profile of methylviologen in DES is similar to that of water. FIG. 8 highlights that the large extra peak (~360 nm) in the spectra corresponding to $MV^{\cdot+}$ arises from the sodium dithionate reducing agent.

Figure 9:
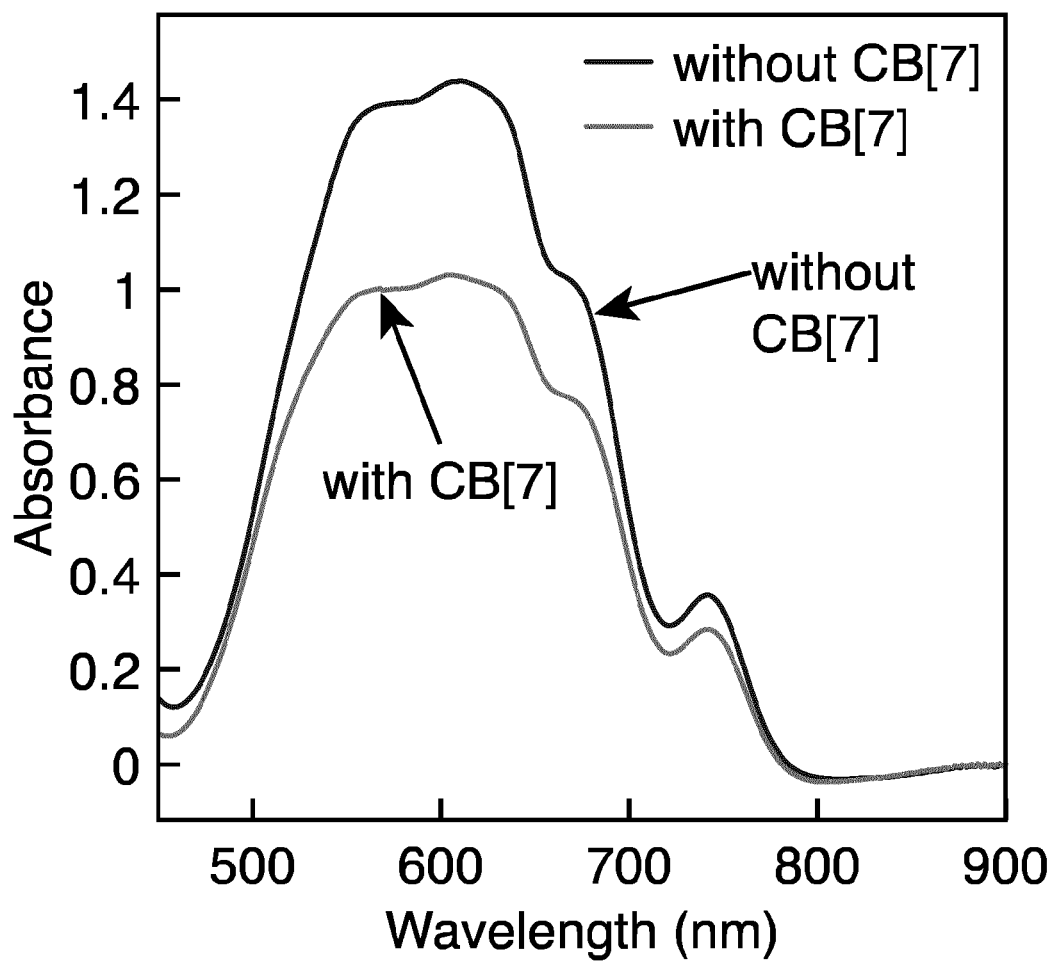
FIG. 9 shows the UV-visible spectrum of MV$^{\cdot+}$ in the absence and presence of CB[7] showing a decrease in intensity at the 609 nm peak.

The 1:1 complexes of $MV^{\cdot+}$ with CB[7] and β-CD in ChCl-urea were studied by UV/vis spectroscopy. For CB[7] a suppression of the absorbance at 609 nm upon the addition of CB[7] was observed (see FIG. 9), which indicates that binding of $MV^{\cdot+}$ is occurring. UV-vis spectroscopy studies could not be conducted upon β-CD as the required concentration of $MV^{\cdot+}$ was too high to obtain a UV/vis spectrum.

Figure 10:
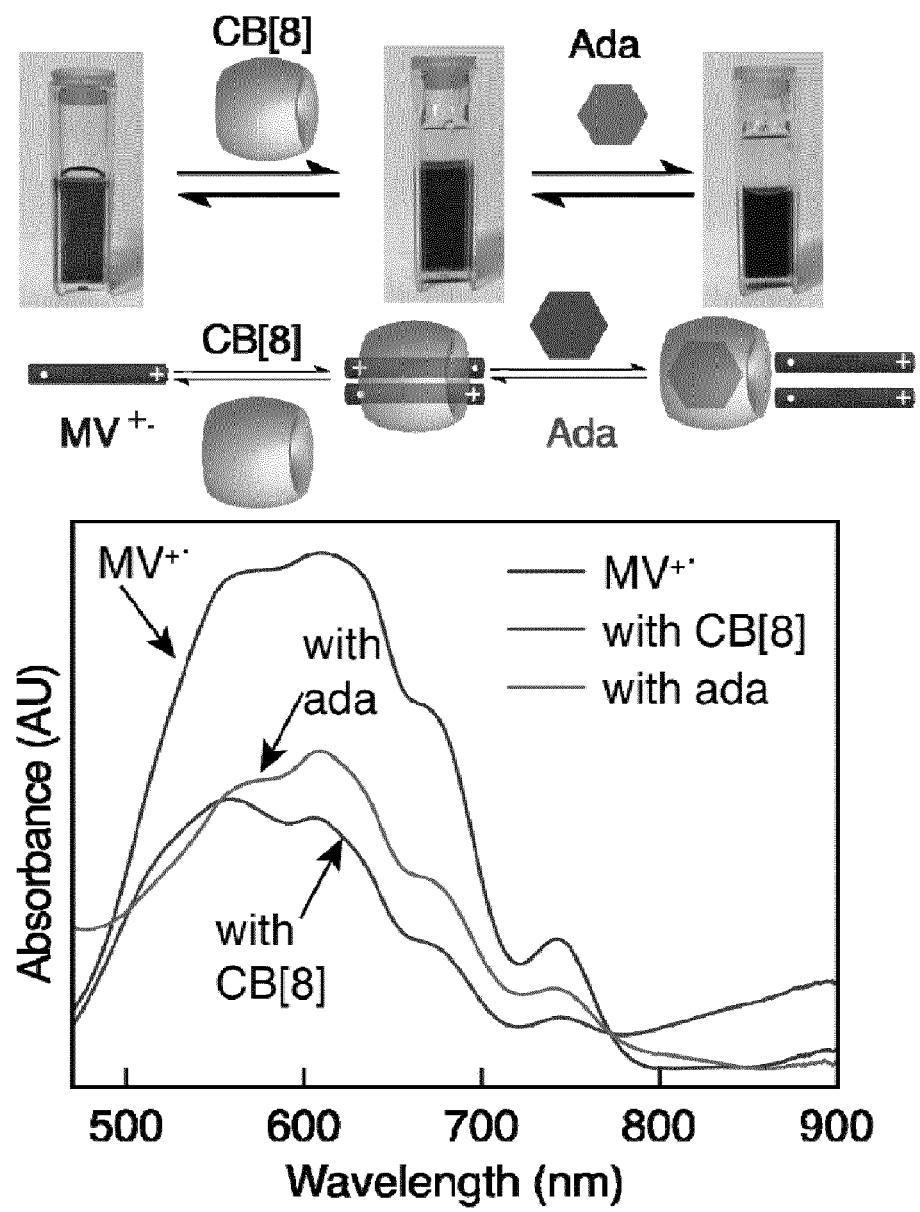
FIG. 10 shows images of vials of MV$^{\cdot+}$, in the presence of CB[8] and upon the addition of Ada (top); a schematic of MV$^{\cdot+}$ in the presence of CB[8] and upon the addition of Ada (middle); and the UV-visible spectra of MV$^{\cdot+}$ in ChCl-urea DES (blue line), in the presence of CB[8] (purple line) and upon the addition of Ada (green line) (bottom).

The 2:1 complexes of $MV^{\cdot+}$ with CB[8] and γ-CD in ChCl-urea were also studied by UV/vis spectroscopy. The introduction of CB[8] to a $MV^{\cdot+}$ solution resulted in a colour change from blue to purple and a pronounced change in the UV-visible spectra (see FIG. 10). This colour change arises from the formation of the $MV^{\cdot+}$ dimer inside the CB[8] (or γ-CD) cavity. Additionally, the $MV^{\cdot+}$ peak at 609 nm decreases in intensity and shifts to 605 nm with concomitant appearance of a peak at 557 nm. This corresponds to the formation of a 2:1 complex.

Furthermore, the addition of a competitive guest for CB[8], namely 1-adamantylamine (Ada), to a solution of $MV^{\cdot+}$ and CB[8] in ChCl-urea results in a red shift of the absorbance seen in UV spectrum. This shift tends towards that of free $MV^{\cdot+}$ (see FIG. 10). This is due to the displacement of the $MV^{\cdot+}$ species from the CB[8] cavity, and thus the CB[8].$(MV^{\cdot+})_2$ complex no longer exists.

Figure 11:
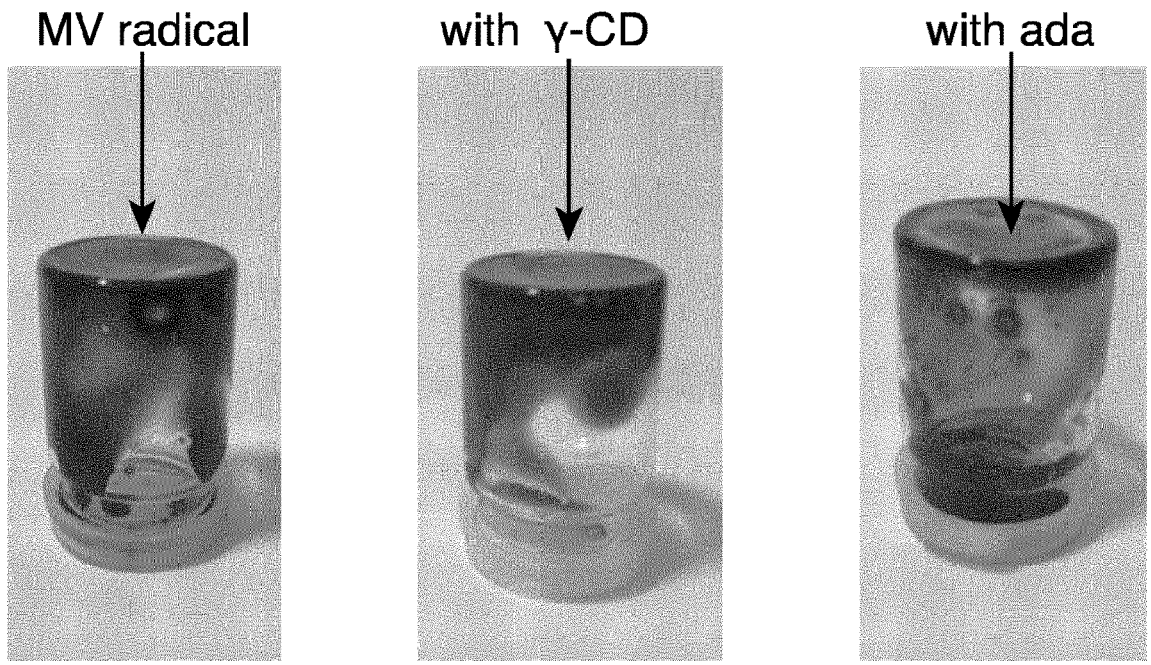
FIG. 11 shows images of vials showing the colour change from blue to purple to blue again showing the formation of a heteroternary complex between MV$^{\cdot+}$ and γ-CD, and displacement by a competitive guest.

An analogous experiment with γ-CD was also conducted. It was seen that binding behaviour similar to the CB[8] system occurred (see FIG. 11). Whereby, on addition of γ-CD a colour change from blue to purple was observed, which was reversed on addition of 1-adamantylamine.

Electrochemical Switching

Figure 12:
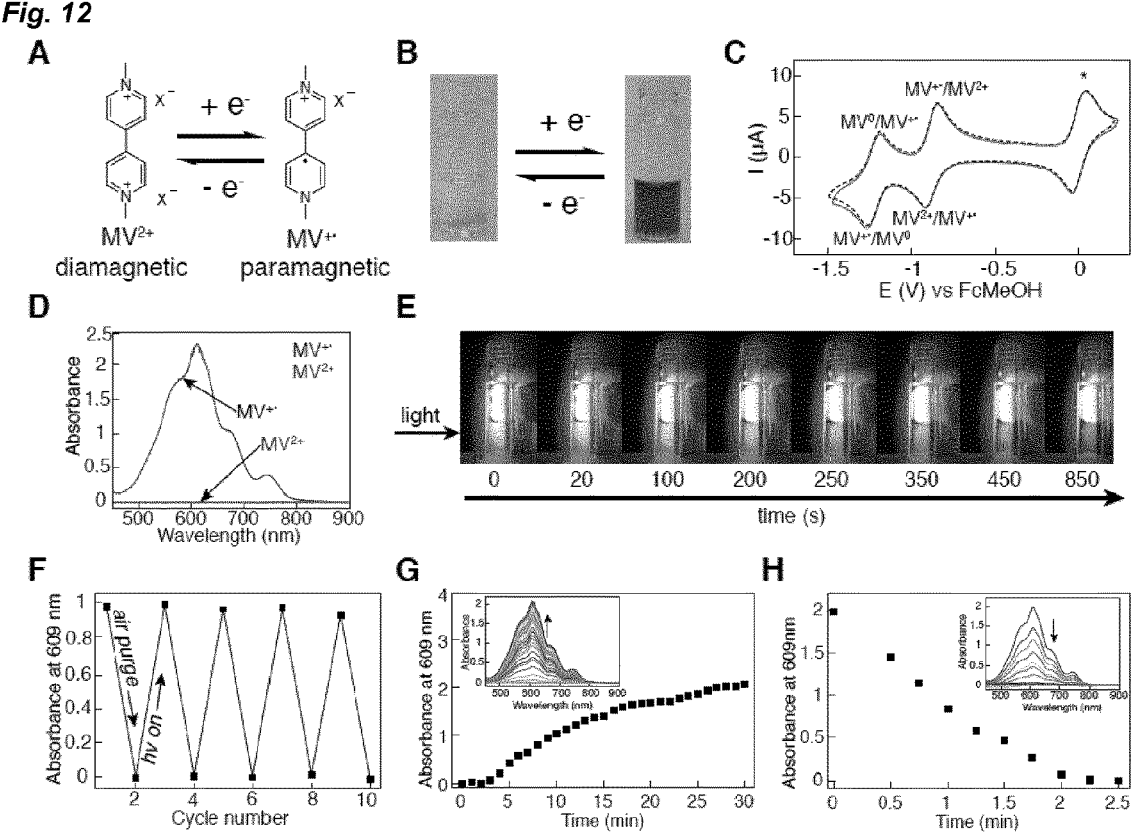
FIG. 12 shows the electrochemical, chemical and photochemical redox behaviour of methyl viologen (MV) in an example DES, ChCl-glycerol. (A) Structural representation of the redox behaviour of MV and changes in magnetic behaviour upon oxidation and reduction. (B) Images of vials showing MV in ChCl-glycerol DES (0.38 mM) in air before and after reduction. (C) Cyclic voltammetry in air of MV in ChCl-glycerol DES (5 mM) showing 2nd cycle (red) and 102nd cycle (black) with FcMeOH as an internal standard. *Denotes the FcMeOH+/FcMeOH couple (glassy carbon working electrode, v=100 mV s$^{-1}$, 40° C.). (D) UV/vis spectra of MV$^{2+}$ in ChCl-glycerol DES (0.39 mM) upon addition of a reducing agent (monoethanolamine) to form MV$^{+\cdot}$ (blue) and following purging with air (red). (E) Photographs depicting the growth of MV$^{+\cdot}$ species (blue) at the interface between the solution and the incident light with time. (F) Photochromic cycling behaviour between MV$^{2+}$ and MV$^{+\cdot}$ in ChCl-glycerol DES. Cycles consisted of photoirradiation with solar light simulator for 5 min following by purging with air for 5 min repeated over multiple cycles. (G) UV/vis spectra showing the formation of MV$^{+\cdot}$ from photoirradiation of MV$^{2+}$ (3.8 mM) in ChCl-glycerol DES with time. (H) UV/vis spectra showing the oxidation of MV$^{+\cdot}$ formed in (G) to MV$^{2+}$ through purging with air (30 mL min$^{-1}$).

MV is a redox active molecule (FIG. 12A) that can undergo a one electron reduction to form an intensely coloured blue solution (FIG. 12B). To determine how solvent nanostructure impacts redox behaviour of MV, we explored the electrochemical response of $MV^{2+}$ in different deep eutectic solvent (DES).

Figure 13:
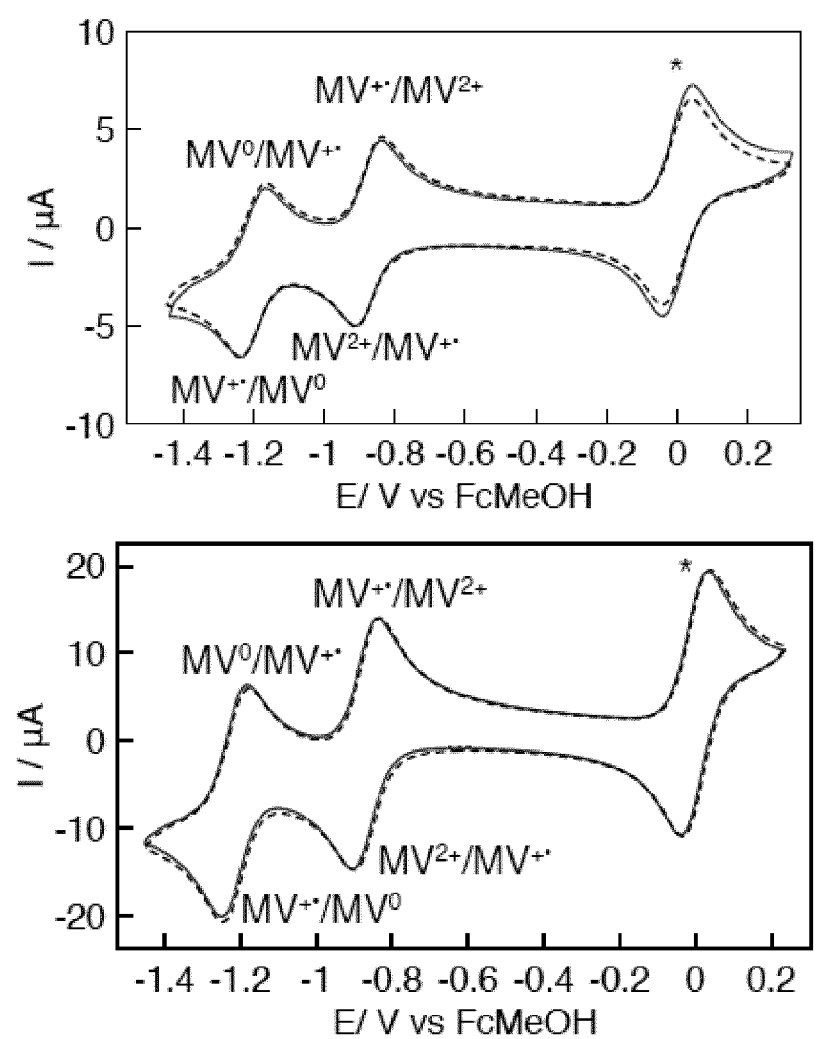
FIG. 13 shows cyclic voltammetry in air of $MV^{2+}$ $2Cl^-$ (5 mM) in ChCl-urea DES (top) and ChCl-ethylene glycol (bottom) showing 2nd cycle (red) and 102nd cycle (black) with FcMeOH (5 mM) as an internal standard. * denotes the FcMeOH+/FcMeOH couple (glassy carbon working electrode, v=100 mV s$^{-1}$, 40° C.).

DES themselves are known to act as electrolytes[52] and therefore all measurements were undertaken using solutions of $MV^{2+}$ in neat DES with hydroxymethylferrocene (Fc-MeOH) as internal reference. Cyclic voltammetry in three typical DES, ChCl-urea, ChCl-ethylene glycol and ChCl-glycerol showed that $MV^{2+}$ could undergo two consecutive one-electron reductions (FIG. 12C, 13) and both processes were fully reversible.

Consecutive cycling between $MV^{2+}$, $MV^{+\cdot}$ and $MV^0$ was performed to demonstrate cycling stability, a key requirement for electrochromic and battery applications.

Remarkably, all DES-MV solutions were found to be stable over 100 cycles with no change in the electrochemical response and no sign of MV degradation. This finding was particularly impressive as the measurements were performed in air without any degassing of the solutions. Such stability in air is unusual for radical cations such as $MV^{+\cdot}$, which are highly reactive towards oxygen, and suggests stabilisation of $MV^{+\cdot}$ in DES environments.

Protocol

Electrochemical measurements were performed in air at 40° C. using a PalmSens EmStat potentiostat. A three-electrode cell was used, equipped with a glassy carbon working electrode (3 mm diameter, BASi), a Ag/AgCl reference electrode (BASi) and a platinum mesh counter electrode (Sigma-Aldrich). The working electrode was cleaned before experiments by mechanically polishing in alumina (Buehler, Micropolish, 1 µm) on a polishing cloth (Buehler, Microcloth).

Cyclic voltammetry (CV) was recorded at 0.1 V s$^{-1}$ scan rate and 5.0 mM MV$^{2+}$ 2Cl$^-$ concentration. FcMeOH (5 mM) was used as an internal reference. Analyte solutions were prepared by heating the respective DES with MV$^{2+}$ 2Cl$^-$ and FcMeOH to 80° C. for 30 min.

None of the solutions were degassed before measurement nor was any attempt made to exclude oxygen or air.

Chemical Switching

Figure 14:
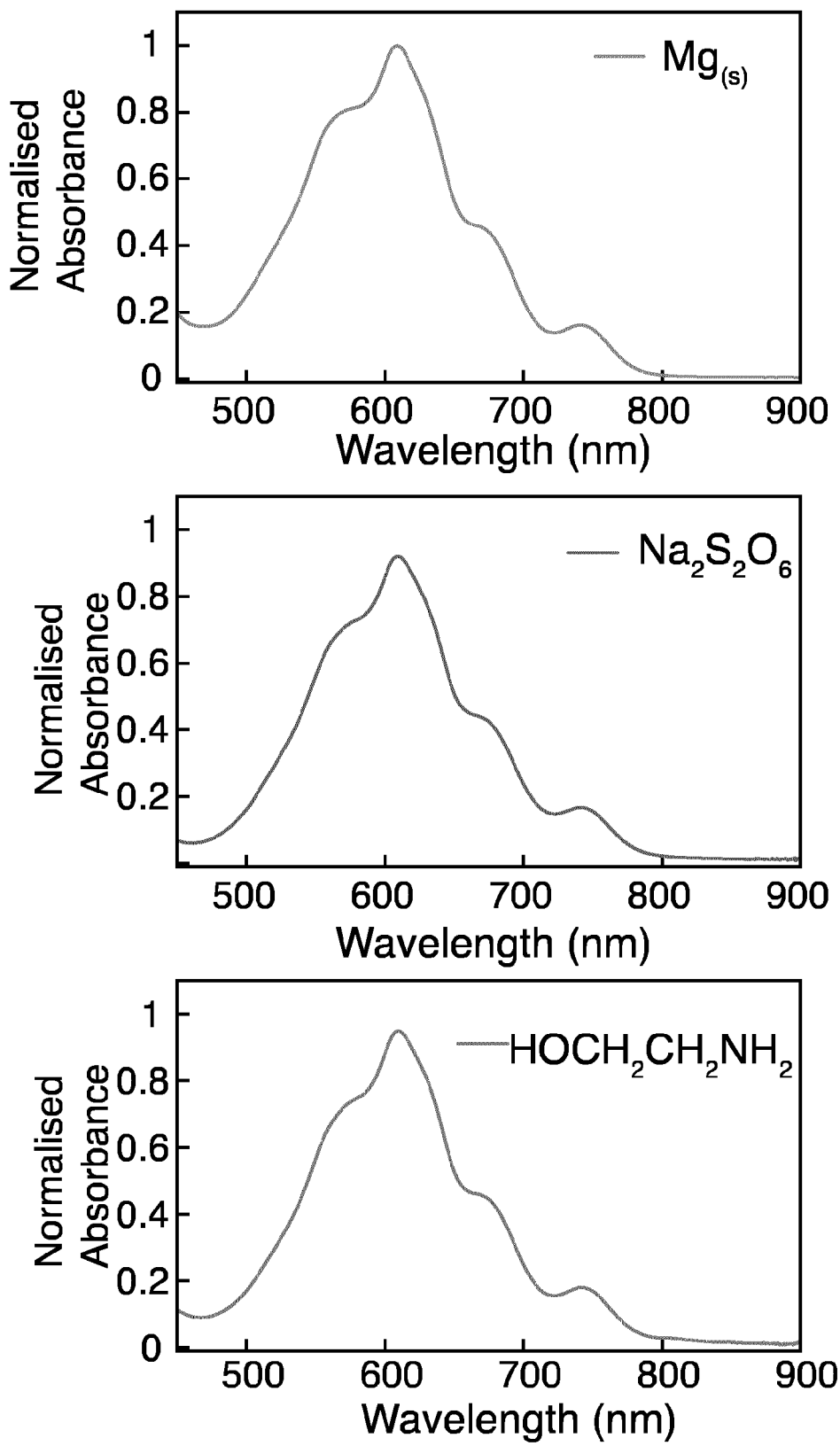
FIG. 14 shows UV/vis spectra of $MV^{2+}$ in ChCl-urea DES (0.39 mM) upon addition of excess reducing agent (top to bottom: Mg(s), $Na_2S_2O_8$, MEA) to form $MV^{+\cdot}$. Solutions were prepared and measured in air without purging.
Figure 15:
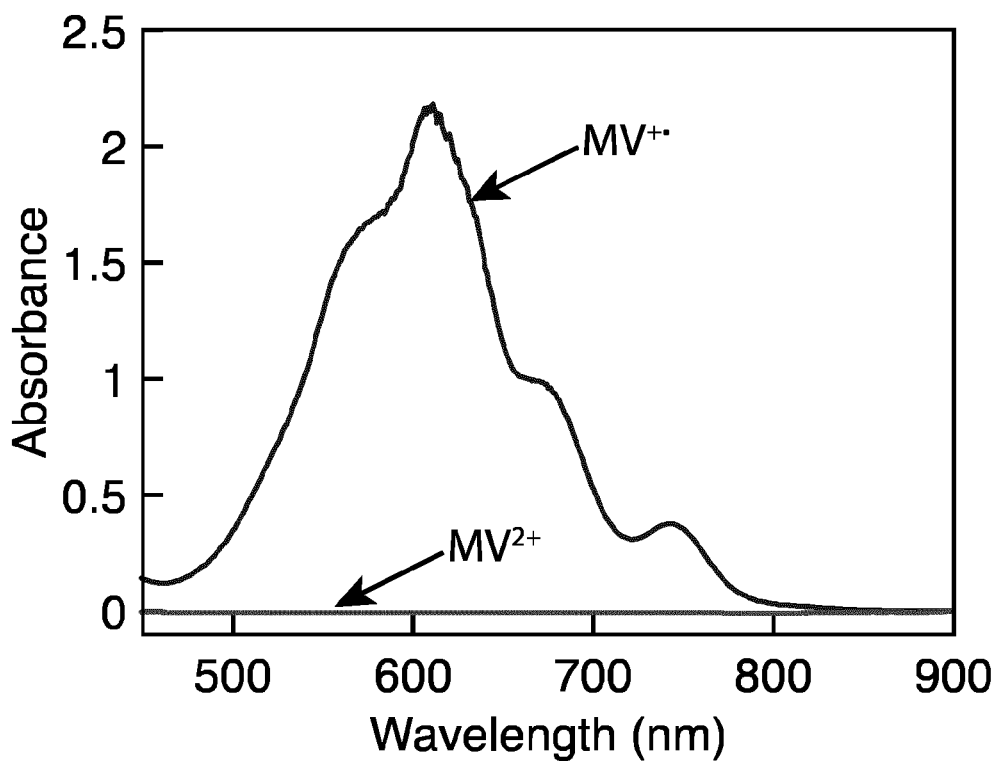
FIG. 15 shows UV/vis spectra of $MV^{2+}$ in ChCl-urea DES (top) and ChCl-ethylene glycol (bottom) (0.39 mM) upon addition of a reducing agent (MEA, 90.5 µL) to form $MV^{+\cdot}$ (blue) and following purging with air (30 ml min$^{-1}$) to re-oxidation to form $MV^{2+}$ (red). Solutions were prepared and measured in air without purging.
Figure 15:
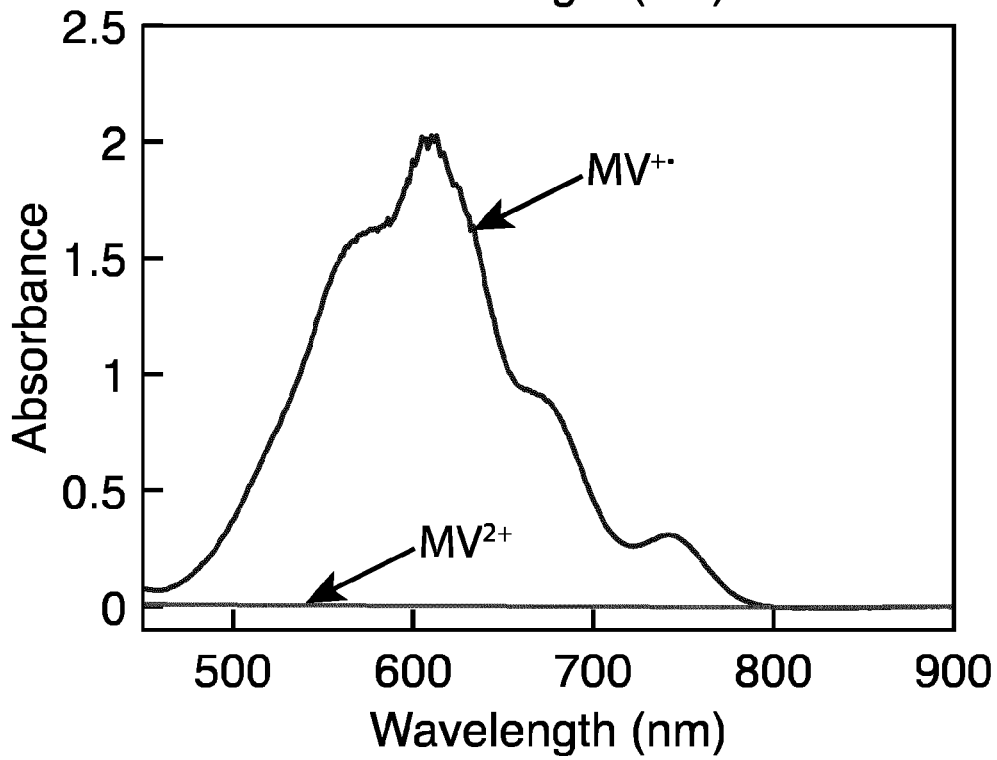

Switching between MV$^{2+}$ and MV$^{+\cdot}$ using a chemical stimulus was investigated through monitoring the optical properties upon addition of different reducing agents (FIG. 14). A visible colour change from colourless to an intense blue was observed, indicating the formation of the MV$^{+\cdot}$ radical cation with a characteristic UV/vis spectrum (λmax=399 nm and 609 nm). To re-oxidise MV$^{+\cdot}$ to MV$^{2+}$ solutions were bubbled with air to introduce O$_2$ into the system and quench the radical. When purged with air the blue colour slowly faded and the solution reverted to colourless, this was associated with the loss of all absorption between 300-800 nm (FIG. 12D, 15).

Protocol

MV$^{2+}$ 2Cl$^-$ (10 mg, 0.039 mM) was added to DES (10 mL) and dissolved by heating to 80° C. for 30 min (3.9 mM). Upon dissolution, a UV/vis spectrum was recorded for each DES solution.

None of the solutions were degassed nor was any attempt to keep oxygen or air out and all measurements were carried out in air.

Reduction of MV$^{2+}$ to MV$^{+\cdot}$

To 1.5 mL of these solutions an excess of reducing agent, monoethanolamine (MEA) (90.5 µL,) was added and the solutions turned blue. UV/vis spectra of the resulting solutions were recorded.

Oxidation of MV$^{+\cdot}$ to MV$^{2+}$

After measuring the solutions, air was bubbled through each one (30 ml min$^{-1}$ for 5 min) and the solutions turned from blue to colourless and the UV/vis spectra were recorded.

Photochemical Switching

Figure 16:
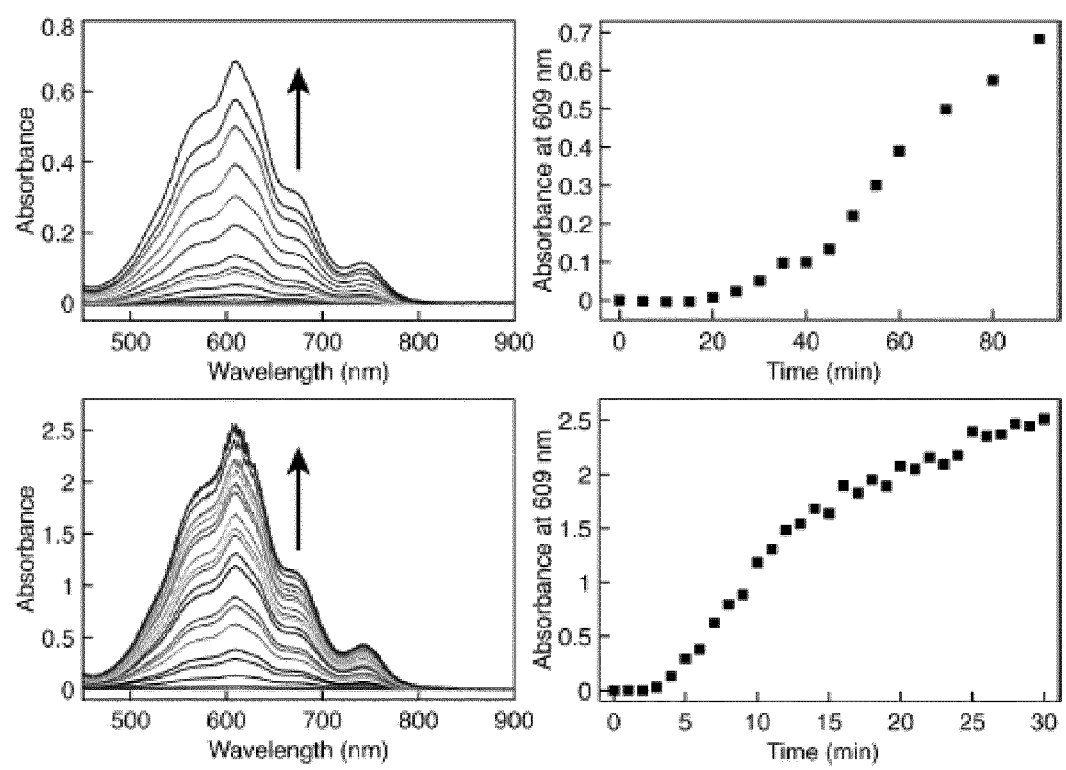
FIG. 16 shows UV/vis spectra (left) and plots of absorbance at 609 nm with time (right) showing the formation of $MV^{+\cdot}$ from photoirradiation of $MV^{2+}$ (0.38 mM) in two DES ChCl-urea (top) and ChCl-ethylene glycol (bottom). Spectra were acquired over a 90 min period (1 spectrum every 5 min) for ChCl-urea and a 30 min period (1 spectrum every min) for ChClethylene glycol. Solutions were prepared and measured in air without purging.

The photochromism of MV in three different DES was probed using simulated solar light (AM 1.5 G, 100 mW cm$^{-2}$). Upon irradiation, the colourless MV$^{2+}$ solution turned blue, indicative of MV$^{+\cdot}$ generation, which was confirmed by its characteristic absorbance in the UV/vis spectrum (FIG. 16). The radical was observed to originate at the interface of the solution with the incident light forming a blue layer that gradually grew into the solution over time (FIG. 12E). Visualisation of this process in real time highlights the unique way in which the MV$^{+\cdot}$ species is held within the nanostructure of the DES. Remarkably, no difference was observed whether photoreduction experiments were performed under aerobic or anaerobic conditions.

Figure 17:
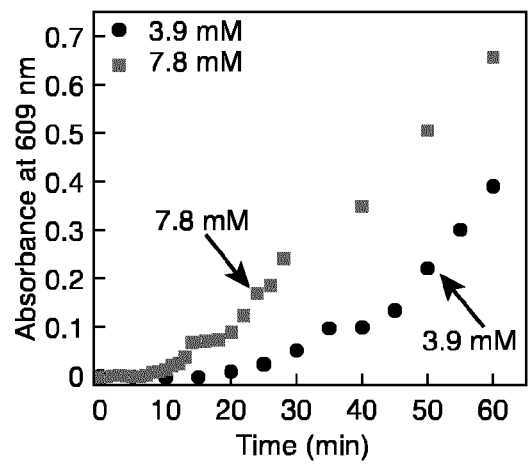
FIG. 17 shows plots of change in absorbance at 609 nm (indicative of the formation of $MV^{+\cdot}$) with time during the photoirradiation of $MV^{2+}$ in three different DES (top to bottom, ChCl-urea, ChCl-glycerol and ChCl-ethylene glycol) at different $MV^{2+}$ concentrations. Solutions were prepared and measured in air without purging.
Figure 17:
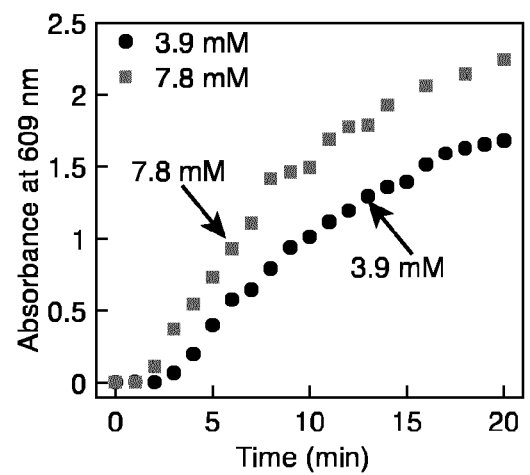
Figure 17:
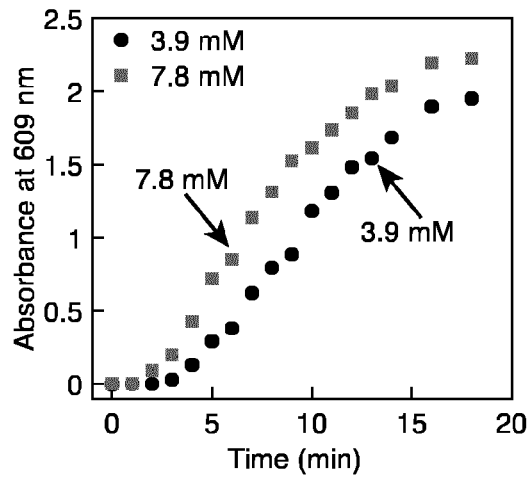
Figure 18:
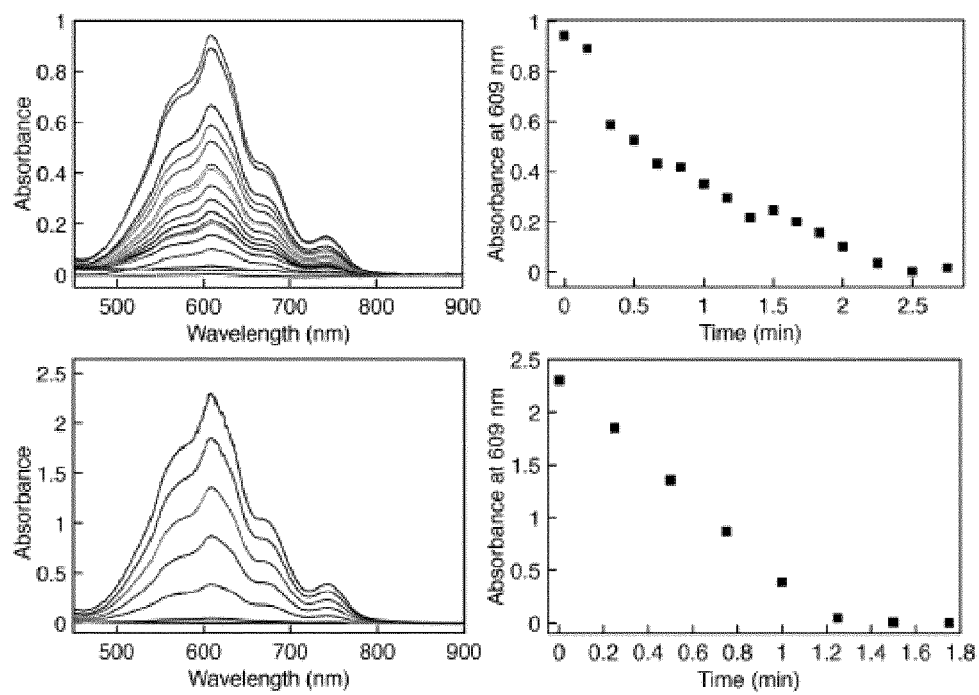
FIG. 18 shows UV/vis spectra (left) and plots of absorbance at 609 nm with time (right) showing the oxidation of $MV^{+\cdot}$ (0.38 mM) produced from photoirradiation (FIG. 16) upon purging with air (30 ml min$^{-1}$) in two DES ChCl-urea (top) and ChCl-ethylene glycol (bottom).
Figure 19:
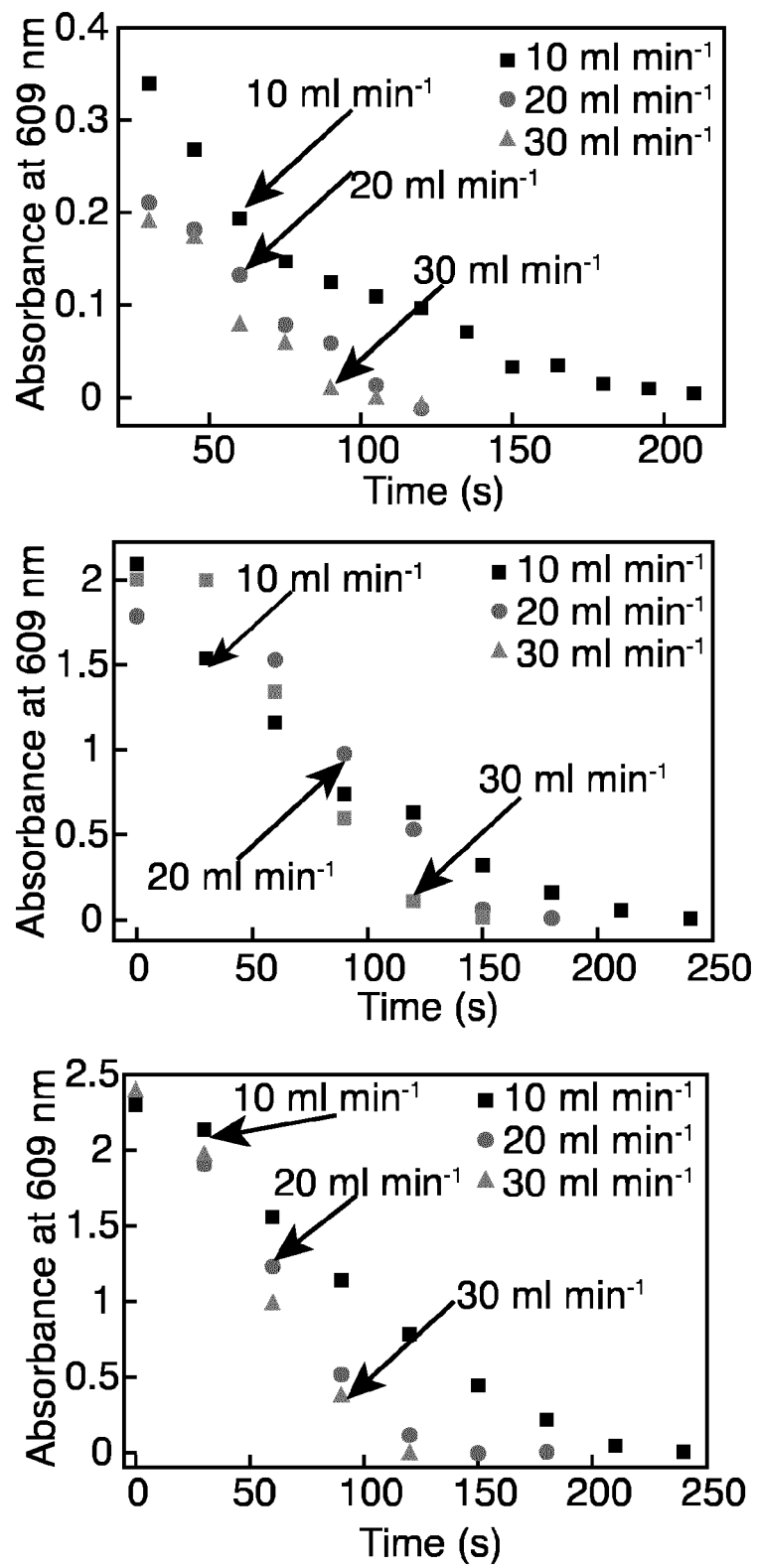
FIG. 19 shows plots showing the change in UV/vis absorbance at 609 nm (indicative of $MV^{+\cdot}$) with time during purging of MV.+ solutions (0.38 mM) formed through photoirradiation (FIG. 12G, 16) in three different DES (top to bottom, ChCl-urea, ChCl-glycerol and ChCl-ethylene glycol) with different purging rates.

Moreover, the resulting MV$^{+\cdot}$ solutions were stable in air with measurements taken over several hours open to air without further irradiation showing no detectable loss of absorbance at 609 nm in the UV/vis spectrum. This suggested that the MV$^{+\cdot}$ was not being quenched by atmospheric O2 indicating again that the DES have a stabilising effect. It was found that a MV solution could undergo multiple cycles of photoirradiation and purging without any impact on performance (FIG. 12F). The rate of photochromic coloration could be tuned by varying the nature of the DES (FIG. 12G, 16). For alcohol-based DES (ChCl-ethylene glycol and ChCl-glycerol) the formation of MV$^{+\cdot}$ was faster compared to amide-based ChCl-urea DES under the same conditions. It is proposed that this is a result of the photoreduction mechanism as alcohols are known to rapidly quench the MV$^{2+}$ excited state with formation of MV$^{+\cdot}$.[55] The rate of MV$^{+\cdot}$ formation could be further controlled by varying the MV$^{2+}$ concentration (FIG. 17). Decolouration of MV$^{+\cdot}$ solution was achieved by purging the solution with air (FIG. 12H, 18) with the rate of decolouration dependent on gas flow into the solutions (FIG. 19), all solutions reverted to colourless within 150 s.

Protocol

DES MV$^{2+}$ solution (1.5 mL) in a quartz cuvette (1 cm path length, Hellma) was placed in a water bath held at 25° C. and irradiated by a solar light simulator (Newport Oriel, 100 mW cm$^{-2}$) equipped with an air mass 1.5 global filter (AM 1.5 G). IR irradiation was filtered with a water filter (10 cm path length). Samples were thermostatted at 25° C.

Stock solutions of MV$^{2+}$ in each of the three DES were prepared as follows: MV$^{2+}$ 2Cl$^-$ (10 mg, 0.04 mmol) was added each individual DES (ChCl-urea, ChCl-glycerol and ChCl-ethylene glycol) (10 mL) separately and dissolved by heating to 80° C. for 30 min to give a colorless solution.

Reduction of MV$^{2+}$ to MV$^{+\cdot}$

MV$^{2+}$ in DES (1.5 mL) was transferred to a quartz cuvette and placed in a water bath held at 25° C. in front of a solar light simulator. The sample was removed from the simulator and UV/vis spectra recorded at various time intervals to monitor the formation of MV$^{+\cdot}$.

Oxidation of MV$^{+\cdot}$ to MV$^{2+}$

The resultant blue MV$^{+\cdot}$ solutions were then purged with air (30 mL min$^{-1}$) using a mass flow controller (Brooks). UV/vis spectra were recorded at time intervals during the purging to monitor the disappearance of the MV$^{+\cdot}$ species.

Cycling Between MV$^{2+}$ and MV$^{+\cdot}$

MV$^{2+}$ in ChCl-glycerol DES (1.5 mL, 7.8 mM) was placed in a quartz cuvette. One cycle consisted of the following: the cuvette was transferred to the solar light simulator for 5 min.

The sample was then removed and a UV/vis spectrum obtained. The solution was purged with air (5 min, 30 mL min$^{-1}$) and another UV/vis spectrum was measured.

Thermal Switching

Figure 20:
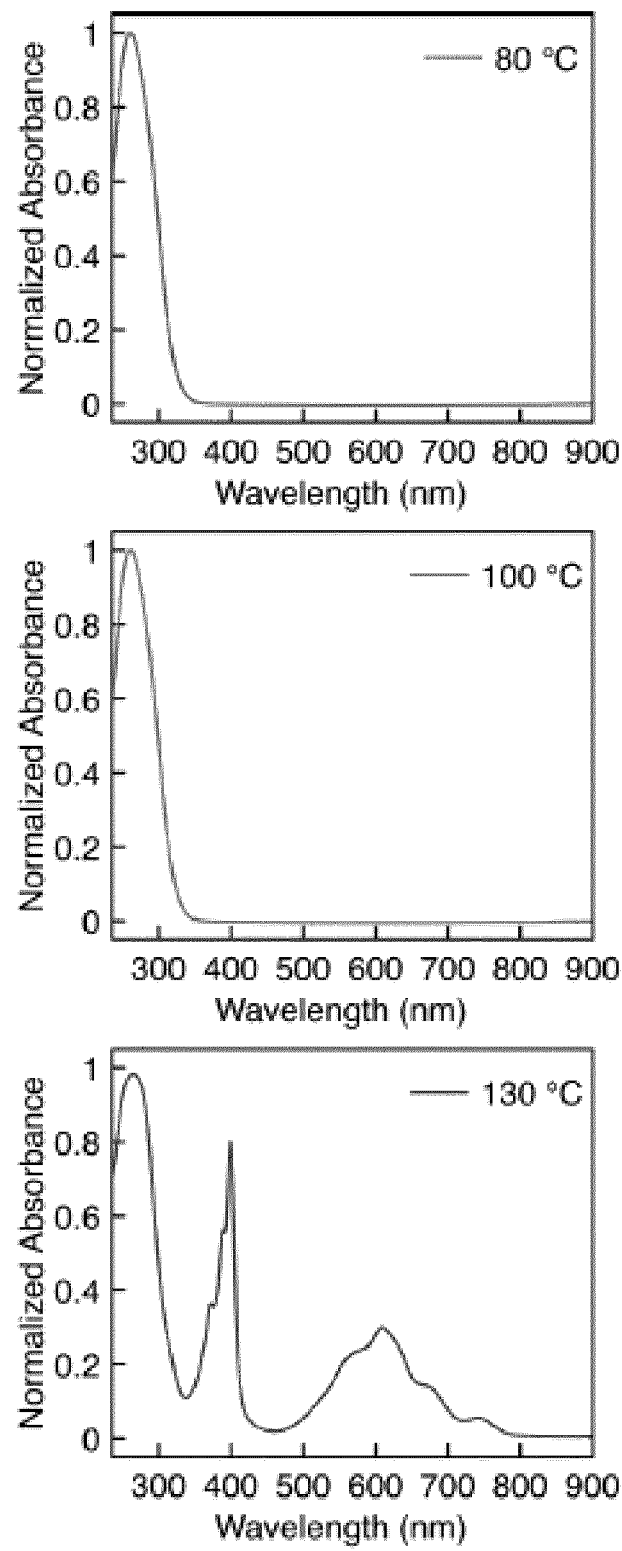
FIG. 20 shows effect of temperature on UV/vis spectra of ChCl-urea DES with $MV^{2+}$ (0.39 mM) (top, A) at 80° C. (middle, B) at 100° C. (1 h) (bottom, C) at 130° C. (1 h). Solutions were prepared and measured in air without purging.
Figure 21:
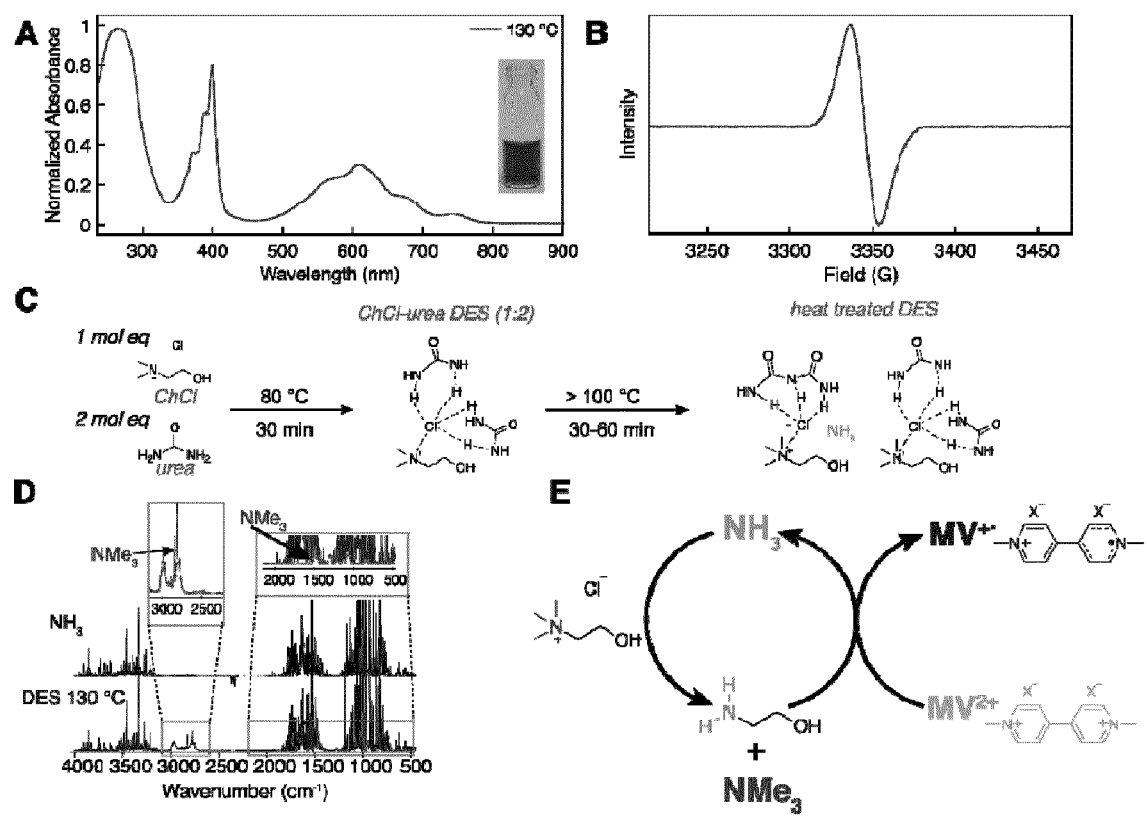
FIG. 21 shows thermal switching of MV in ChCl-urea DES. (A) UV/vis spectra of $MV^{+\cdot}$ in ChCl-urea DES following heating of $MV^{2+}$ solution to 130° C. Spectrum shows characteristic $\lambda$max=399, 609 nm (inset: photo of $MV^{+\cdot}$ solution). (B) EPR spectrum of $MV^{+\cdot}$ in ChCl-urea DES (1 mM) formed through thermal stimulus. (C) Schematic depicting the formation of DES and structural changes following thermal treatment. (D) Gas-phase IR spectra of ChCl-urea DES heated to 130° C. (blue), reference spectrum of $NH_3$ (black). Zoom inset shows 2500-3000 cm$^{-1}$ and 2000-1000 cm$^{-1}$ regions, heated DES (blue) and NMe3 reference (red). (E) Proposed mechanism for $MV^{2+}$ reduction induced within ChCl-urea DES upon introduction of a thermal stimulus.

In order to employ heat as a stimulus, we made use of a thermal phenomenon unique to ChCl-urea DES. Thermochromism was studied by monitoring the UV/vis spectrum of a solution of MV$^{2+}$ in ChCl-urea DES as a function of temperature (FIG. 20). Heating to 130° C. for 30 min in air resulted in a blue solution with characteristic absorbances at λ=399 and 609 nm, consistent with the formation of MV$^{+\cdot}$ (FIG. 21A).

Figure 22:
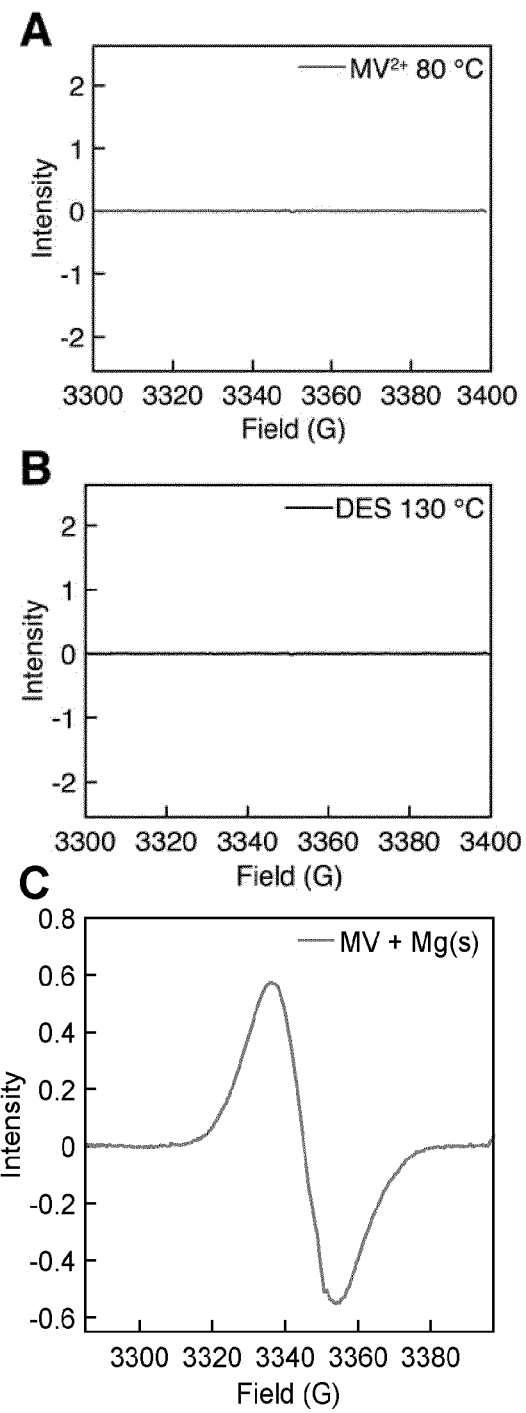
FIG. 22 shows EPR spectra of (A) ChCl-urea DES heated to 80° C. (1 h) in the presence of $MV^{2+}$ (0.01 mM) and (B) ChCl-urea DES heated to 130° C. (1 h) in the absence of $MV^{2+}$. (C) $MV^{2+}$ in ChCl-urea DES following chemical reduction. Solutions were prepared by dissolving MV (0.01 mM) in the presence of Mg(s) as a reducing agent at 80° C. (1 h). All Mg(s) was filtered off prior to the solution being transferred to the EPR tube for measurement. All solutions were prepared and measured in air without purging.

The presence of the paramagnetic MV$^{+\cdot}$ radical was further corroborated by EPR spectroscopy. At 80° C. the spectrum was EPR-silent (FIG. 22A) however, upon heating to 130° C., a strong EPR signal appeared (FIG. 21B) indicative of the paramagnetic MV$^{+\cdot}$ radical cation. Control spectra of ChCl-urea DES heated to 130° C. in the absence of MV$^{2+}$ (FIG. 22B) were found to be EPR-silent showing the paramagnetic species is not a result of solvent degradation. Moreover, the EPR spectra of the thermally reduced MV$^{2+}$ was analogous to that of a chemically reduced species, FIG. 22C. Radical formation was similarly observed in other DES when a catalytic amount of urea was added.

Detailed mass spectrometry (MS) and gas-phase infrared spectroscopy (IR) experiments were carried out to elucidate the mechanism. In both the MS and IR spectra the formation of NH$_3$ was observed upon heating ChCl-urea DES to 100°

Figure 23:
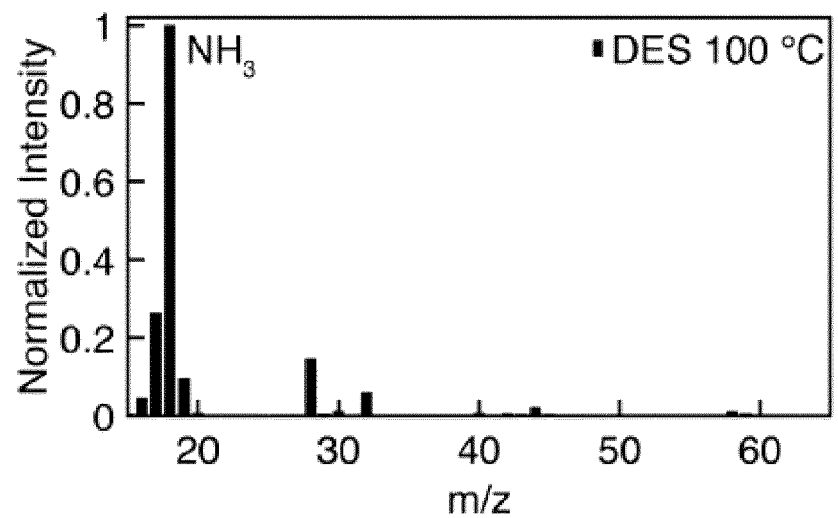
FIG. 23 shows an MS spectrum of ChCl-urea DES heated to 100° C. showing the formation of ammonia ($NH_3$, m/z=17).
Figure 24:
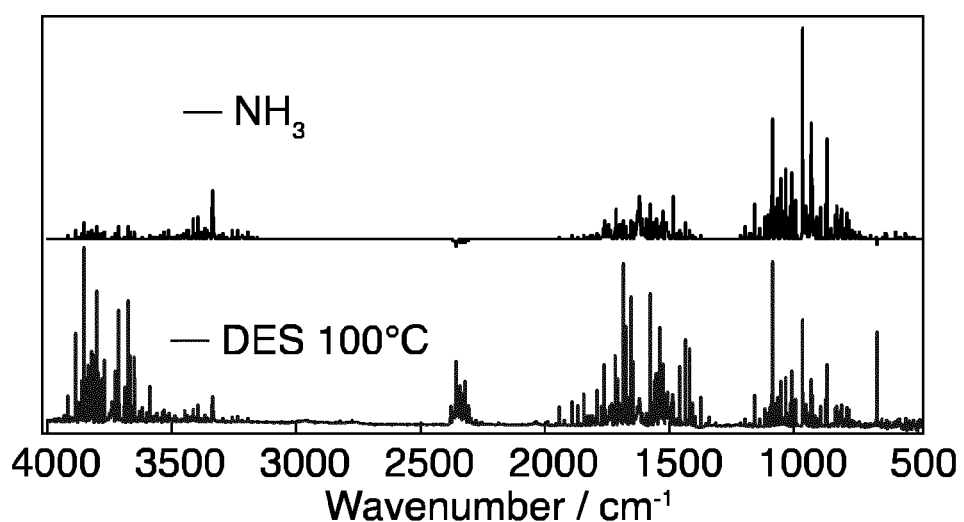
FIG. 24 shows a gas-phase IR spectra showing the formation of $NH_3$ from ChCl-urea following heating to 100° C. (bottom) and control spectrum of neat $NH_3$ (top).

C. (FIG. 21C, 23-24). Upon further heating to 130° C., NH$_3$ was still observed, however, in both the IR and MS spectra (FIG. 21D, 25) additional peaks appeared, which were identified as trimethylamine (TMA) (FIG. 21D, 26).

This suggested that NH$_3$ was involved in the formation of TMA.

To further probe the underlying mechanism, four deuterated DES variants were prepared. These had either no deuteration (HH-DES), deuteration of ChCl (DH-DES), deuteration of urea (HDDES) or deuteration of both components (DD-DES).

Figure 25:
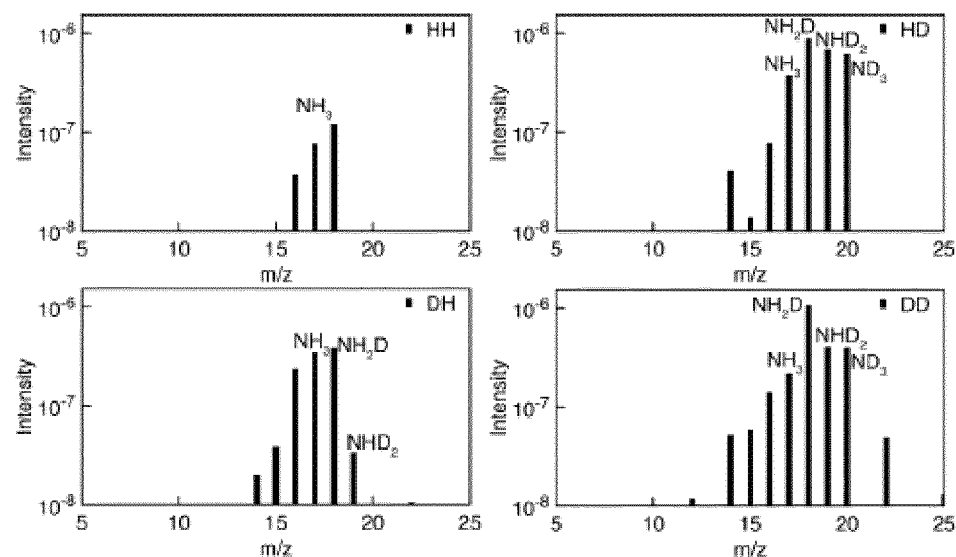
FIG. 25 shows an MS spectra showing the ammonia ($NH_3$) species formed in different labelled ChCl-urea DES (HH, HD, DH and DD) upon heating to 130° C.
Figure 26:
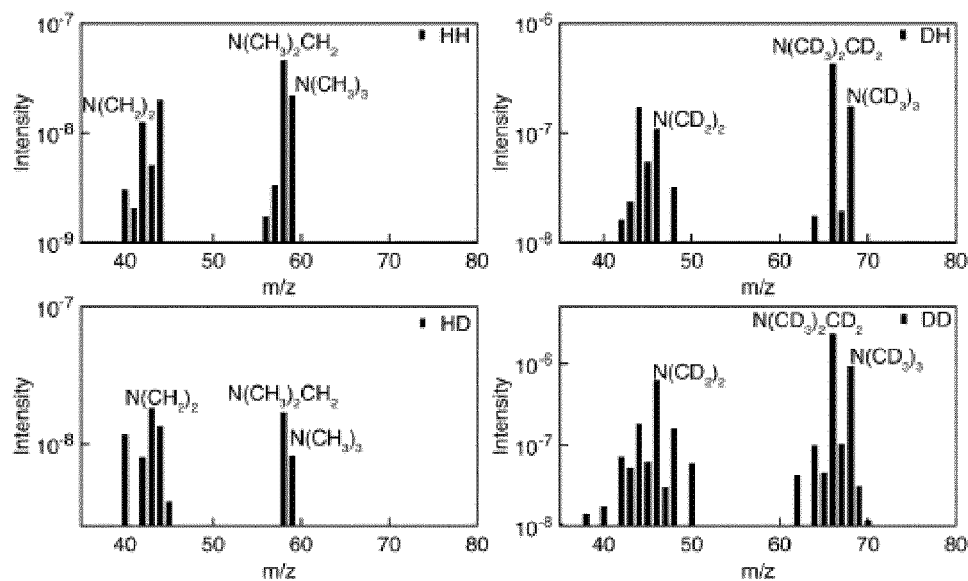
FIG. 26 shows MS spectra showing the trimethylamine (TMA) species formed in different labelled ChCl-urea DES (HH, HD, DH and DD) upon heating to 130° C.

Through heating these series of deuterated DES mixtures, the NH$_3$ produced was shown to originate from the urea component as no difference was observed between the MS spectra of HH-DES and DH-DES, whereas HD-DES and DD-DES showed an additional peak at m/z=20 corresponding to ND$_3$, FIG. 25. TMA was shown to arise from the ChCl component, the predominant peak at m/z=58 (N(CH$_3$)$_3$) was shifted to m/z=67 in both DH-DES and DD-DES indicating the formation of N(CD$_3$)$_3$, FIG. 25. It is likely that smaller quantities of dimethylamine and methylamine are also formed, however, they are masked by the TMA fragmentation.

Figure 27:
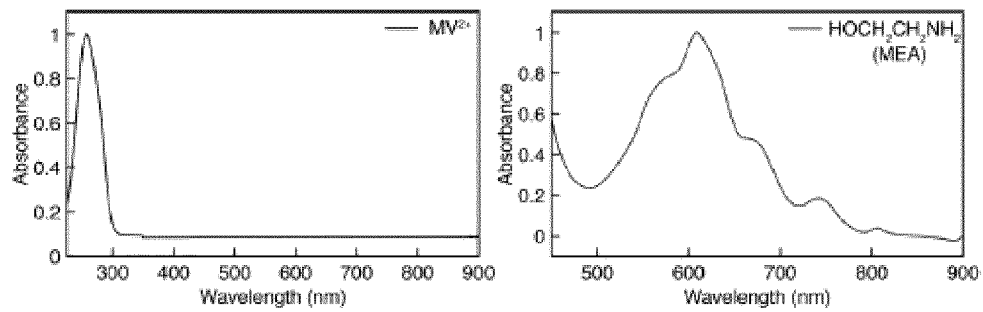
FIG. 27 shows a UV/vis spectrum showing ChCl-urea DES $MV^{2+}$ solution before (left) and after (right) the addition of excess MEA.
Figure 28:
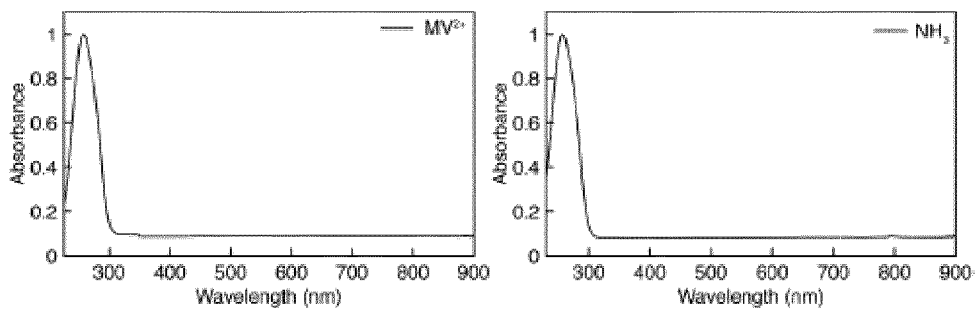
FIG. 28 shows a UV/vis spectrum showing ChCl-urea DES $MV^{2+}$ solution before (left) and after (right) the addition of excess ammonia ($NH_3$).
Figure 29:
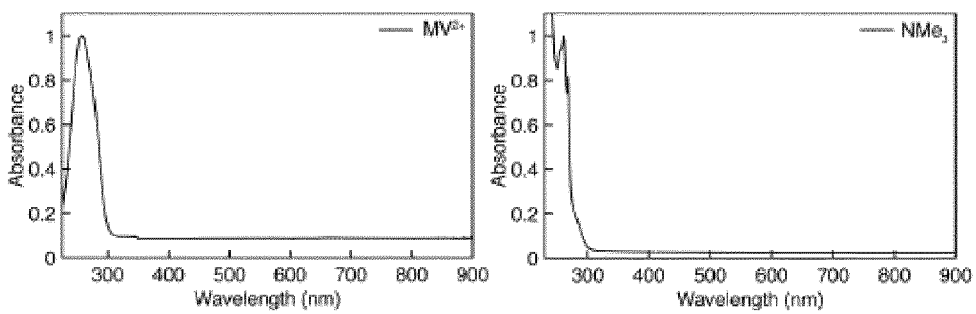
FIG. 29 shows UV/vis spectrum showing ChCl-urea DES $MV^{2+}$ solution before (left) and after (right) the addition of excess trimethylamine ($NMe_3$).

The proposed cycle (FIG. 21E) is initiated by the generation of NH$_3$ at 100° C. from condensation of urea to form biuret.[56] Upon increasing the temperature to 130° C., NH$_3$ reacts with ChCl to form TMA and monoethanolamine (MEA, not observed in the gas phase due to its low vapour pressure), which is a known reducing agent.[57-58] UV/vis studies confirmed that adding MEA to MV$^{2+}$ results in the formation of MV$^{+\cdot}$ (FIG. 27) whereas adding NH$_3$ and TMA did not (FIG. 28, 29).

The reaction of MEA with MV$^{2+}$ forms MV$^{+\cdot}$ regenerating NH$_3$.

Figure 30:
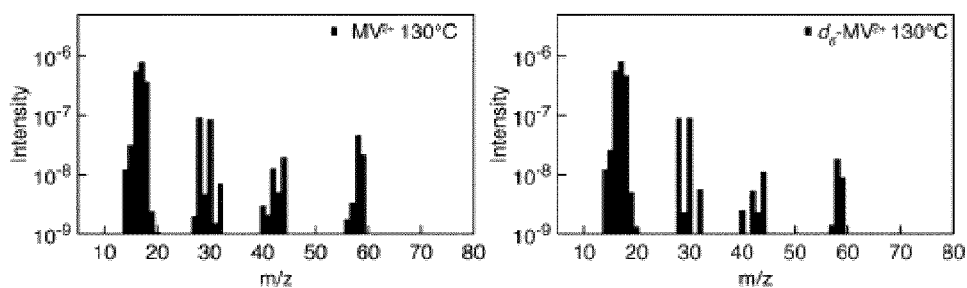
FIG. 30 shows a MS spectra of species formed upon heating ChCl-urea DES heated to 130° C. in the presence of $MV^{2+}$ (left) and d6-$MV^{2+}$ (right).

The cycle (FIG. 21E) shows how both ChCl and urea DES components play key roles. Using a deuterated MV isotopologue, d$^6$-MV$^{2+}$, showed no change in the MS and thus, any potential role of MV$^{2+}$ itself in the reduction pathway was ruled out (FIG. 30).

Figure 31:
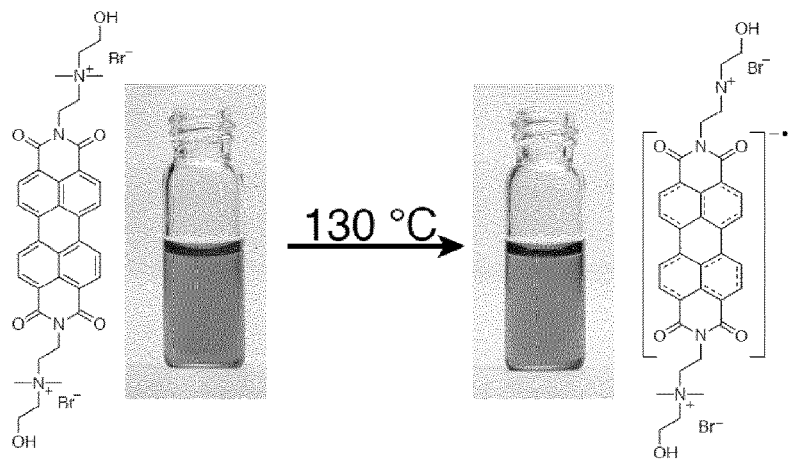
FIG. 31 shows chemical structures and images of PDI in ChCl-urea DES before and after heating to 130° C.
Figure 32:
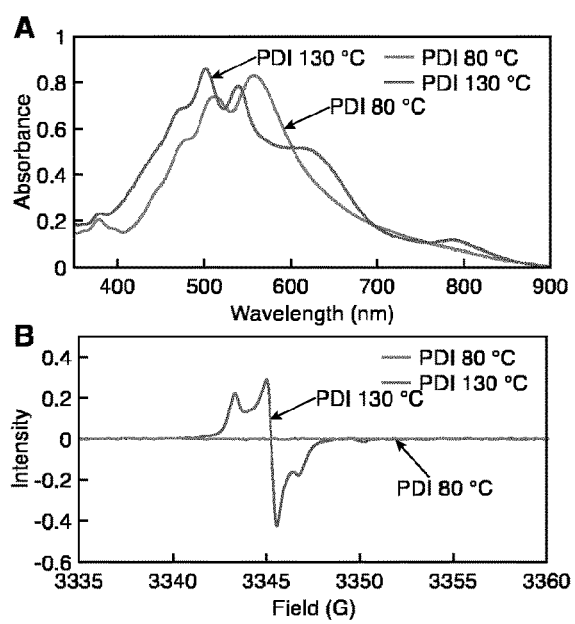
FIG. 32 shows (A) UV/Vis and (B) EPR spectra of PDI in ChCl-urea DES (0.01 mM) following heating to 80° C. (pink lines) and 130° C. (purple lines) for 1 h. All solutions were prepared and measured in air without purging.
Figure 33:
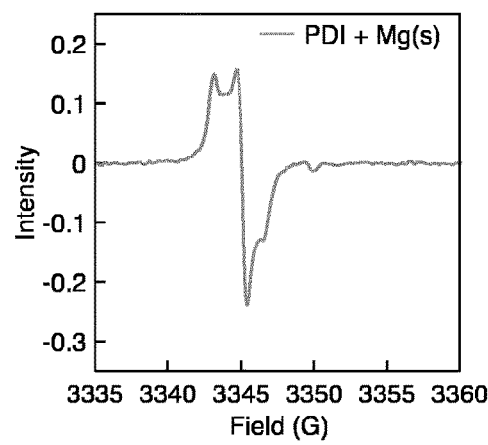
FIG. 33 shows an EPR spectrum of reduced PDI in ChCl-urea DES. Solutions were prepared by dissolving PDI (0.01 mM) in the presence of Mg(s) as a reducing agent at 80° C. (1 h). All Mg(s) was filtered off prior to the solution being transferred to the EPR tube for measurement.

Thermal mediated reduction had not been previously reported therefore this new stimuli was trialed for another class of radical species, perylene bis(diimides) (PDI), FIG. 31. Heating a solution of PDI in ChCl-urea DES to 130° C. resulted in analogous thermal reduction to that observed for MV, forming a radical species evidenced by UV/Vis and EPR spectroscopies, FIG. 32. The EPR spectrum was analogous to that of a PDI radical formed from chemical reduction, FIG. 33.

Temperature Dependence Reduction of MV$^{2+}$ to MV$^{+\cdot}$

MV$^{2+}$ 2Cl$^-$ (10 mg, 0.039 mM) was added to ChCl-urea DES (10 mL) and dissolved by heating to 80° C. for 30 min. Upon dissolution, 1.5 mL of the solution was removed, placed in a cuvette and a UV/vis spectrum was recorded. Another two solutions were prepared in an identical manner, one was heated to 100° C. for 1 h and one to 130° C. for 1 h. Following this a UV/vis spectrum was recorded.

Long Term UV/Vis Measurement

Figure 34:
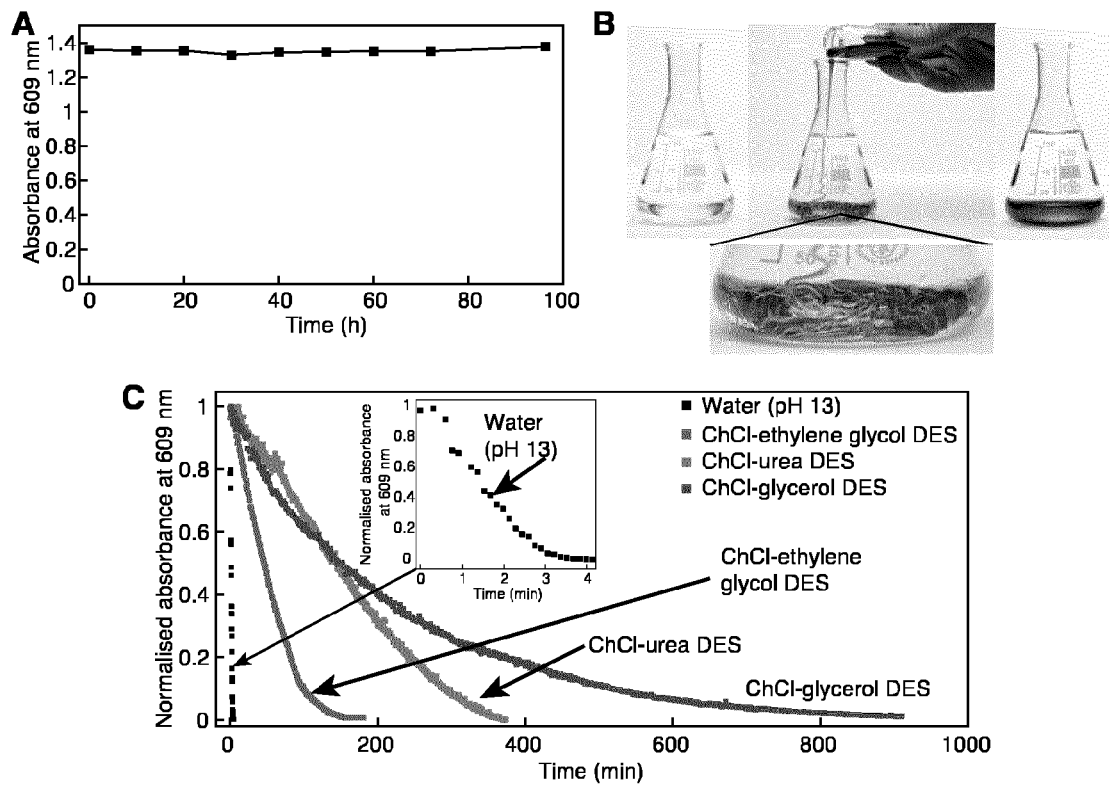
FIG. 34 shows stability of $MV^{+\cdot}$ species in DES under aerobic conditions (A). Long-term UV/vis measurement of $MV^{+\cdot}$ in ChCl-urea DES (0.39 mM). Spectra recorded over a 100 h period with no change in absorbance. (B) Images showing a solution of $MV^{+\cdot}$ in ChCl-urea DES being poured into air-saturated water highlighting how the DES structure is protecting the radical from 02. The solution remained blue until complete mixing had occurred and the DES nanostructure was destroyed. (C) Overview of the stability of $MV^{+\cdot}$ in three different DES and comparison to water (pH 13). Solutions of $MV^{+\cdot}$ were prepared by chemical reduction (MEA, 90.6 µL) and reoxidation as a function of time was measured through continuous acquisition of UV/vis spectra whilst purging with air (for DES 30 ml min$^{-1}$ for water (pH 13) 0.1 mL min$^{-1}$).

Quenching of MV$^{+\cdot}$ occurs through reaction with oxygen and typically happens readily in the liquid and solid state upon exposure to air. However, throughout all experiments we observed that the radical species was remarkably persistent under aerobic conditions. To probe the lifetime of the radical in air, a solution of MV$^{+\cdot}$ in ChCl-urea DES was exposed to air and UV/vis spectra were recorded over a 100 h period (FIG. 34A). The solution was not degassed nor was any attempt to minimise oxygen made however, remarkably, the solution showed no change in absorbance at 609 nm during this time-period. Solutions prepared and stored in air were found to remain blue for >6 months and thus we forecast a lifetime of >>6 months for MV$^{+\cdot}$ in DES. The persistence of the radical in the DES environment despite exposure to air suggested that oxygen diffusivity was minute.

This indicated that oxygen was able to permeate the solution and quench the radical but on a much slower time scale than is observed in any other solvents (weeks vs. seconds).

The low oxygen diffusivity into the DES was contributing to the long radical lifetime, however, it was unclear how stable the radical would be when introduced into an oxygenated environment or when oxygen was forced into the DES environment. As shown in FIG. 34B, when a solution of MV$^{+\cdot}$ was poured into air-saturated water the radical persisted in the DES solution. The unique nanostructure of the DES shielded the radical species from interaction with oxygen in the water and thus, a blue solution of MV$^{+\cdot}$ in DES was present at the bottom of the flask. The blue colour remained until complete mixing of the two solutions had occurred. The persistence of the radical was also observed when water was added to a DES MV$^{+\cdot}$ solution. To demonstrate the stabilisation of MV$^{+\cdot}$ in DES vs. water, oxygen was forced into the system by purging aqueous and DES MV$^{+\cdot}$ solutions with air (30 mL min$^{-1}$) and recording UV/vis spectra in parallel to monitor the quenching of MV$^{+\cdot}$ (FIG. 34C). It was necessary to degas the aqueous MV$^{+\cdot}$ solution and seal it under a N$_2$ atmosphere as, in air, the radical species did not persist long enough for any measurements to be taken. In contrast, the DES solution was not degassed or sealed. Within less than 4 min of purging with air (0.1 mL min$^{-1}$), the aqueous MV$^{+\cdot}$ solution was completely quenched, however, in DES under more extreme purging conditions (30 mL min$^{-1}$), the radical species persisted for 2-15 h, an enhancement factor of 0.9.

The prolonged radical lifetime was not found to be dependent on the viscosity of the DES. Whilst the DES with the lowest viscosity, ChCl-ethylene glycol (36 cP), did result in the shortest radical lifetime upon purging with air (FIG. 34C) the MV$^{+\cdot}$ was found to be significantly more persistent in a DES of medium viscosity, ChCl-glycerol (376 cP), with a lifetime more than double (900 vs. 400 min) that of the more viscous ChCl-urea DES (632 cP).

From these findings, it is proposed that stabilisation of the radical species arises from the unique DES nanostructure and the interactions between the radical and the solvent, which shield the species from oxygen present in the surrounding environment.

Protocol

MV$^{2+}$ 2Cl$^-$ (1 mg, 0.0039 mmol) was added to ChCl-urea DES (10 mL) and dissolved by heating to 80° C. for 30 min to give a 0.39 mM solution. The solution was then heated to 130° C. for 2 h during which time it had turned blue. A portion (1.5 mL) of the resulting blue solution was removed, placed in a cuvette and a UV/vis spectrum was recorded.

Spectra were recorded across a 100 h period in an open cuvette.

The solution was not degassed or covered in any way nor was any attempt to keep O$_2$ out made.

Purging of MV$^{+\cdot}$ in Different DES

MV$^{2+}$ 2Cl$^-$ (1 mg, 0.0039 mmol) was added to ChCl-urea DES (10 mL) and dissolved by heating to 80° C. for 30 min to give a 0.39 mM solution. Upon dissolution, 1.5 mL of the solution was removed, placed in a quartz cuvette and MEA (90.5 μL) added. The solution was stirred, purged briefly with N$_2$ and a UV/vis recorded. The solution was then purged with air at a flow rate of 30 mL min$^{-1}$ controlled by a mass flow controller (Brooks). UV/vis spectra were recorded continuously throughout the purging until absorbance at 609 nm had disappeared and the solution had reverted to colourless.

Purging of MV$^{+\cdot}$ in Water

MEA does not mediate the reduction of MV$^{2+}$ in water at a neutral pH as it exists in a protonated form however it does reduce MV$^{2+}$ in a basic solution. A solution of KOH (0.1 M) was prepared in Milli Q H$_2$O. MV$^{2+}$ 2Cl$^-$ (1 mg, 0.0039 mmol) was added to the 0.1M KOH in H$_2$O solution (10 mL) and dissolved to give a 0.39 mM solution. MEA (33.8 µL) was added to MV$^{2+}$ in 0.1 M KOH (5.7 mL) and the solution was purged with N$_2$. Upon dissolution, 1.5 mL of the solution was removed, placed in a quartz cuvette and MEA (81.5 µL) added. The cuvette was sealed with a septum and purged with N$_2$. The solution was then purged with air at a flow rate of 0.1 mL min$^{-1}$ controlled by a mass flow controller. UV/vis spectra were recorded continuously throughout the purging until absorbance at 609 nm had disappeared and the solution had reverted to colourless. The cuvette remained sealed throughout and it was purged with air.

Fabrication of the Smart Window

Figure 35:
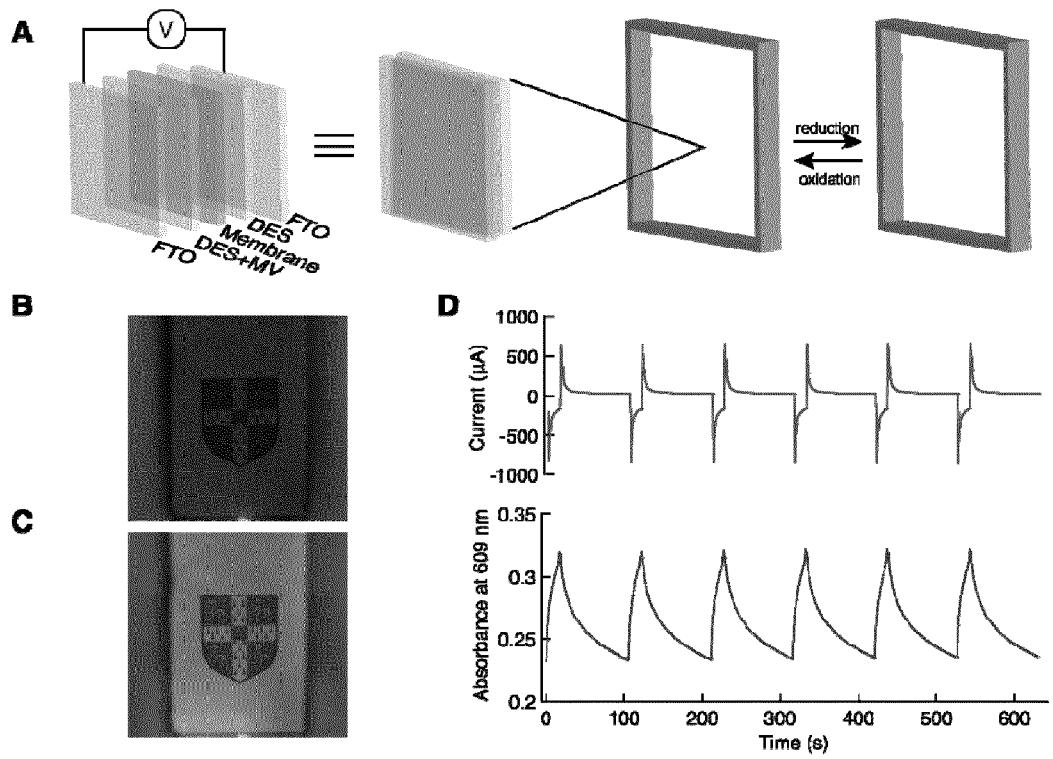
FIG. 35 shows fabrication and performance of a 'smart window' based on MV in DES. (A) Illustration of a 'smart window' showing the colour modulation with application of bias and schematic representation of the electrochromic device showing the components involved and the set up. (B) Photographs of the 'smart window' upon application of a reductive bias (−3 V, 15 s) and (C) oxidative bias (−3 V, 90 s). (D) Electrochemical switching of the 'smart window' showing the alternating bias applied (top) and resultant change in absorbance at 609 nm monitored by UV/vis spectroscopy (bottom) over multiple cycles.

A simple device was constructed consisting of two pieces of fluorine-doped tin oxide (FTO) separated by a membrane with ChCl-ethylene glycol DES on one side and the same DES with MV$^{2+}$ on the other (FIG. 35A). Upon application of a negative bias (−3V) between the two electrodes, the device reversibly changed from colourless to blue. This colour was found to be stable even when the bias was removed (FIG. 35B) and only when a positive bias (+3V) was applied did the device revert to the colourless state (FIG. 35C). Application of a negative bias (−3V) led to an increase in the absorbance at 609 nm indicative of the formation of MV$^{+\cdot}$ whilst application of a positive bias resulted in a decrease in absorbance at 609 nm confirming reoxidation to MV$^{2+}$. Switching behaviour of the device was rapid and robust, and the device could undergo multiple switching cycles without bleaching, precipitation or loss in performance (FIG. 35D).

Protocol

Fluorine-doped tin oxide (FTO, Sigma-Aldrich, 7 Ωsq−1) was cleaned by sonication in acetone followed by UV-ozone treatment for 20 min. The device was assembled from two FTO electrodes (5×2 cm) separated by a Selemion anion exchange membrane (AGC engineering, soaked for 24 h in ChCl-EG DES), sandwiched between two U-shaped butyl rubber spacers (1 mm thick). One compartment was filled with a ChCl-EG DES solution of MV$^{2+}$ 2Cl$^-$ (3.9 mM) and the other with blank ChCl-EG DES. Electrochemical switching of the device was effected by multistep chronoamperometry, alternatingly applying a −3 V and +3 V bias between the two FTO electrodes for 15 and 90 s, respectively. Coloration and de-coloration was monitored by measuring the absorbance at 609 nm by UV/vis spectroscopy.

REFERENCES

All documents mentioned in this specification are incorporated herein by reference in their entirety.
1. M. Florea and W. M. Nau, *Angew. Chem. Int. Ed.*, 2011, 50, 9338
2. Y. Zhao, D. P. Buck, D. L. Morris, M. H. Pourholami, A. I. Day and J. G Collins, *Org. Biolmol. Chem.*, 2008, 6, 4509.
3. H. Kim, Y. Kim, M. Yoon, S. Lim, S. M. Park, G. Seo, K. Kim, *J. Am. Chem. Soc.*, 2010, 132, 12200
4. S. Y. Jon, Y. H. Ko, S. H. Park, H. J. Kim, K. A. Kim, *Chem. Commun.*, 2001, 1938
5. L. S. Berbeci, W. Wang, A. E. Kaifer, *Org. Lett.*, 2008, 10, 3721
6. E. Masson, X. Ling, R. Joseph, L. Kyeremeh-Mensah, X. Lu, *RSC Adv.*, 2012, 2, 1213
7. K. Jansen, H. J. Buschmann, A. Wego, D. Döpp, C. Mayer, H. J. Drexler, H. J. Holdt and E. Schollmeyer, *J. Inclusion Phenom. Mol. Recognit. Chem.*, 2001, 39, 357
8. J. Z. Zhao, H.-J. Kim, J. Oh, S.-Y Kim, J. W. Lee, S. Sakamoto, K. Yamaguchi and K. Kim, *Angew. Chem. Int. Ed.*, 2001, 40, 4233
9. V. Lewin, J. Rivollier, S. Coudert, D.-A Buisson, D. Baumann, B. Rousseau, F.-X. Legrand, H. Kouřilova, P. Berthault, J.-P Dognon, M.-P Heck and G. Huber, *Eur. J. Org. Chem.*, 2013, 3857
10. D. Jiao and O. A. Scherman, *Green Chem.*, 2012, 14, 2445
11. I. W. Wyman and D. H. Macartney, *Org. Biolmol. Chem.*, 2010, 8, 253
12. V. Sindelar, K. Moon and A. E. Kaifer, *Org. Lett.*, 2004, 6, 2665
13. W. Wang and A. E. Kaifer, *Supramol. Chem.*, 2010, 22, 710
14. T. K. Monhaphol, S. Andersson and L. Sun, *Chem.-Eur. J.*, 2011, 17, 11604
15. K. I. Assaf and W. M. Nau, *Chem. Soc. Rev.*, 2015, 44, 394
16. Gilberg et al. *Org. Lett.* 2014, 16, 2446
17. Fukino, T., Yamagishi, H. & Aida, T. Redox-Responsive Molecular Systems and Materials. Adv. Mater. 29, 1603888-17 (2016).
18. Li, Z., Barnes, J. C., Bosoy, A., Stoddart, J. F. & Zink, J. I. Mesoporous silica nanoparticles in biomedical applications. Chem. Soc. Rev. 41, 2590-17 (2012).
19. Thakur, V. K., Ding, G., Ma, J., Lee, P. S. & Lu, X. Hybrid Materials and Polymer Electrolytes for Electrochromic Device Applications. Adv. Mater. 24, 4071-4096 (2012).
20. Lin, W.-P., Liu, S.-J., Gong, T., Zhao, Q. & Huang, W. Polymer-Based Resistive Memory Materials and Devices. Adv. Mater. 26, 570-606 (2013).
21. Kim, D. J. et al. Redox-Active Macrocycles for Organic Rechargeable Batteries. J. Am. Chem. Soc. 139, 6635-6643 (2017).
22. Cram, D. J., Tanner, M. E. & Thomas, R. The taming of cyclobutadiene. Angew. Chem. Int. Ed. 30, 1024-1027 (1991).
23. Mal, P., Breiner, B., Rissanen, K. & Nitschke, J. R. White phosphorus is air-stable within a self-assembled tetrahedral capsule. Science 324, 1697-1699 (2009).
24. Lopez, N. et al. Reversible reduction of oxygen to peroxide facilitated by molecular recognition. Science 335, 450-453 (2012).
25. Jiao, Y. et al. A Supramolecularly Activated Radical Cation for Accelerated Catalytic Oxidation. Angew. Chem. Int. Ed. 55, 8933-8937 (2016).
26. Benson, C. R. et al. Extreme Stabilization and Redox Switching of Organic Anions and Radical Anions by Large-Cavity, CH Hydrogen-Bonding Cyanostar Macrocycles. J. Am. Chem. Soc. 138, 15057-15065 (2016).
27. Song, Q., Li, F., Wang, Z. & Zhang, X. A supramolecular strategy for tuning the energy level of naphthalenediimide: Promoted formation of radical anions with extraordinary stability. Chem. Sci. 6, 3342-3346 (2015).

28. Ghosh, I., Ghosh, T., Bardagi, J. I. & Kӧnig, B. Reduction of aryl halides by consecutive visible light-induced electron transfer processes. Science 346, 725-728 (2014).
29. Monk, P. M. S., Rosseinsky, D. R. & Mortimer, R. J. Electrochromic Materials and Devices Based on Viologens, 57-90 (Wiley-VCH Verlag GmbH & Co. KGaA, 2013).
30. Sweetser, P. B. Colorimetric determination of trace levels of oxygen in gases with the photochemicallygenerated methyl viologen radical-cation. Anal. Chem. 39, 979-982 (1967).
31. Jeon, W. S., Kim, H.-J., Lee, C. & Kim, K. Control of the stoichiometry in host guest complexation by redox chemistry of guests: Inclusion of methylviologen in cucurbit[8]uril. Chem. Commun. 1828-1829 (2002).
32. Kim, H.-J., Jeon, W. S., Ko, Y. H. & Kim, K. Inclusion of methylviologen in cucurbit[7]uril. Proc. Natl. Acad. Sci. U.S.A. 99, 5007-5011 (2002).
33. Zhang, L. et al. A two-dimensional single-layer supramolecular organic framework that is driven by viologen radical cation dimerization and further promoted by cucurbit[8]uril. Polym. Chem. 5, 4715-4721 (2014).
34. Fiala, T. et al. Bambusuril as a One-Electron Donor for Photoinduced Electron Transfer to Methyl Viologen in Mixed Crystals. J. Am. Chem. Soc. 139, 2597-2603 (2017).
35. Wu, J., Tao, C., Li, Y., Li, J. & Yu, J. Methyl viologen-templated zinc gallophosphate zeolitic material with dual photo-/thermochromism and tuneable photovoltaic activity. Chem. Sci. 6, 2922-2927 (2015).
36. Odell, B. et al. Cyclobis(paraquat-p-phenylene). a tetracationic multipurpose receptor. Angew. Chem., Int. Ed. 27, 1547-1550 (1988).
37. Trabolsi, A. et al. Radically enhanced molecular recognition. Nat. Chem. 2, 42-49 (2009).
38. Barnes, J. C. et al. A radically configurable six-state compound. Science 339, 429-433 (2013).
39. Barnes, J. C. et al. Solid-State Characterization and Photoinduced Intramolecular Electron Transfer in a Nanoconfined Octacationic Homo[2]Catenane. J. Am. Chem. Soc. 136, 10569-10572 (2014).
40. Abbott, A. P., Capper, G., Davies, D. L., Rasheed, R. K. & Tambyrajah, V. Novel solventproperties of choline chloride/urea mixtures. Chem. Commun. 0, 70-71 (2002).
41. Abbott, A. P., Boothby, D., Capper, G., Davies, D. L. & Rasheed, R. K. Deep Eutectic SolventsFormed between Choline Chloride and Carboxylic Acids: Versatile Alternatives to IonicLiquids. J. Am. Chem. Soc. 126, 9142-9147 (2004).
42. Smith, E. L., Abbott, A. P. & Ryder, K. S. Deep Eutectic Solvents (DESs) and Their Applications. Chem. Rev. 114, 11060-11082 (2014).
43. Zhang, Q., De Oliveira Vigier, K., Royer, S. & Jêrôme, F. Deep eutectic solvents: syntheses, properties and applications. Chem. Soc. Rev. 41, 7108-39 (2012).
44. Hammond, O. S., Bowron, D. T. & Edler, K. J. Liquid structure of the choline chloride-urea deep eutectic solvent (reline) from neutron diffraction and atomistic modelling. Green Chem.18, 2736-2744 (2016).
45. Ashworth, C. R., Matthews, R. P., Welton, T. & Hunt, P. A. Doubly ionic hydrogen bond interactions within the choline chloride-urea deep eutectic solvent. Phys. Chem. Chem. Phys. 18, 18145-18160 (2016).
46. Hammond, O. S., Bowron, D. T. & Edler, K. J. The Effect of Water upon Deep Eutectic Solvent Nanostructure: An Unusual Transition from Ionic Mixture to Aqueous Solution. Angew. Chem. Int. Ed. 52, 3074-5 (2017).
47. Abbott, A. P., Nandhra, S., Postlethwaite, S., Smith, E. L. & Ryder, K. S. Electroless deposition of metallic silver from a choline chloride-based ionic liquid: a study using acoustic impedance spectroscopy, SEM and atomic force microscopy. Phys. Chem. Chem. Phys. 9, 3735-9 (2007).
48. Liao, H.-G., Jiang, Y.-X., Zhou, Z.-Y., Chen, S.-P. & Sun, S.-G. Shape-Controlled Synthesis of Gold Nanoparticles in Deep Eutectic Solvents for Studies of Structure-Functionality Relationships in Electrocatalysis. Angew. Chem. Int. Ed. 47, 9100-9103 (2008).
49. Garcia, G., Aparicio, S., Ullah, R. & Atilhan, M. Deep Eutectic Solvents: Physicochemical Properties and Gas Separation Applications. Energy Fuels 29, 2616-2644 (2015).
50. Alonso, D. A. et al. Deep Eutectic Solvents: The Organic Reaction Medium of the Century. Eur. J. Org. Chem. 2016, 612-632 (2016).
51. Vidal, C., García-Á Ivarez, J., Hernán-Gómez, A., Kennedy, A. R. & Hevia, E. Exploiting Deep Eutectic Solvents and Organolithium Reagent Partnerships: Chemoselective Ultrafast Addition to Imines and Quinolines Under Aerobic Ambient Temperature Conditions. Angew. Chem. Int. Ed. 128, 16379-16382 (2016).
52. Cruz, H., Jordãno, N. & Branco, L. C. Deep eutectic solvents (DESs) as low-cost and green electrolytes for electrochromic devices. Green Chem. 19, 1653-1658 (2017).
53. Ebbesen, T. W., Levey, G. & Patterson, L. K. Photoreduction of methyl viologen in aqueous neutral solution without additives. Nature 298, 545-548 (1982).
54. Xu, G. et al. Photochromism of a Methyl Viologen Bismuth(III) Chloride: Structural Variation Before and After UV Irradiation. Angew. Chem. Int. Ed. 46, 3249-3251 (2007).
55. Peon, J. et al. Excited state dynamics of methyl viologen. Ultrafast photoreduction in methanol and fluorescence in acetonitrile. J. Phys. Chem. A 105, 5768-5777 (2001).
56. Redemann, C. E., Riesenfeld, F. C. & Viola, F. S. L. Formation of biuret from urea. Ind. Eng. Chem. Res. 50, 633-636 (1958).
57. Meltsner, M., Wohlberg, C. & Kleiner, M. J. Reduction of organic compounds by ethanolamines. J. Am. Chem. Soc. 57, 2554-2554 (1935).
58. Kremer, C. B. & Kress, B. Alkanolamines. iv. reducing properties of the amino alcohols. J. Am. Chem. Soc. 60, 1031-1032 (1938).

The invention claimed is:

1. A composition comprising a macrocyclic host dissolved in a deep eutectic solvent, wherein the host is selected from the group consisting of cucurbituril, cyclodextrin, calix[n]arene, and crown ether; wherein the deep eutectic solvent is a Type III deep eutectic solvent, which comprises a first component that is an ionic species and a second component that is a hydrogen bond donor; and wherein the macrocyclic host is in complex with a guest molecule.

2. The composition according to claim 1, wherein the host comprises a cucurbituril host or a cyclodextrin host where the cucurbituril host is selected from the group consisting of CB[5], CB[6], CB[7] and CB[8] and the cyclodextrin host is selected from the group consisting of α-, β- and γ-cyclodextrin.

3. The composition according to claim 1, wherein the ionic species comprises an ammonium, phosphonium or sulfonium cation, and a Lewis base anion.

4. The composition according to claim 3, wherein the ionic species comprises an ammonium cation selected from the group consisting of choline chloride, ethylammonium chloride, N-ethyl-2-hydroxy-N,N-dimethylethanaminium chloride, 2-(chlorocarbonyloxy)-N,N,N-trimethyl-ethanaminium chloride, N-benxyl-2-hydroxy-N,N-dimethylethanaminium chloride, tetramethylaminium chloride, tetrabutylaminium chloride, methyltriphenylphosphonium bromide, methyltriphenylphosphonium chloride, benzyltriphenylphosphonium bromide, tetraethylaminium bromide, tetrabutylaminium bromide, 2-hydroxy-N,N-diethyl-ethanaminium chloride, 2 chloro-N,N,N-trimethyl-ethanaminium chloride and acetyl choline chloride.

5. The composition according to claim 4, wherein the ionic species is choline chloride.

6. The composition according to claim 1, wherein the hydrogen bond donor is selected from the group consisting of urea, p-toluenesulfonic acid, acetamide, 1-methyl-urea, 1,3-dimethylurea, 1,1-dimethylurea, imidazole, 2,2,2 trifluoroacetamide, thiourea, benzamide, glycerol, ethylene glycol, malonic acid, benzoic acid, adipic acid, oxalic acid, succinic acid, citric acid, phenylacetic acid, phenylpropionic acid, tricarballylic acid, levulinic acid, itaconic acid, xylitol, sorbitol, tartaric acid, isosorbide, 4 hydroxybenzoic acid, caffeic acid, coumaric acid, cinnamic acid, suberic acid, gallic acid and resorcinol.

7. The composition according to claim 1, wherein the deep eutectic solvent is a mixture of choline chloride and urea, or a mixture of p-toluenesulfonic acid and urea.

8. A method of preparing the composition according to claim 1, the method comprising the steps of providing a composition comprising a deep eutectic solvent, a host and one or more guests, and permitting the host and the one or more guests to form a complex;

or the step of mixing a deep eutectic solvent with a host in complex with one or more guests.

9. The method according to claim 8, comprising mixing a first component of the deep eutectic solvent with the host and then subsequently mixing a further component of the deep eutectic solvent together with the first component and the host.

10. The method according to claim 8, further comprising first mixing a guest with the deep eutectic solvent and then adding the host.

11. The composition according To claim 1, further comprising the deep eutectic solvent and the macrocyclic host in complex with one or more guests.

* * * * *